US010626187B2

(12) United States Patent
Wiltzius et al.

(10) Patent No.: US 10,626,187 B2
(45) Date of Patent: Apr. 21, 2020

(54) ANTIGEN BINDING MOLECULES SPECIFIC FOR AN ANTI-CD19 SCFV

(71) Applicant: KITE PHARMA, INC., Santa Monica, CA (US)

(72) Inventors: Jed Wiltzius, Woodland Hills, CA (US); Stuart Sievers, Van Nuys, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 142 days.

(21) Appl. No.: 15/717,691

(22) Filed: Sep. 27, 2017

(65) Prior Publication Data
US 2018/0086846 A1 Mar. 29, 2018

Related U.S. Application Data

(60) Provisional application No. 62/401,007, filed on Sep. 28, 2016.

(51) Int. Cl.
C07K 16/42 (2006.01)
A61K 35/17 (2015.01)
A61K 39/395 (2006.01)
C07K 16/28 (2006.01)
G01N 33/569 (2006.01)
G01N 33/68 (2006.01)

(52) U.S. Cl.
CPC .......... C07K 16/4258 (2013.01); A61K 35/17 (2013.01); A61K 39/3955 (2013.01); C07K 16/2803 (2013.01); C07K 16/4208 (2013.01); G01N 33/56972 (2013.01); G01N 33/686 (2013.01); C07K 2317/20 (2013.01); C07K 2317/24 (2013.01); C07K 2317/51 (2013.01); C07K 2317/515 (2013.01); C07K 2317/565 (2013.01); C07K 2317/622 (2013.01); C07K 2319/03 (2013.01); C07K 2319/33 (2013.01); C07K 2319/74 (2013.01)

(58) Field of Classification Search
None
See application file for complete search history.

(56) References Cited

U.S. PATENT DOCUMENTS

| 5,223,409 | A | 6/1993 | Ladner |
| 7,709,226 | B2 | 5/2010 | Foote |
| 2016/0096902 | A1* | 4/2016 | Cooper ............. C07K 16/2803 424/178.1 |

FOREIGN PATENT DOCUMENTS

| TW | 201811828 A | 7/2017 |
| WO | 2014/190273 A1 | 11/2014 |
| WO | WO2016019300 A1 | 7/2015 |

OTHER PUBLICATIONS

Pan, Y. et al.; Anti-idiotypic Antibodies: Biological Function and Structural Studies; The FASEB Journal, Jan. 1995; pp. 43-49; vol. 9, No. 1.
Zola, Y. et al.; Preparation and Characterization of a Chimeric CD19 Monoclonal Antibody;Immunology and Cell Biology; Dec. 1991; pp. 411-422; 69 ( Pt 6).
Kochenderfer, J.N., et al.; Construction and Pre-clinical Evaluation of an Anti-CD19 Chimeric Antigen Receptor; J Immunother. Sep. 2009; pp. 689-702.; 32(7): doi:10.1097/CJI.0b013e3181ac6138.
Jena, B., et a.; Chimeric Antigen Receptor (CAR)-Specific Monoclonal Antibody to Detect CD19-Specific T Cells in Clinical Trials; (2013) PLoS One 8(3): e57838. doi:10.1371/journal.pone.0057838.
Golub, et al., "Immunology—A Synthesis (2nd Edition)", Sinauer Assoc., Sunderland, Mass. (1991), table of contents only, 13 pages.
Stocks, "Intrabodies: production and promise" Drug Discovery Today, 2004, 9(22):960-66.
Bird et al., "Single-chain antigen-binding proteins", 1988, Science 242:423-26.
Huston et al., Protein engineering of antibody binding sites: recovery of specific activity in an anti-digoxin single-chain Fv analogue produced in *Escherichia coli* PNAS, Aug. 1, 1988, 85 (16) 5879-5883.
Holliger et al., "Diabodies: Small Bivalen and Bispecific Antibody Fagments" Proc Natl Acad Sci U.S.A., 1993, 90:6444-48 Biophysics.
Poljak et al., "Production and structure of diabodies" Structure, 1994, vol. 2, No. 12: 1121-23.
Perisic et al., "Crystal structure of a diabody, a bivalent antibody fragment" Structure, 1994, 2(12): 1217-26.
Korndorfer et al., "Crystallographic Analysis of an "Anticalin" With Tailored Specificity for Fluorescein Reveals High Structural Plasticity of the Lipocalin Loop Region" Proteins: Structure, Function, and Bioinformatics, 2003, 53(1):121-129 Wiley-Liss, Inc.
Roque et al., "Antibodies and Genetically Engineered Related Molecules: Production and Purification", Biotechnol. Prog. 20:639-654 (2004).
Kabat et al. "Sequences of Proteins of Immunological Interest", 1991, 5th Ed., NIH Publication 91-3242, Bethesda MD title page, publication page, and table of contents only, 10 pages.
Chothia et al., "Canonical structures for the hypervariable regions of immunoglobulins", J Mol Biol, 1987, 196: 901-917.
Al-Lazikani et al., "Standard conformations for the canonical structures of immunoglobulins" J Mol Biol, 1997, 273: 927-948.
Chothia et al., "Structural repertoire of the human VH segments" J Mol Biol, 1992, 227: 799-817.
Tramontano et al., "Framework residue 71 is a major determinant of the position and conformation of the second hypervariable region in the VH domains of immunoglobulins" J Mol Biol, 1990, 215(1): 175-82.
Bricogne, "Direct phase determination by entropy maximization and likelihood ranking: status report and perspectives", Acta Crystallogr D Biol Crystallogr, 1993, 49(Pt 1): 37-60.

(Continued)

Primary Examiner — Sharon X Wen
(74) Attorney, Agent, or Firm — Henry P. Wu

(57) ABSTRACT

Isolated antigen binding molecules that specifically bind to an anti-CD19 scFv comprising SEQ ID NO: 1 are provided. The antigen binding molecules can be used in the methods provided herein.

12 Claims, 26 Drawing Sheets
Specification includes a Sequence Listing.

(56) References Cited

OTHER PUBLICATIONS

Bricogne, "[23] Bayesian statistical viewpoint on structure determination: Basic concepts and examples", Meth Enzymol, 1997, 276A: 361-423.
Roversi et al., "Modeling prior distributions of atoms for macromolecular refinement and completion", Acta Crystallogr D Biol Crystallogr, 2000, 56 (Pt 10): 1316-1323.
Champe et al., "Monoclonal Antibodies That Block the Activity of Leukocyte Function-associated Antigen 1 Recognize Three Discrete Epitopes in the Inserted Domain of CD11a", J Biol Chem, 1995, 270(3): 1388-94.
Cunningham et al., "High-resolution epitope mapping of hGH-receptor interactions by alanine-scanning mutagenesis", Science 244(4908): 1081-85 (1989).
Hartl et al., "Genetics: Principles and Analysis", 1997, Jones and Bartlett Publishers.
Dayhoff et al. A model of evolutionary change in proteins, in Dayhoff, M.O. Edition, Atlas of Protein Sequence and Structure, 1978, Natl. Biomed. Res. Found., Washington DC, 5(3), 345-352.
Henilkoff et al. "Amino acid substitution matrices from protein blocks", Proc Natl Acad Sci U S A., 89(22): 10915-10919, Nov. 15, 1992.
Bruggenmann et al. "Production of human antibody repertoires in transgenic mice", 1Curr. Opin. Biotechnol. 1997, 8:455-58.
Burton et al., "Human Antibodies from Combinatorial libraries", Advances in immunology, 1994, vol. 57, 191-280.
Winter, et al., "Making Antibodies by Phage Display Technology", Annual Review of Immunology, Publication Annual Review of Immunology, 1994, 12(1):433-455.
Huse, et al., "Generation of a Large Combinatorial Library of the Immunoglobulin Repertoire in Phage Lambda", Science, 1989, 246(4935):1275-1281.
Sastry et al. "Cloning of the immunological repertoire in *Escherichia coli* for generation of monoclonal catalytic antibodies: construction of a heavy chain variable region-specific cDNA library". Proceedings of the National Academy of Sciences of the United States of America. 1989, 86(15):5728-5732.
Kang et al., "Linkage of recognition and replication functions by assembling combinatorial antibody Fab libraries along phage surfaces", Proc Natl Acad Sci U S A., May 15, 1991, 88(10):4363-6.
Hoogenboom et al., "By-passing immunisation", Journal of Molecular Biology, 1992, 227(2):381-388.
Berzofsky, et al. "Antigen-Antibody interaction and Monoclonal Antibodies", Fundamental immunology, editor, William E. Paul.—7th ed., (2013), Ch 7, Lippincott Williams & Wilkins.
Schlebusch et al., "Production of a Single-Chain Fragment of the Murine Anti-Idiotypic Antibody ACA125 as Phage-Displayed and Soluble Antibody by Recombinant Phage Antibody Technique", 1997, Hybridoma 16:47-52.
Baines, et al., "Purification of Immunoglobulin G (IgG)", Methods in Molecular Biology, 1992, vol. 10: Immunochemical Protocols, 10:79-104 (The Humana Press).
Wyckoff et al., eds., Methods in Enzymology vol. 114—Diffraction Methods for Biological Macromolecules, Academic Press, Orlando, FL; title page, publication page, and table of contents only, 5 pages (1985).
Wyckoff et al., eds., Methods in Enzymology vol. 115. Diffraction Methods for Biological Macromolecules, Academic Press, Orlando, FL; title page, publication page, and table of contents only, 4 pages (1985).
Alting-Mees et al., "Monoclonal Antibody Expression Libraries: A Rapid Alternative to Hybridomas", (1990) Strategies in Molecular Biology 3:1-9.
Honegger et al. "Yet Another Numbering Scheme for Immunoglobulin Variable Domains: An Automatic Modeling and Analysis Tool" J. Mol. Biol., 2001, 309, 657-670.
Verber, et al., "The design of metabolically-stable peptide analogs,". Trends in Neurosciences, Sep. 1985, pp. 392-396.
Evans et al. "Design of nonpeptidal ligands for a peptide receptor: cholecystokinin antagonists" J. Med. Chem, 1987 30:1229-39.
Nicholson et al., Construction and Characterisation of a Functional CD19 Specific Single Chain Fv Fragment for Immunotherapy of B Lineage Leukaemia and Lymphoma Mol Immunol, 1997, vol. 34, No. 16-17:1157-65, Elsavier.
Chayen, "The role of oil in macromolecular crystallization", Structure, 1997, 5(10): 1269-1274.
Giege et al., "Crystallogenesis of biological macromolecules: facts and perspectives", Acta Crystallogr D Biol Crystallogr, 1994, 50(Pt 4): 339-350.
McPherson, "Current approaches to macromolecular crystallization", Eur J Biochem, 1990, 189: 1-23.
McPherson, "Crystallization of Proteins from Polyethylene Glycol", J Biol Chem, 1976, 251(20): 6300-6303.
Gautier et al. "Site-Specific Protein Labeling, Methods and Protocols", Springer 2015, pp. 1-267.
Stauber et al. "Development and Applications of Enhanced Green Fluorescent Protein Mutants", BioTechniques, Mar. 1998, vol. 24, No. 3:462-471.
Heim et al. "Engineering green fluorescent protein for improved brightness, longer wavelengths and fluorescence resonance energy transfer", 1996, Current Biology vol. 6, No. 2:178-182.
Johnson et al. "Molecular Probe Handbook A Guide to Fluorescent Probes and Labeling Technologies" 11th Edition, Life Technologies (2010).
Ichiki et al., "Regulation of the expression of human C epsilon germline transcript. Identification of a novel IL-4 responsive element", http://www.jimmunol.org/content/150/12/5408 J Immunol 1993; 150:5408-5417.
Strack, "Protein labeling in cells", Nature Methods, Jan. 2016, vol. 13, No. 1, p. 33.
Obermaier et al. "Principles of Protein Labeling Techniques. In: Posch A. (eds) Proteomic Profiling. Methods in Molecular Biology", 2015, vol. 1295. , Humana Press, New York, NY.
Chothia et al., "Conformations of immunoglobulin hypervariable regions", Nature, ,1989, 342(6252):877-883.
Fauchere, "Elements for the Rational Design of Peptide Drugs", Advances in Drug Research, vol. 15, 1986, 41 pages.
Torikai et al.; "A foundation for universal T-cell based immunotherapy: T cells engineered to express a CD19-specific chimeric-antigen-receptor and eliminate expression of endogenous TCR," Blood, Jun. 14, 2012 (Jun. 14, 2012), vol. 119, No. 24, pp. 5697-5705.
De Oliveira et al., "A CD19/Fc fusion protein for detection of anti-CD19 chimeric antigen receptors," Journal of Translational Medicine, Jan. 29, 2013 (Jan. 29, 2013), vol. 11, pp. 1-9.
Zheng, el al., "Protein L: a novel reagent for the detection of Chimeric Antigen Receptor (CAR) expression by flow cytometry," Journal of Translational Medicine, Feb. 13, 2012(Feb. 13, 2012), vol. 10, pp. 1-6.
Kiebak, et el. "A safeguard eliminates T cell receptor gene-modified autoreactive T cells after adoptive transfer," Proceedings of the National Academy of Sciences, Jan. 15, 2008 (Jan. 15, 2008), vol. 105, No. 2, pp. 623-628.
Kawalekar, et al. "Distinct Signaling of Coreceptors Regulates Specific Metabolism Pathways and Impacts Memory Development in CART Cells," Immunity, Feb. 16, 2016 (Feb. 16, 2016), vol. 44, pp. 380-390.
International Search Report and Written Opinion for International Application No. PCT/US2017/053790 dated Mar. 5, 2018.

\* cited by examiner

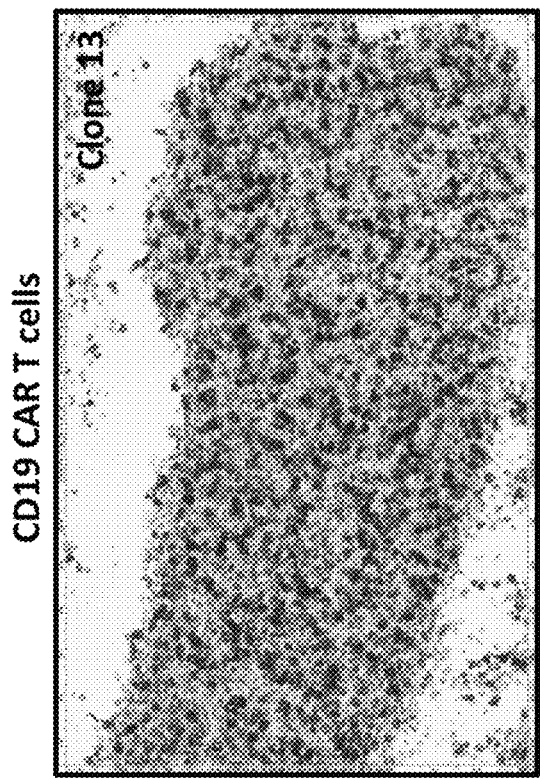
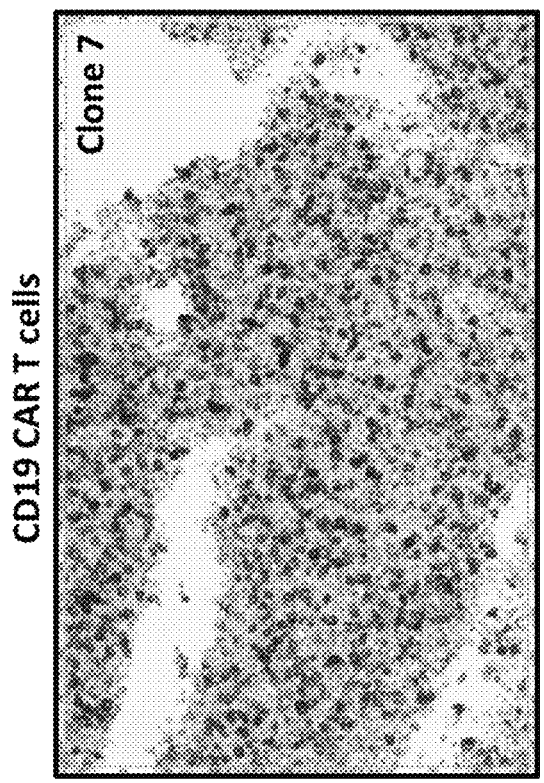
Figure 3

CD19 CAR T Cells
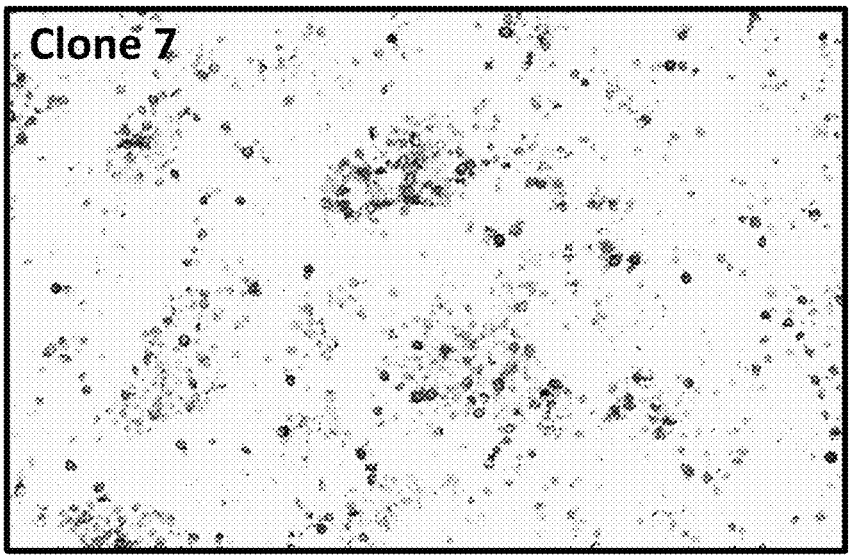
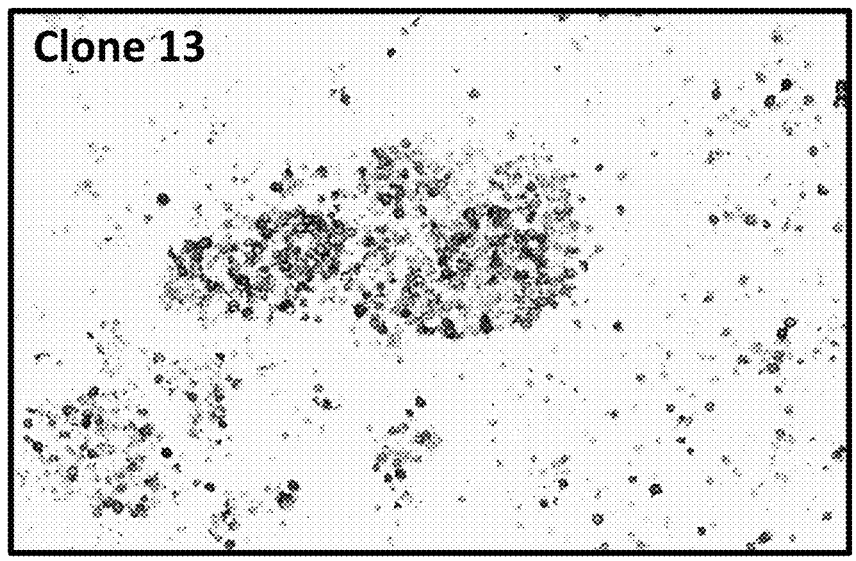
Figure 4A

PBMC Control
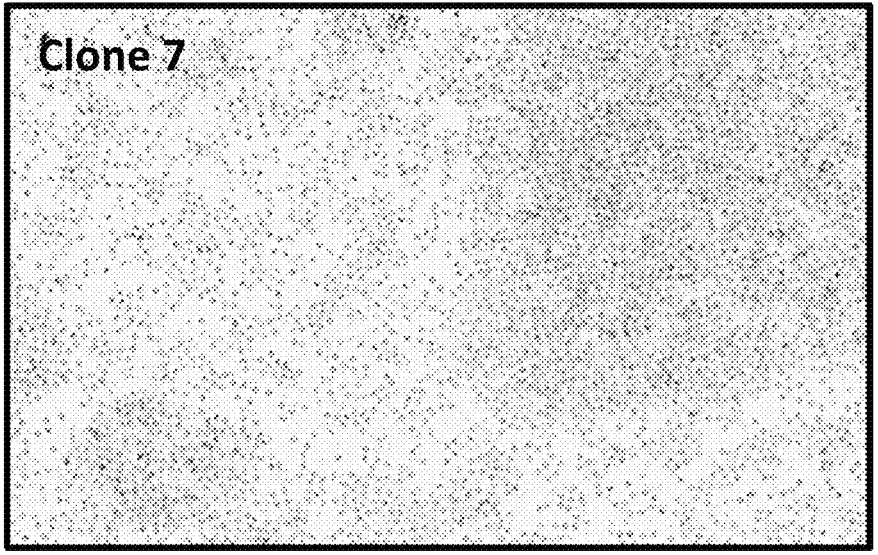
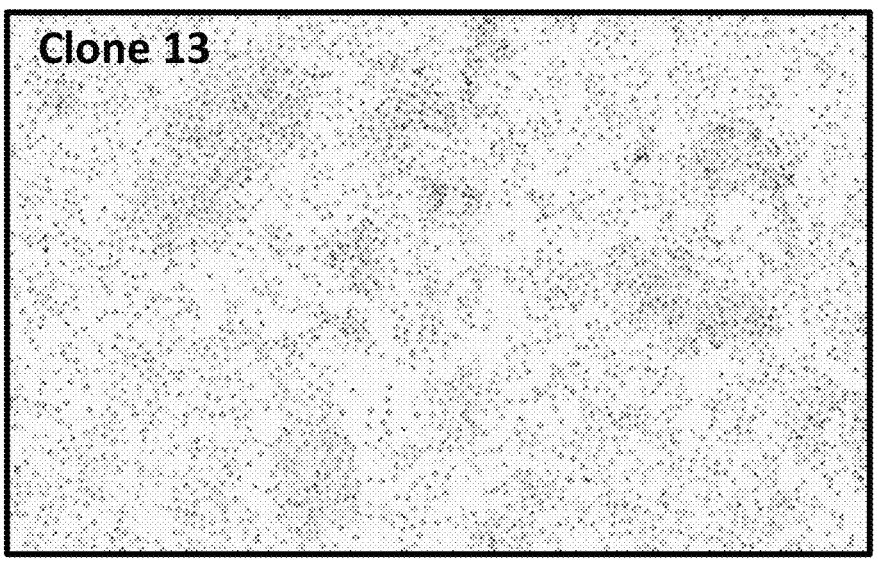
Figure 4B

Clone 7 VH DNA

ATGGAGACTGGGCTGCGCTGGCTTCTCCTGGTCGCTGTGCTCAAAGGTGTCCAGTGTCAGGAGCAGCT
GGAGGAGTCCGGGGGAGACCTGGTCAAGCCTGGAGGAACCCTGACAGTCACCTGCAAAGCCTCTGGA
TTCTCCTTCAGTAACAATGGAATTTGCTGGGTCCGCCAGGCTCCAGGGAAGGGGCTGGAGTGGATCGG
ATGTCTTTATGTTGGTAGTAGTGATACCACTTACTACGCGAGCTGGGCGAAAGGCCGATTCACCATCTC
CAAAAGCTCGTCGACCACGGTGACTCTACAAATGACCAGTCTGACAGTCGCGGACACGGCCACCTATT
TCTGTACGATAAATCTCGGCTTGTGGGGCCCCGGCACCCTGGTCACCGTCTCCTCA (SEQ ID NO: 2)

Clone 7 VH AA (CDRs underlined)
METGLRWLLLVAVLKGVQCQEQLEESGGDLVKPGGTLTVTCKAS<u>GFSFSNN</u>GICWVRQAPGKGLEWIGCL
<u>YVGSSD</u>TTYYASWAKGRFTISKSSSTTVTLQMTSLTVADTATYFCT<u>INLGL</u>WGPGTLVTVSS (SEQ ID NO: 3)

Clone 7 HC AA (CDRs underlined)
METGLRWLLLVAVLKGVQCQEQLEESGGDLVKPGGTLTVTCKAS<u>GFSFSNN</u>GICWVRQAPGKGLEWIGCL
<u>YVGSSD</u>TTYYASWAKGRFTISKSSSTTVTLQMTSLTVADTATYFCT<u>INLGL</u>WGPGTLVTVSSGQPKAPSVFPL
APCCGDTPSSTVTLGCLVKGYLPEPVTVTWNSGTLTNGVRTFPSVRQSSGLYSLSSVVSVTSSSQPVTCNVA
HPATNTKVDKTVAPSTCSKPTCPPPELLGGPSVFIFPPKPKDTLMISRTPEVTCVVVDVSQDDPEVQFTWYI
NNEQVRTARPPLREQQFNSTIRVVSTLPIAHQDWLRGKEFKCKVHNKALPAPIEKTISKARGQPLEPKVYTM
GPPREELSSRSVSLTCMINGFYPSDISVEWEKNGKAEDNYKTTPAVLDSDGSYFLYSKLSVPTSEWQRGDVF
TCSVMHEALHNHYTQKSISRSPGK (SEQ ID NO: 4)

Clone 7 VH CDR1 AA
GFSFSNN (SEQ ID NO: 5)

Clone 7 VH CDR2 AA
YVGSSD (SEQ ID NO: 6)

Clone 7 VH CDR3 AA
NLGL (SEQ ID NO: 7)

Figure 5

Clone 7 VL DNA
ATGGACACGAGGGCCCCCACTCAGCTGCTGGGGCTCCTGCTGCTCTGGCTCCCAGGTGCCACATTTGCC
ATCGTGGTGACCCAGACTCCATCTTCCAAGTCTGTCCCTGTGGGAGGCACAGTCACCATCAATTGCCAG
GCCAGTGAGAGTGTTTATAATAGCGACTGGTTAGCCTGGTATCAGCAGAAACCAGGGCAGCCTCCCAA
GCAACTGATCTATGCTGCATCCACTCTGGCATCTGGGGTCCCATCGCGCTTCAAAGGCAGTGGATCTGG
GACACAGTTCACTCTCACCATCAGCGATGTGGTGTGTGACGATGCTGCCACTTATTATTGTGCAGGATA
TAAAAGTAGTAGTACTGATGGGATTGCTTTCGGCGGAGGGACCGAGGTGGTGGTCAAA (SEQ ID NO: 8)

Clone 7 VL AA (CDRs underlined)
MDTRAPTQLLGLLLLWLPGATFAIVVTQTPSSKSVPVGGTVTINC<u>QASESVYNSDWLA</u>WYQQKPGQPPKQ
LIY<u>AASTLAS</u>GVPSRFKGSGSGTQFTLTISDVVCDDAATYYC<u>AGYKSSSTDGIA</u>FGGGTEVVVK (SEQ ID NO: 9)

Clone 7 LC AA (CDRs underlined)
MDTRAPTQLLGLLLLWLPGATFAIVVTQTPSSKSVPVGGTVTINC<u>QASESVYNSDWLA</u>WYQQKPGQPPKQ
LIY<u>AASTLAS</u>GVPSRFKGSGSGTQFTLTISDVVCDDAATYYC<u>AGYKSSSTDGIA</u>FGGGTEVVVKGDPVAPTVLI
FPPAADQVATGTVTIVCVANKYFPDVTVTWEVDGTTQTTGIENSKTPQNSADCTYNLSSTLTLTSTQYNSH
KEYTCKVTQGTTSVVQSFNRGDC (SEQ ID NO: 10)

Clone 7 VL CDR1 AA
QASESVYNSDWLA (SEQ ID NO: 11)

Clone 7 VL CDR2 AA
AASTLAS (SEQ ID NO: 12)

Clone 7 VL CDR3 AA
AGYKSSSTDGIA (SEQ ID NO: 13)

Figure 6

Clone 13 VH DNA
ATGGAGACTGGGCTGCGCTGGCTTCTCCTGGTCGCTGTGCTCAAAGGTGTCCAGTGTCAGGAGCAGCT
GGAGGAGTCCGGGGGAGACCTGGTCAAGCCTGGAGGAACCCTGACAGTCACCTGCAAAGCCTCTGGA
TTCTCCTTCAGTAACAATGGAATTTGCTGGGTCCGCCAGGCTCCAGGGAAGGGGCTGGAGTGGATCGG
ATGTCTTTATGTTGGTAGTAGTGATACCACTTACTACGCGAGCTGGGCGAAAGGCCGATTCACCATCTC
CAAAAGCTCGTCGACCACGGTGACTCTACAAATGACCAGTCTGACAGTCGCGGACACGGCCACCTATT
TCTGTACGATAAATCTCGGCTTGTGGGGCCCCGGCACCCTGGTCACCGTCTCCTCA (SEQ ID NO: 14)

Clone 13 VH AA (CDRs underlined)
METGLRWLLLVAVLKGVQCQEQLEESGGDLVKPGGTLTVTCKAS<u>GFSFSNN</u>GICWVRQAPGKGLEWIGCL
<u>YVGSSD</u>TTYYASWAKGRFTISKSSSTTVTLQMTSLTVADTATYFCT<u>INLGL</u>WGPGTLVTVSS (SEQ ID NO: 15)

Clone 13 HC AA (CDRs underlined)
METGLRWLLLVAVLKGVQCQEQLEESGGDLVKPGGTLTVTCKAS<u>GFSFSNN</u>GICWVRQAPGKGLEWIGCL
<u>YVGSSD</u>TTYYASWAKGRFTISKSSSTTVTLQMTSLTVADTATYFCT<u>INLGL</u>WGPGTLVTVSSGQPKAPSVFPL
APCCGDTPSSTVTLGCLVKGYLPEPVTVTWNSGTLTNGVRTFPSVRQSSGLYSLSSVVSVTSSSQPVTCNVA
HPATNTKVDKTVAPSTCSKPTCPPPELLGGPSVFIFPPKPKDTLMISRTPEVTCVVVDVSQDDPEVQFTWYI
NNEQVRTARPPLREQQFNSTIRVVSTLPIAHQDWLRGKEFKCKVHNKALPAPIEKTISKARGQPLEPKVYTM
GPPREELSSRSVSLTCMINGFYPSDISVEWEKNGKAEDNYKTTPAVLDSDGSYFLYSKLSVPTSEWQRGDVF
TCSVMHEALHNHYTQKSISRSPGK (SEQ ID NO: 16)

Clone 13 VH CDR1 AA
GFSFSNN (SEQ ID NO: 5)

Clone 13 VH CDR2 AA
YVGSSD (SEQ ID NO: 6)

Clone 13 VH CDR3 AA
NLGL (SEQ ID NO: 7)

Figure 7

Clone 13 VL DNA
ATGGACACGAGGGCCCCCACTCAGCTGCTGGGGCTCCTGCTGCTCTGGCTCCCAGGTGCCACACTTGC
CATCGTGGTGACCCAGACTCCATCTTCCAAGTCTGTCCCTGTGGGAGGCACAGTCACCATCAATTGCCA
GGCCAGTGAGAGTGTTTATAATAGCGACTGGTTAGCCTGGTATCAGCAGAAACCAGGGCAGCCTCCCA
AGCAACTGATCTATGCTGCATCCACTCTGGCATCTGGGGTCCCATCGCGCTTCAAAGGCAGTGGATCTG
GGACACAGTTCACTCTCACCATCAGCGATGTGGTGTGTGACGATGCTGCCACTTATTATTGTGCAGGAT
ATAAAAGTAGTAGTACTGATGGGATTGCTTTCGGCGGAGGGACCGAGGTGGTGGTCAAA (SEQ ID
NO: 17)

Clone 13 VL AA (CDRs underlined)
MDTRAPTQLLGLLLLWLPGATLAIVVTQTPSSKSVPVGGTVTINCQASESVYNSDWLAWYQQKPGQPPKQ
LIYAASTLASGVPSRFKGSGSGTQFTLTISDVVCDDAATYYCAGYKSSSTDGIAFGGGTEVVVK (SEQ ID NO:
18)

Clone 13 LC AA (CDRs underlined)
MDTRAPTQLLGLLLLWLPGATLAIVVTQTPSSKSVPVGGTVTINCQASESVYNSDWLAWYQQKPGQPPKQ
LIYAASTLASGVPSRFKGSGSGTQFTLTISDVVCDDAATYYCAGYKSSSTDGIAFGGGTEVVVKGDPVAPTVLI
FPPAADQVATGTVTIVCVANKYFPDVTVTWEVDGTTQTTGIENSKTPQNSADCTYNLSSTLTLTSTQYNSH
KEYTCKVTQGTTSVVQSFNRGDC (SEQ ID NO: 19)

Clone 13 VL CDR1 AA
QASESVYNSDWLA (SEQ ID NO: 11)

Clone 13 VL CDR2 AA
AASTLAS (SEQ ID NO: 12)

Clone 13 VL CDR3 AA
AGYKSSSTDGIA (SEQ ID NO: 13)

Figure 8

Clone 14-1 VH DNA
ATGGAGACTGGGCTGCGCTGGCTTCTCCTGGTCGCTGTGCTCAAAGGTGTCCAGTGTCAGGAGCAGCT
GGAGGAGTCCGGGGGAGGCCTGGTCAAGCCTGGGGCATCCCTGACACTCACCTGCAAAGCCTCTGGA
TTCGACTTCAGTATCAACTACTACATGTGCTGGGTCCGCCAGGCTCCAGGGAAGGGGTTGGAGTGGAT
CGCATGCATTTATACTGGTGATGATGACACTTTCTACGCGAGCTGGGCGAAAGGCCGGTTCACCATCTC
CAAAACCTCGTCGACCACGGTGACTCTACAACTGAACAGTCTGACAGCCGCGGACACGGCCACCTATTT
CTGTGTGAGAGGTCTATATAGTGGTAGTATTAATAACCTGTGGGGCCCAGGCACCCTGGTCACCGTCTC
CTCA
(SEQ ID NO: 20)

Clone 14-1 VH AA (CDRs underlined)
METGLRWLLLVAVLKGVQCQEQLEESGGGLVKPGASLTLTCKAS<u>GFDFSINY</u>YMCWVRQAPGKGLEWIAC
I<u>YTGDDD</u>TFYASWAKGRFTISKTSSTTVTLQLNSLTAADTATYFCVR<u>GLYSGSINNL</u>WGPGTLVTVSS
(SEQ ID NO: 21)

Clone 14-1 HC AA (CDRs underlined)
METGLRWLLLVAVLKGVQCQEQLEESGGGLVKPGASLTLTCKAS<u>GFDFSINY</u>YMCWVRQAPGKGLEWIAC
I<u>YTGDDD</u>TFYASWAKGRFTISKTSSTTVTLQLNSLTAADTATYFCVR<u>GLYSGSINNL</u>WGPGTLVTVSSGQPKA
PSVFPLAPCCGDTPSSTVTLGCLVKGYLPEPVTVTWNSGTLTNGVRTFPSVRQSSGLYSLSSVVSVTSSSQPV
TCNVAHPATNTKVDKTVAPSTCSKPTCPPPELLGGPSVFIFPPKPKDTLMISRTPEVTCVVVDVSQDDPEVQ
FTWYINNEQVRTARPPLREQQFNSTIRVVSTLPIAHQDWLRGKEFKCKVHNKALPAPIEKTISKARGQPLEP
KVYTMGPPREELSSRSVSLTCMINGFYPSDISVEWEKNGKAEDNYKTTPAVLDSDGSYFLYSKLSVPTSEWQ
RGDVFTCSVMHEALHNHYTQKSISRSPGK (SEQ ID NO: 22)

Clone 14-1 VH CDR1 AA
GFDFSINY (SEQ ID NO: 23)

Clone 14-1 VH CDR2 AA
YTGDD (SEQ ID NO: 24)

Clone 14-1 VH CDR3 AA
GLYSGSINNL (SEQ ID NO: 25)

Figure 9

Clone 14-1 VL DNA
ATGGACACGAGGGCCCCCACTCAGCTGCTGGGGCTCCTGCTGCTCTGGCTCCCAGATGCCAGATGTGC
GCTTGTGATGACCCAGACTCCATCCCCTGTGTCTGCAGCTGTGGGAGGCACAGTCACCATCAGTTGCCA
GGCCAGTCAGAGTGTTTATAACAACGACTACTTATCCTGGTATCAGCAGAAACCAGGGCAGCCTCCCA
AACTCCTGATCTATTATGCATCCACTCTGGCATCTGGGGTCTCATCGCGGTTCAAAGGCAGTGGATCTG
GGACACAGTTCACTCTCACCATCAGCGACGTGCAGTGTGACGATGCTGCCGCTTACTATTGTGCAGGC
GTTAAAGGTTATAGTAATGATAATAATGGTTTCGGCGGAGGGACCGAGGTGGTGGTCAAA (SEQ ID
NO: 26)

Clone 14-1 VL AA (CDRs underlined)
MDTRAPTQLLGLLLLWLPDARCALVMTQTPSPVSAAVGGTVTISC<u>QASQSVYNNDYLS</u>WYQQKPGQPPK
LLIY<u>YASTLAS</u>GVSSRFKGSGSGTQFTLTISDVQCDDAAAYYC<u>AGVKGYSNDNNG</u>FGGGTEVVVK (SEQ ID
NO: 27)

Clone 14-1 LC AA (CDRs underlined)
MDTRAPTQLLGLLLLWLPDARCALVMTQTPSPVSAAVGGTVTISC<u>QASQSVYNNDYLS</u>WYQQKPGQPPK
LLIY<u>YASTLAS</u>GVSSRFKGSGSGTQFTLTISDVQCDDAAAYYC<u>AGVKGYSNDNNG</u>FGGGTEVVVKGDPVAP
TVLIFPPAADQVATGTVTIVCVANKYFPDVTVTWEVDGTTQTTGIENSKTPQNSADCTYNLSSTLTLTSTQY
NSHKEYTCKVTQGTTSVVQSFNRGDC (SEQ ID NO:28)

Clone 14-1 VL CDR1 AA
QASQSVYNNDYLS (SEQ ID NO: 29)

Clone 14-1 VL CDR2 AA
YASTLAS (SEQ ID NO: 30)

Clone 14-1 VL CDR3 AA
AGVKGYSNDNNG (SEQ ID NO: 31)

Figure 10

Clone 14-7 VH DNA
ATGGAGACTGGGCTGCGCTGGCTTCTCCTGGTCGCTGTGCTCAAAGGTGTCCAATGTCAGTCGCTGGA
GGAGTCCGGGGGAGGCCTGGTCAAGCCTGGGGCATCCCTGACACTCACCTGCAAAGCCTCTGGATTCG
ACTTCAGTATCAACTACTACATGTGCTGGGTCCGCCAGGCTCCAGGGAAGGGGTTGGAGTGGATCGCA
TGCATTTATACTGGTGATGATGACACTTTCTACGCGAGCTGGGCGAAAGGCCGGTTCACCATCTCCAAA
ACCTCGTCGACCACGGTGACTCTACAACTGAACAGTCTGACAGCCGCGGACACGGCCACCTATTTCTGT
GTGAGAGGTCTATATAGTGGTAGTATTAATAACCTGTGGGGCCCAGGCACCCTGGTCACCGTCTCCTCA
(SEQ ID NO: 32)

Clone 14-7 VH AA (CDRs underlined)
METGLRWLLLVAVLKGVQCQSLEESGGGLVKPGASLTLTCKAS<u>GFDFSINYY</u>MCWVRQAPGKGLEWIAC<u>IY
TGDDD</u>TFYASWAKGRFTISKTSSTTVTLQLNSLTAADTATYFCVR<u>GLYSGSINNL</u>WGPGTLVTVSS (SEQ ID
NO: 33)

Clone 14-7 HC AA (CDRs underlined)
METGLRWLLLVAVLKGVQCQSLEESGGGLVKPGASLTLTCKAS<u>GFDFSINYY</u>MCWVRQAPGKGLEWIAC<u>IY
TGDDD</u>TFYASWAKGRFTISKTSSTTVTLQLNSLTAADTATYFCVR<u>GLYSGSINNL</u>WGPGTLVTVSSGQPKAP
SVFPLAPCCGDTPSSTVTLGCLVKGYLPEPVTVTWNSGTLTNGVRTFPSVRQSSGLYSLSSVVSVTSSSQPVT
CNVAHPATNTKVDKTVAPSTCSKPTCPPPELLGGPSVFIFPPKPKDTLMISRTPEVTCVVVDVSQDDPEVQF
TWYINNEQVRTARPPLREQQFNSTIRVVSTLPIAHQDWLRGKEFKCKVHNKALPAPIEKTISKARGQPLEPK
VYTMGPPREELSSRSVSLTCMINGFYPSDISVEWEKNGKAEDNYKTTPAVLDSDGSYFLYSKLSVPTSEWQR
GDVFTCSVMHEALHNHYTQKSISRSPGK (SEQ ID NO: 34)

Clone 14-7 VH CDR1 AA
GFDFSINY (SEQ ID NO: 23)

Clone 14-7 VH CDR2 AA
YTGDD (SEQ ID NO: 24)

Clone 14-7 VH CDR3 AA
GLYSGSINNL (SEQ ID NO: 25)

Figure 11

Clone 14-7 VL DNA
ATGGACACGAGGGCCCCCACTCAGCTGCTGGGGCTCCTGCTGCTCTGGCTCCCAGATGCCAGATGTGC
GCTTGTGATGACCCAGACTCCATCCCTGTGTCTGCAGCTGTGGGAGGCACAGTCACCATCAGTTGCCA
GGCCAGTCAGAGTGTTTATAACAACGACTACTTATCCTGGTATCAGCAGAAACCAGGGCAGCCTCCCA
AACTCCTGATCTATTATGCATCCACTCTGGCATCTGGGGTCTCATCGCGGTTCAAAGGCAGTGGATCTG
GGACACAGTTCACTCTCACCATCAGCGACGTGCAGTGTGACGATGCTGCCGCTTACTATTGTGCAGGC
GTTAAAGGTTATAGTAATGATAATAATGGTTTCGGCGGAGGGACCGAGGTGGTGGTCAAA (SEQ ID
NO: 35)

Clone 14-7 VL AA (CDRs underlined)
MDTRAPTQLLGLLLLWLPDARCALVMTQTPSPVSAAVGGTVTIS<u>CQASQSVYNNDYLS</u>WYQQKPGQPPK
LLIY<u>YASTLAS</u>GVSSRFKGSGSGTQFTLTISDVQCDDAAAYYC<u>AGVKGYSNDNNG</u>FGGGTEVVVK (SEQ ID
NO: 36)

Clone 14-7 LC AA (CDRs underlined)
MDTRAPTQLLGLLLLWLPDARCALVMTQTPSPVSAAVGGTVTIS<u>CQASQSVYNNDYLS</u>WYQQKPGQPPK
LLIY<u>YASTLAS</u>GVSSRFKGSGSGTQFTLTISDVQCDDAAAYYC<u>AGVKGYSNDNNG</u>FGGGTEVVVKGDPVAP
TVLIFPPAADQVATGTVTIVCVANKYFPDVTVTWEVDGTTQTTGIENSKTPQNSADCTYNLSSTLTLTSTQY
NSHKEYTCKVTQGTTSVVQSFNRGDC (SEQ ID NO: 37)

Clone 14-7 VL CDR1 AA
QASQSVYNNDYLS (SEQ ID NO: 29)

Clone 14-7 VL CDR2 AA
YASTLAS (SEQ ID NO: 30)

Clone 14-7 VL CDR3 AA
AGVKGYSNDNNG (SEQ ID NO: 31)

Figure 12

Clone 15 VH DNA
ATGGAGACTGGGCTGCGCTGGCTTCTCCTGGTCGCTGTGCTCAAAGGGGTCCAGTGTCAGTCGTTGGA
GGAGTCCGGGGGAGACCTGGTCAAGCCTGGGGCATCCCTGACACTCACCTGCACAGCCTCTGGATTCT
CCTTCACGAGCAACTACTACATGTGCTGGGTCCGCCAGGCTCCAGGGAAGGGGCTGGAGTGGGTCGC
GTGCATTTTTCTTGGTAGTAGTGGTAACACTGTCTACGCGAACTGGGCGAAAGGCCGATTCACCATCTC
CAAAACCTCGTCGACCACGGTGACTCTGCAAATGACCAGTCTGACAGTCGCGGACACGGCCACCTATTT
CTGTGCGAGAGACTATGTTAATGGTTATGACTACTTTAACTTGTGGGGCCCAGGCACCTTGGTCACCGT
CTCCTCA (SEQ ID NO: 38)

Clone 15 VH AA (CDRs underlined)
METGLRWLLLVAVLKGVQCQSLEESGGDLVKPGASLTLTCTAS<u>GFSFTSNY</u>YMCWVRQAPGKGLEWVACI
<u>FLGSSG</u>NTVYANWAKGRFTISKTSSTTVTLQMTSLTVADTATYFCAR<u>DYVNGYDYFNL</u>WGPGTLVTVSS
(SEQ ID NO: 39)

Clone 15 HC AA (CDRs underlined)
METGLRWLLLVAVLKGVQCQSLEESGGDLVKPGASLTLTCTAS<u>GFSFTSNY</u>YMCWVRQAPGKGLEWVACI
<u>FLGSSG</u>NTVYANWAKGRFTISKTSSTTVTLQMTSLTVADTATYFCAR<u>DYVNGYDYFNL</u>WGPGTLVTVSSGQ
PKAPSVFPLAPCCGDTPSSTVTLGCLVKGYLPEPVTVTWNSGTLTNGVRTFPSVRQSSGLYSLSSVVSVTSSS
QPVTCNVAHPATNTKVDKTVAPSTCSKPTCPPPELLGGPSVFIFPPKPKDTLMISRTPEVTCVVVDVSQDDP
EVQFTWYINNEQVRTARPPLREQQFNSTIRVVSTLPIAHQDWLRGKEFKCKVHNKALPAPIEKTISKARGQP
LEPKVYTMGPPREELSSRSVSLTCMINGFYPSDISVEWEKNGKAEDNYKTTPAVLDSDGSYFLYSKLSVPTSE
WQRGDVFTCSVMHEALHNHYTQKSISRSPGK (SEQ ID NO: 40)

Clone 15 VH CDR1 AA
GFSFTSNY (SEQ ID NO: 41)

Clone 15 VH CDR2 AA
FLGSSG (SEQ ID NO: 42)

Clone 15 VH CDR3 AA
DYVNGYDYFNL (SEQ ID NO: 43)

Figure 13

Clone 15 VL DNA
ATGGACACGAGGGCCCCCACTCAGCTGCTGGGGCTCCTGCTGCTCTGGCTCCCAGGTGCCACATTTGCC
CAAGTGCTGACCCAGACTGCATCCCCCGTGTCTGCGGCTGTTGGAGGCACAGTCACCATCAATTGCCA
GTCCAGTCAGAGTGTTTATAATAAGAACTTAGCCTGGTATCAGCAGAAACCAGGGCAGCCTCCCAAAG
GCCTGATCTATTCTACATCGACTCTAGATTCTGGGGTCCCATCGCGGTTCAGCGGCAGTGGATCTGGGA
CACAGTTCACTCTCACCATCAGCGACGTGCAGTGTGACGATGCTGCCACTTACTACTGTCTAGGCAGTT
ATGATTGTAGTAGTGCTGATTGTAATGCTTTCGGCGGAGGGACCGAGGTGGTGGTCAAA (SEQ ID NO: 44)

Clone 15 VL AA (CDRs underlined)
MDTRAPTQLLGLLLLWLPGATFAQVLTQTASPVSAAVGGTVTINC<u>QSSQSVYNKNLA</u>WYQQKPGQPPKG
LIY<u>STSTLDS</u>GVPSRFSGSGSGTQFTLTISDVQCDDAATYYC<u>LGSYDCSSADCNA</u>FGGGTEVVVK (SEQ ID NO: 45)

Clone 15 LC AA (CDRs underlined)
MDTRAPTQLLGLLLLWLPGATFAQVLTQTASPVSAAVGGTVTINC<u>QSSQSVYNKNLA</u>WYQQKPGQPPKG
LIY<u>STSTLDS</u>GVPSRFSGSGSGTQFTLTISDVQCDDAATYYC<u>LGSYDCSSADCNA</u>FGGGTEVVVKGDPVAPT
VLIFPPAADQVATGTVTIVCVANKYFPDVTVTWEVDGTTQTTGIENSKTPQNSADCTYNLSSTLTLTSTQYN
SHKEYTCKVTQGTTSVVQSFNRGDC (SEQ ID NO: 46)

Clone 15 VL CDR1 AA
QSSQSVYNKNLA (SEQ ID NO: 47)

Clone 15 VL CDR2 AA
STSTLDS (SEQ ID NO: 48)

Clone 15 VL CDR3 AA
LGSYDCSSADCNA (SEQ ID NO: 49)

Figure 14

Clone 17 VH DNA
ATGGAGACTGGGCTGCGCTGGCTTCTCCTGGTCGCTGTGCTCAAAGGTGTCCAATGTCAGTCGCTGGA
GGAGTCCGGGGGAGGCCTGGTCAAGCCTGGGGCATCCCTGACACTCACCTGCACAGCCTCTGGATTCT
CCTTCAGTGACAGTTGGTACTTGTGTTGGGTCCGCCAGGCTCCAGGGAAGGGGCTGGAGTGGATCGC
ATGCATTTATACTGGTGATGGTGACACTTATTACGCGACCTGGGCGAAAGGCCGATTCACCATCTCCAA
GACCTCGTCGACCACAGTGACTCTACAAATGACCAGTCTGACAGCCGCGGACACGGCCACCTATTTCTG
TGCGAGGGGTGCCCAATTTTACTTGTGGGGCCAAGGCACCCTGGTCACCGTCTCCTCA (SEQ ID NO: 50)

Clone 17 VH AA (CDRs underlined)
METGLRWLLLVAVLKGVQCQSLEESGGGLVKPGASLTLTCTAS<u>GFSFSDSW</u>YLCWVRQAPGKGLEWIACI<u>Y</u>
<u>TGDG</u>DTYYATWAKGRFTISKTSSTTVTLQMTSLTAADTATYFCAR<u>GAQFYL</u>WGQGTLVTVSS (SEQ ID NO: 51)

Clone 17 HC AA (CDRs underlined)
METGLRWLLLVAVLKGVQCQSLEESGGGLVKPGASLTLTCTAS<u>GFSFSDSW</u>YLCWVRQAPGKGLEWIACI<u>Y</u>
<u>TGDG</u>DTYYATWAKGRFTISKTSSTTVTLQMTSLTAADTATYFCAR<u>GAQFYL</u>WGQGTLVTVSSGQPKAPSVF
PLAPCCGDTPSSTVTLGCLVKGYLPEPVTVTWNSGTLTNGVRTFPSVRQSSGLYSLSSVVSVTSSSQPVTCNV
AHPATNTKVDKTVAPSTCSKPTCPPPELLGGPSVFIFPPKPKDTLMISRTPEVTCVVVDVSQDDPEVQFTWYI
NNEQVRTARPPLREQQFNSTIRVVSTLPIAHQDWLRGKEFKCKVHNKALPAPIEKTISKARGQPLEPKVYTM
GPPREELSSRSVSLTCMINGFYPSDISVEWEKNGKAEDNYKTTPAVLDSDGSYFLYSKLSVPTSEWQRGDVF
TCSVMHEALHNHYTQKSISRSPGK (SEQ ID NO: 52)

Clone 17 VH CDR1 AA
GFSFSDSW (SEQ ID NO: 53)

Clone 17 VH CDR2 AA
YTGDG (SEQ ID NO: 54)

Clone 17 VH CDR3 AA
GAQFYL (SEQ ID NO: 55)

Figure 15

Clone 17 VL DNA
ATGGACACGAGGGCCCCCACTCAGCTGCTGGGGCTCCTGCTGCTCTGGCTCCCAGGTGCCACATTTGCC
CAGGTGCTGACCCAGACTCCATCCTCCGTGTCTGCAGCTGTGGGAGGCACAGTCACCATCAATTGCCA
GTCCAGTCAGAGTGTTTATGCCAACACCTACTTATCCTGGTATCAGCAGAAACCAGGGCAGCCTCCCAA
GCAACTGATCTATTCTGCATCCAGTCTGGCATCTGGGGTCCCACCGCGGTTCAAAGGCAGTGGATCTG
GGACACAGTTCGCTCTCACCATCAGCGACGTGCAGTGTGACGATGCTGCCACTTACTACTGTCTAGGCA
GATATAGTTGTGGTCTTGCTGATTGTGCTGCTTTCGGCGGAGGGACCGAGGTGGTGGTCAAA (SEQ ID
NO:56)

Clone 17 VL AA (CDRs underlined)
MDTRAPTQLLGLLLLWLPGATFAQVLTQTPSSVSAAVGGTVTINCQSSQSVYANTYLSWYQQKPGQPPKQ
LIYSASSLASGVPPRFKGSGSGTQFALTISDVQCDDAATYYCLGRYSCGLADCAAFGGGTEVVVK (SEQ ID
NO: 57)

Clone 17 LC AA (CDRs underlined)
MDTRAPTQLLGLLLLWLPGATFAQVLTQTPSSVSAAVGGTVTINCQSSQSVYANTYLSWYQQKPGQPPKQ
LIYSASSLASGVPPRFKGSGSGTQFALTISDVQCDDAATYYCLGRYSCGLADCAAFGGGTEVVVKGDPVAPT
VLIFPPAADQVATGTVTIVCVANKYFPDVTVTWEVDGTTQTTGIENSKTPQNSADCTYNLSSTLTLTSTQYN
SHKEYTCKVTQGTTSVVQSFNRGDC (SEQ ID NO: 58)

Clone 17 VL CDR1 AA
QSSQSVYANTYLS (SEQ ID NO: 59)

Clone 17 VL CDR2 AA
SASSLAS (SEQ ID NO: 60)

Clone 17 VL CDR3 AA
LGRYSCGLADCAA (SEQ ID NO: 61)

Figure 16

Table 1. CDR Table (Kabat)

| Sequence | CDR1 | SEQ ID NO. | CDR2 | SEQ ID NO. | CDR3 | SEQ ID NO. |
|---|---|---|---|---|---|---|
| 7_VL | QASESVYNSDWLA | 11 | AASTLAS | 12 | AGYKSSSTDGIA | 13 |
| 13_VL | QASESVYNSDWLA | 11 | AASTLAS | 12 | AGYKSSSTDGIA | 13 |
| 14-1_VL | QASQSVYNNDYLS | 29 | YASTLAS | 30 | AGVKGYSNDNNG | 31 |
| 14-7_VL | QASQSVYNNDYLS | 29 | YASTLAS | 30 | AGVKGYSNDNNG | 31 |
| 15_VL | QSSQSVYNKNLA | 47 | STSTLDS | 48 | LGSYDCSSADCNA | 49 |
| 17_VL | QSSQSVYANTYLS | 59 | SASSLAS | 60 | LGRYSCGLADCAA | 61 |
| 7_VH | NNGIC | 62 | CLYVGSSDTTYYASWAK | 63 | NLGL | 7 |
| 13_VH | NNGIC | 62 | CLYVGSSDTTYYASWAK | 63 | NLGL | 7 |
| 14-1_VH | INYYMC | 64 | CIYTGDDDTFYASWAK | 65 | GLYSGSINNL | 25 |
| 14-7_VH | INYYMC | 64 | CIYTGDDDTFYASWAK | 65 | GLYSGSINNL | 25 |
| 15_VH | SNYYMC | 66 | CIFLGSSGNTVYANWAK | 67 | DYVNGYDYFNL | 43 |
| 17_VH | DSWYLC | 68 | CIYTGDGDTYYATWAK | 69 | GAQFYL | 55 |

Figure 19

Table 2. CDR Table (Chothia)

| Sequence | CDR1 | SEQ ID NO | CDR2 | SEQ ID NO | CDR3 | SEQ ID NO. |
|---|---|---|---|---|---|---|
| 7_VL | QASESVYNSDWLA | 11 | AASTLAS | 12 | AGYKSSSTDGIA | 13 |
| 13_VL | QASESVYNSDWLA | 11 | AASTLAS | 12 | AGYKSSSTDGIA | 13 |
| 14-1_VL | QASQSVYNNDYLS | 29 | YASTLAS | 30 | AGVKGYSNDNNG | 31 |
| 14-7_VL | QASQSVYNNDYLS | 29 | YASTLAS | 30 | AGVKGYSNDNNG | 31 |
| 15_VL | QSSQSVYNKNLA | 47 | STSTLDS | 48 | LGSYDCSSADCNA | 49 |
| 17_VL | QSSQSVYANTYLS | 59 | SASSLAS | 60 | LGRYSCGLADCAA | 61 |
| 7_VH | GFSFSNN | 5 | YVGSSD | 6 | NLGL | 7 |
| 13_VH | GFSFSNN | 5 | YVGSSD | 6 | NLGL | 7 |
| 14-1_VH | GFDFSINY | 23 | YTGDD | 24 | GLYSGSINNL | 25 |
| 14-7_VH | GFDFSINY | 23 | YTGDD | 24 | GLYSGSINNL | 25 |
| 15_VH | GFSFTSNY | 41 | FLGSSG | 42 | DYVNGYDYFNL | 43 |
| 17_VH | GFSFSDSW | 53 | YTGDG | 54 | GAQFYL | 55 |

Figure 20

Table 3. CDR Table (IMGT)

| Sequence | CDR1 | SEQ ID NO. | CDR2 | SEQ ID NO. | CDR3 | SEQ ID NO. |
|---|---|---|---|---|---|---|
| 7_VL | QASESVYNSDWLA | 11 | AASTLAS | 12 | AGYKSSSTDGIA | 13 |
| 13_VL | QASESVYNSDWLA | 11 | AASTLAS | 12 | AGYKSSSTDGIA | 13 |
| 14-1_VL | QASQSVYNNDYLS | 29 | YASTLAS | 30 | AGVKGYSNDNNG | 31 |
| 14-7_VL | QASQSVYNNDYLS | 29 | YASTLAS | 30 | AGVKGYSNDNNG | 31 |
| 15_VL | QSSQSVYNKNLA | 47 | STSTLDS | 48 | LGSYDCSSADCNA | 49 |
| 17_VL | QSSQSVYANTYLS | 59 | SASSLAS | 60 | LGRYSCGLADCAA | 61 |
| 7_VH | GFSFSNNGIC | 70 | CLYVGSSDTTYYASWAK | 63 | NLGL | 7 |
| 13_VH | GFSFSNNGIC | 70 | CLYVGSSDTTYYASWAK | 63 | NLGL | 7 |
| 14-1_VH | GFDFSINYYMC | 71 | CIYTGDDDTFYASWAK | 65 | GLYSGSINNL | 25 |
| 14-7_VH | GFDFSINYYMC | 71 | CIYTGDDDTFYASWAK | 65 | GLYSGSINNL | 25 |
| 15_VH | GFSFTSNYYMC | 72 | CIFLGSSGNTVYANWAK | 67 | DYVNGYDYFNL | 43 |
| 17_VH | GFSFSDSWYLC | 73 | CIYTGDGDTYYATWAK | 69 | GAQFYL | 55 |

Figure 21

SEQUENCE LISTING

<160> NUMBER OF SEQ ID NOS: 82

<210> SEQ ID NO 1
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265

<210> SEQ ID NO 2
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggagactg ggctgcgctg gcttctcctg gtcgctgtgc tcaaaggtgt ccagtgtcag      60
gagcagctgg aggagtccgg gggagacctg gtcaagcctg aggaaccct gacagtcacc      120

```
tgcaaagcct ctggattctc cttcagtaac aatggaattt gctgggtccg ccaggctcca    180 gggaagggc tggagtggat cggatgtctt tatgttggta gtagtgatac cacttactac    240
gcgagctggg cgaaaggccg attcaccatc tccaaaagct cgtcgaccac ggtgactcta    300
caaatgacca gtctgacagt cgcggacacg gccacctatt tctgtacgat aaatctcggc    360
ttgtggggcc ccggcaccct ggtcaccgtc tcctca                              396
```

```
<210> SEQ ID NO 3
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Gly Gly Thr Leu Thr Val Thr Cys Lys Ala Ser Gly Phe Ser Phe
        35                  40                  45

Ser Asn Asn Gly Ile Cys Trp Val Arg Gln Ala Pro Gly Lys Gly Leu
    50                  55                  60

Glu Trp Ile Gly Cys Leu Tyr Val Gly Ser Ser Asp Thr Thr Tyr Tyr
65                  70                  75                  80

Ala Ser Trp Ala Lys Gly Arg Phe Thr Ile Ser Lys Ser Ser Ser Thr
                85                  90                  95

Thr Val Thr Leu Gln Met Thr Ser Leu Thr Val Ala Asp Thr Ala Thr
            100                 105                 110

Tyr Phe Cys Thr Ile Asn Leu Gly Leu Trp Gly Pro Gly Thr Leu Val
        115                 120                 125

Thr Val Ser Ser
    130

```
<210> SEQ ID NO 4
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Gly Gly Thr Leu Thr Val Thr Cys Lys Ala Ser Gly Phe Ser Phe
        35                  40                  45

Ser Asn Asn Gly Ile Cys Trp Val Arg Gln Ala Pro Gly Lys Gly Leu
    50                  55                  60

Glu Trp Ile Gly Cys Leu Tyr Val Gly Ser Ser Asp Thr Thr Tyr Tyr
65                  70                  75                  80

Ala Ser Trp Ala Lys Gly Arg Phe Thr Ile Ser Lys Ser Ser Ser Thr
                85                  90                  95

Thr Val Thr Leu Gln Met Thr Ser Leu Thr Val Ala Asp Thr Ala Thr
            100                 105                 110

```
Tyr Phe Cys Thr Ile Asn Leu Gly Leu Trp Gly Pro Gly Thr Leu Val
            115                 120                 125

Thr Val Ser Ser Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Ser Val Thr Ser Ser Ser Gln
            195                 200                 205

Pro Val Thr Cys Asn Val Ala His Pro Ala Thr Asn Thr Lys Val Asp
            210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
            275                 280                 285

Asn Glu Gln Val Arg Thr Ala Arg Pro Pro Leu Arg Glu Gln Gln Phe
            290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
            355                 360                 365

Arg Ser Val Ser Leu Thr Cys Met Ile Asn Gly Phe Tyr Pro Ser Asp
370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
            435                 440                 445

Ile Ser Arg Ser Pro Gly Lys
450                 455

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Ser Phe Ser Asn Asn
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Val Gly Ser Ser Asp
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Leu Gly Leu
1

<210> SEQ ID NO 8
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggacacga gggcccccac tcagctgctg gggctcctgc tgctctggct cccaggtgcc      60
acatttgcca tcgtggtgac ccagactcca tcttccaagt ctgtccctgt gggaggcaca     120
gtcaccatca attgccaggc cagtgagagt gtttataata gcgactggtt agcctggtat     180
cagcagaaac cagggcagcc tcccaagcaa ctgatctatg ctgcatccac tctggcatct     240
ggggtcccat cgcgcttcaa aggcagtgga tctgggacag agttcactct caccatcagc     300
gatgtggtgt gtgacgatgc tgccacttat tattgtgcag gatataaaag tagtagtact     360
gatgggattg ctttcggcgg agggaccgag gtggtggtca aa                        402

<210> SEQ ID NO 9
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Thr Arg Ala Pro Thr Gln Leu Leu Gly Leu Leu Leu Leu Trp
1               5                  10                  15

Leu Pro Gly Ala Thr Phe Ala Ile Val Val Thr Gln Thr Pro Ser Ser
            20                  25                  30

Lys Ser Val Pro Val Gly Gly Thr Val Thr Ile Asn Cys Gln Ala Ser
        35                  40                  45

Glu Ser Val Tyr Asn Ser Asp Trp Leu Ala Trp Tyr Gln Gln Lys Pro
    50                  55                  60

Gly Gln Pro Pro Lys Gln Leu Ile Tyr Ala Ala Ser Thr Leu Ala Ser

```
            65                  70                  75                  80
Gly Val Pro Ser Arg Phe Lys Gly Ser Gly Ser Gly Thr Gln Phe Thr
                85                  90                  95

Leu Thr Ile Ser Asp Val Val Cys Asp Asp Ala Ala Thr Tyr Tyr Cys
            100                 105                 110

Ala Gly Tyr Lys Ser Ser Ser Thr Asp Gly Ile Ala Phe Gly Gly Gly
        115                 120                 125

Thr Glu Val Val Val Lys
    130

<210> SEQ ID NO 10
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Thr Arg Ala Pro Thr Gln Leu Leu Gly Leu Leu Leu Leu Trp
1               5                   10                  15

Leu Pro Gly Ala Thr Phe Ala Ile Val Val Thr Gln Thr Pro Ser Ser
            20                  25                  30

Lys Ser Val Pro Val Gly Gly Thr Val Thr Ile Asn Cys Gln Ala Ser
        35                  40                  45

Glu Ser Val Tyr Asn Ser Asp Trp Leu Ala Trp Tyr Gln Gln Lys Pro
    50                  55                  60

Gly Gln Pro Pro Lys Gln Leu Ile Tyr Ala Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Val Cys Asp Asp Ala Ala Thr Tyr Tyr Cys
            100                 105                 110

Ala Gly Tyr Lys Ser Ser Ser Thr Asp Gly Ile Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 11

Gln Ala Ser Glu Ser Val Tyr Asn Ser Asp Trp Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Ser Thr Leu Ala Ser
1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gly Tyr Lys Ser Ser Ser Thr Asp Gly Ile Ala
1               5                   10

<210> SEQ ID NO 14
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggagactg ggctgcgctg gcttctcctg gtcgctgtgc tcaaaggtgt ccagtgtcag      60
gagcagctgg aggagtccgg gggagacctg gtcaagcctg aggaaccct gacagtcacc     120 tgcaaagcct ctggattctc cttcagtaac aatggaattt gctgggtccg ccaggctcca    180
gggaaggggc tggagtggat cggatgtctt tatgttggta gtagtgatac cacttactac    240
gcgagctggg cgaaaggccg attcaccatc tccaaaagct cgtcgaccac ggtgactcta    300
caaatgacca gtctgacagt cgcggacacg gccacctatt tctgtacgat aaatctcggc    360
ttgtggggcc ccggcaccct ggtcaccgtc tcctca                              396

<210> SEQ ID NO 15
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
                20                  25                  30

Pro Gly Gly Thr Leu Thr Val Thr Cys Lys Ala Ser Gly Phe Ser Phe
            35                  40                  45

Ser Asn Asn Gly Ile Cys Trp Val Arg Gln Ala Pro Gly Lys Gly Leu

```
            50                  55                  60
Glu Trp Ile Gly Cys Leu Tyr Val Gly Ser Ser Asp Thr Thr Tyr Tyr
 65                  70                  75                  80

Ala Ser Trp Ala Lys Gly Arg Phe Thr Ile Ser Lys Ser Ser Ser Thr
                 85                  90                  95

Thr Val Thr Leu Gln Met Thr Ser Leu Thr Val Ala Asp Thr Ala Thr
            100                 105                 110

Tyr Phe Cys Thr Ile Asn Leu Gly Leu Trp Gly Pro Gly Thr Leu Val
            115                 120                 125

Thr Val Ser Ser
            130

<210> SEQ ID NO 16
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Glu Thr Gly Leu Arg Trp Leu Leu Leu Val Ala Val Leu Lys Gly
  1               5                  10                  15

Val Gln Cys Gln Glu Gln Leu Glu Glu Ser Gly Gly Asp Leu Val Lys
             20                  25                  30

Pro Gly Gly Thr Leu Thr Val Thr Cys Lys Ala Ser Gly Phe Ser Phe
         35                  40                  45

Ser Asn Asn Gly Ile Cys Trp Val Arg Gln Ala Pro Gly Lys Gly Leu
 50                  55                  60

Glu Trp Ile Gly Cys Leu Tyr Val Gly Ser Ser Asp Thr Thr Tyr Tyr
 65                  70                  75                  80

Ala Ser Trp Ala Lys Gly Arg Phe Thr Ile Ser Lys Ser Ser Ser Thr
                 85                  90                  95

Thr Val Thr Leu Gln Met Thr Ser Leu Thr Val Ala Asp Thr Ala Thr
            100                 105                 110

Tyr Phe Cys Thr Ile Asn Leu Gly Leu Trp Gly Pro Gly Thr Leu Val
            115                 120                 125

Thr Val Ser Ser Gly Gln Pro Lys Ala Pro Ser Val Phe Pro Leu Ala
            130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
            195                 200                 205

Pro Val Thr Cys Asn Val Ala His Pro Ala Thr Asn Thr Lys Val Asp
        210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270
```

-continued

```
Asp Val Ser Gln Asp Asp Pro Glu Val Gln Phe Thr Trp Tyr Ile Asn
            275                 280                 285

Asn Glu Gln Val Arg Thr Ala Arg Pro Pro Leu Arg Glu Gln Gln Phe
        290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
    450                 455

<210> SEQ ID NO 17
<211> LENGTH: 401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggacacga gggcccccac tcagctgctg gggctcctgc tgctctggct cccaggtgcc      60
acacttgcca tcgtggtgac ccagactcca tcttccaagt ctgtccctgt ggaggcaca     120 gtcaccatca attgccaggc cagtgagagt gtttataata gcgactggtt agcctggtat    180
cagcagaaac cagggcagcc tcccaagcaa ctgatctatg ctgcatccac tctggcatct    240
ggggtcccat cgcgcttcaa aggcagtgga tctgggacac agttcactct caccatcagc    300
gatgtggtgt gtgacgatgc tgccacttat tattgtgcag atataaaag tagtagtact    360 gatgggattg ctttcggcgg agggaccgag gtggtggtca a                        401

<210> SEQ ID NO 18
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Thr Arg Ala Pro Thr Gln Leu Leu Gly Leu Leu Leu Leu Trp
1               5                   10                  15

Leu Pro Gly Ala Thr Leu Ala Ile Val Val Thr Gln Thr Pro Ser Ser
            20                  25                  30

Lys Ser Val Pro Val Gly Gly Thr Val Thr Ile Asn Cys Gln Ala Ser
```

```
                35                  40                  45
Glu Ser Val Tyr Asn Ser Asp Trp Leu Ala Trp Tyr Gln Gln Lys Pro
 50                  55                  60

Gly Gln Pro Pro Lys Gln Leu Ile Tyr Ala Ala Ser Thr Leu Ala Ser
 65                  70                  75                  80

Gly Val Pro Ser Arg Phe Lys Gly Ser Gly Ser Gly Thr Gln Phe Thr
                 85                  90                  95

Leu Thr Ile Ser Asp Val Val Cys Asp Asp Ala Ala Thr Tyr Tyr Cys
                100                 105                 110

Ala Gly Tyr Lys Ser Ser Ser Thr Asp Gly Ile Ala Phe Gly Gly Gly
                115                 120                 125

Thr Glu Val Val Val Lys
                130

<210> SEQ ID NO 19
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Thr Arg Ala Pro Thr Gln Leu Leu Gly Leu Leu Leu Leu Trp
  1               5                  10                  15

Leu Pro Gly Ala Thr Leu Ala Ile Val Val Thr Gln Thr Pro Ser Ser
                 20                  25                  30

Lys Ser Val Pro Val Gly Gly Thr Val Thr Ile Asn Cys Gln Ala Ser
                 35                  40                  45

Glu Ser Val Tyr Asn Ser Asp Trp Leu Ala Trp Tyr Gln Gln Lys Pro
 50                  55                  60

Gly Gln Pro Pro Lys Gln Leu Ile Tyr Ala Ala Ser Thr Leu Ala Ser
 65                  70                  75                  80

Gly Val Pro Ser Arg Phe Lys Gly Ser Gly Ser Gly Thr Gln Phe Thr
                 85                  90                  95

Leu Thr Ile Ser Asp Val Val Cys Asp Asp Ala Ala Thr Tyr Tyr Cys
                100                 105                 110

Ala Gly Tyr Lys Ser Ser Ser Thr Asp Gly Ile Ala Phe Gly Gly Gly
                115                 120                 125

Thr Glu Val Val Val Lys Gly Asp Pro Val Ala Pro Thr Val Leu Ile
                130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
                180                 185                 190

Asn Ser Ala Asp Cys Thr Tyr Asn Leu Ser Ser Thr Leu Thr Leu Thr
                195                 200                 205

Ser Thr Gln Tyr Asn Ser His Lys Glu Tyr Thr Cys Lys Val Thr Gln
                210                 215                 220

Gly Thr Thr Ser Val Val Gln Ser Phe Asn Arg Gly Asp Cys
225                 230                 235

<210> SEQ ID NO 20
<211> LENGTH: 414
```

<210> SEQ ID NO 21
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
atggagactg ggctgcgctg gcttctcctg gtcgctgtgc tcaaaggtgt ccagtgtcag      60
gagcagctgg aggagtccgg gggaggcctg gtcaagcctg gggcatccct gacactcacc     120
tgcaaagcct ctggattcga cttcagtatc aactactaca tgtgctgggt ccgccaggct     180
ccagggaagg ggttggagtg gatcgcatgc atttatactg gtgatgatga cactttctac     240
gcgagctggg cgaaaggccg gttcaccatc tccaaaacct cgtcgaccac ggtgactcta     300
caactgaaca gtctgacagc cgcggacacg gccacctatt tctgtgtgag aggtctatat     360
agtggtagta ttaataacct gtggggccca ggcaccctgg tcaccgtctc ctca           414
```

<210> SEQ ID NO 21
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Lys
            20                  25                  30

Pro Gly Ala Ser Leu Thr Leu Thr Cys Lys Ala Ser Gly Phe Asp Phe
        35                  40                  45

Ser Ile Asn Tyr Tyr Met Cys Trp Val Arg Gln Ala Pro Gly Lys Gly
    50                  55                  60

Leu Glu Trp Ile Ala Cys Ile Tyr Thr Gly Asp Asp Asp Thr Phe Tyr
65                  70                  75                  80

Ala Ser Trp Ala Lys Gly Arg Phe Thr Ile Ser Lys Thr Ser Ser Thr
                85                  90                  95

Thr Val Thr Leu Gln Leu Asn Ser Leu Thr Ala Ala Asp Thr Ala Thr
            100                 105                 110

Tyr Phe Cys Val Arg Gly Leu Tyr Ser Gly Ser Ile Asn Asn Leu Trp
        115                 120                 125

Gly Pro Gly Thr Leu Val Thr Val Ser Ser
    130                 135
```

<210> SEQ ID NO 22
<211> LENGTH: 461
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Lys
            20                  25                  30

Pro Gly Ala Ser Leu Thr Leu Thr Cys Lys Ala Ser Gly Phe Asp Phe
        35                  40                  45
```

```
Ser Ile Asn Tyr Tyr Met Cys Trp Val Arg Gln Ala Pro Gly Lys Gly
 50                  55                  60
Leu Glu Trp Ile Ala Cys Ile Tyr Thr Gly Asp Asp Thr Phe Tyr
 65                  70                  75                  80
Ala Ser Trp Ala Lys Gly Arg Phe Thr Ile Ser Lys Thr Ser Ser Thr
                 85                  90                  95
Thr Val Thr Leu Gln Leu Asn Ser Leu Thr Ala Ala Asp Thr Ala Thr
                100                 105                 110
Tyr Phe Cys Val Arg Gly Leu Tyr Gly Ser Ile Asn Asn Leu Trp
                115                 120                 125
Gly Pro Gly Thr Leu Val Thr Val Ser Ser Gly Gln Pro Lys Ala Pro
130                 135                 140
Ser Val Phe Pro Leu Ala Pro Cys Cys Gly Asp Thr Pro Ser Ser Thr
145                 150                 155                 160
Val Thr Leu Gly Cys Leu Val Lys Gly Tyr Leu Pro Glu Pro Val Thr
                165                 170                 175
Val Thr Trp Asn Ser Gly Thr Leu Thr Asn Gly Val Arg Thr Phe Pro
                180                 185                 190
Ser Val Arg Gln Ser Ser Gly Leu Tyr Ser Leu Ser Val Val Ser
                195                 200                 205
Val Thr Ser Ser Ser Gln Pro Val Thr Cys Asn Val Ala His Pro Ala
                210                 215                 220
Thr Asn Thr Lys Val Asp Lys Thr Val Ala Pro Ser Thr Cys Ser Lys
225                 230                 235                 240
Pro Thr Cys Pro Pro Pro Glu Leu Leu Gly Gly Pro Ser Val Phe Ile
                245                 250                 255
Phe Pro Pro Lys Pro Lys Asp Thr Leu Met Ile Ser Arg Thr Pro Glu
                260                 265                 270
Val Thr Cys Val Val Val Asp Val Ser Gln Asp Asp Pro Glu Val Gln
                275                 280                 285
Phe Thr Trp Tyr Ile Asn Asn Glu Gln Val Arg Thr Ala Arg Pro Pro
                290                 295                 300
Leu Arg Glu Gln Gln Phe Asn Ser Thr Ile Arg Val Val Ser Thr Leu
305                 310                 315                 320
Pro Ile Ala His Gln Asp Trp Leu Arg Gly Lys Glu Phe Lys Cys Lys
                325                 330                 335
Val His Asn Lys Ala Leu Pro Ala Pro Ile Glu Lys Thr Ile Ser Lys
                340                 345                 350
Ala Arg Gly Gln Pro Leu Glu Pro Lys Val Tyr Thr Met Gly Pro Pro
                355                 360                 365
Arg Glu Glu Leu Ser Ser Arg Ser Val Ser Leu Thr Cys Met Ile Asn
370                 375                 380
Gly Phe Tyr Pro Ser Asp Ile Ser Val Glu Trp Glu Lys Asn Gly Lys
385                 390                 395                 400
Ala Glu Asp Asn Tyr Lys Thr Thr Pro Ala Val Leu Asp Ser Asp Gly
                405                 410                 415
Ser Tyr Phe Leu Tyr Ser Lys Leu Ser Val Pro Thr Ser Glu Trp Gln
                420                 425                 430
Arg Gly Asp Val Phe Thr Cys Ser Val Met His Glu Ala Leu His Asn
                435                 440                 445
His Tyr Thr Gln Lys Ser Ile Ser Arg Ser Pro Gly Lys
                450                 455                 460
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Phe Asp Phe Ser Ile Asn Tyr
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Thr Gly Asp Asp
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Leu Tyr Ser Gly Ser Ile Asn Asn Leu
1               5                   10

<210> SEQ ID NO 26
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggacacga gggcccccac tcagctgctg gggctcctgc tgctctggct cccagatgcc      60
agatgtgcgc ttgtgatgac ccagactcca tccctgtgt ctgcagctgt gggaggcaca     120
gtcaccatca gttgccaggc cagtcagagt gtttataaca cgactactt atcctggtat     180 cagcagaaac agggcagcc tcccaaactc ctgatctatt atgcatccac tctggcatct     240
ggggtctcat cgcggttcaa aggcagtgga tctgggacac agttcactct caccatcagc     300
gacgtgcagt gtgacgatgc tgccgcttac tattgtgcag gcgttaaagg ttatagtaat     360
gataataatg gtttcggcgg agggaccgag gtggtggtca aa                        402

<210> SEQ ID NO 27
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asp Thr Arg Ala Pro Thr Gln Leu Leu Gly Leu Leu Leu Leu Trp

```
                1               5                  10                  15
Leu Pro Asp Ala Arg Cys Ala Leu Val Met Thr Gln Thr Pro Ser Pro
                20                  25                  30

Val Ser Ala Ala Val Gly Gly Thr Val Thr Ile Ser Cys Gln Ala Ser
                35                  40                  45

Gln Ser Val Tyr Asn Asn Asp Tyr Leu Ser Trp Tyr Gln Gln Lys Pro
            50                  55                  60

Gly Gln Pro Pro Lys Leu Leu Ile Tyr Tyr Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
                100                 105                 110

Ala Gly Val Lys Gly Tyr Ser Asn Asp Asn Asn Gly Phe Gly Gly Gly
            115                 120                 125

Thr Glu Val Val Val Lys
            130
```

<210> SEQ ID NO 28
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Asp Thr Arg Ala Pro Thr Gln Leu Leu Gly Leu Leu Leu Leu Trp
1               5                   10                  15

Leu Pro Asp Ala Arg Cys Ala Leu Val Met Thr Gln Thr Pro Ser Pro
                20                  25                  30

Val Ser Ala Ala Val Gly Gly Thr Val Thr Ile Ser Cys Gln Ala Ser
                35                  40                  45

Gln Ser Val Tyr Asn Asn Asp Tyr Leu Ser Trp Tyr Gln Gln Lys Pro
            50                  55                  60

Gly Gln Pro Pro Lys Leu Leu Ile Tyr Tyr Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
                100                 105                 110

Ala Gly Val Lys Gly Tyr Ser Asn Asp Asn Asn Gly Phe Gly Gly Gly
            115                 120                 125

Thr Glu Val Val Val Lys Gly Asp Pro Val Ala Pro Thr Val Leu Ile
            130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
            195                 200                 205

Ser Thr Gln Tyr Asn Ser His Lys Glu Tyr Thr Cys Lys Val Thr Gln
            210                 215                 220
```

Gly Thr Thr Ser Val Val Gln Ser Phe Asn Arg Gly Asp Cys
225                 230                 235

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ala Ser Gln Ser Val Tyr Asn Asn Asp Tyr Leu Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ala Ser Thr Leu Ala Ser
1               5

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Gly Val Lys Gly Tyr Ser Asn Asp Asn Asn Gly
1               5                   10

<210> SEQ ID NO 32
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggagactg ggctgcgctg gcttctcctg gtcgctgtgc tcaaaggtgt ccaatgtcag      60
tcgctggagg agtccggggg aggcctggtc aagcctgggg catccctgac actcacctgc     120
aaagcctctg gattcgactt cagtatcaac tactacatgt gctgggtccg ccaggctcca     180
gggaaggggt tggagtggat cgcatgcatt tatactggtg atgatgacac tttctacgcg     240
agctgggcga aaggccggtt caccatctcc aaaacctcgt cgaccacggt gactctacaa     300
ctgaacagtc tgacagccgc ggacacggcc acctatttct gtgtgagagg tctatatagt     360
ggtagtatta taacctgtgg ggcccaggc accctggtca ccgtctcctc a               411

<210> SEQ ID NO 33
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 33

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

Gly Ala Ser Leu Thr Leu Thr Cys Lys Ala Ser Gly Phe Asp Phe Ser
        35                  40                  45

Ile Asn Tyr Tyr Met Cys Trp Val Arg Gln Ala Pro Gly Lys Gly Leu
    50                  55                  60

Glu Trp Ile Ala Cys Ile Tyr Thr Gly Asp Asp Asp Thr Phe Tyr Ala
65                  70                  75                  80

Ser Trp Ala Lys Gly Arg Phe Thr Ile Ser Lys Thr Ser Ser Thr Thr
                85                  90                  95

Val Thr Leu Gln Leu Asn Ser Leu Thr Ala Ala Asp Thr Ala Thr Tyr
            100                 105                 110

Phe Cys Val Arg Gly Leu Tyr Ser Gly Ser Ile Asn Asn Leu Trp Gly
        115                 120                 125

Pro Gly Thr Leu Val Thr Val Ser Ser
    130                 135

<210> SEQ ID NO 34
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

Gly Ala Ser Leu Thr Leu Thr Cys Lys Ala Ser Gly Phe Asp Phe Ser
        35                  40                  45

Ile Asn Tyr Tyr Met Cys Trp Val Arg Gln Ala Pro Gly Lys Gly Leu
    50                  55                  60

Glu Trp Ile Ala Cys Ile Tyr Thr Gly Asp Asp Asp Thr Phe Tyr Ala
65                  70                  75                  80

Ser Trp Ala Lys Gly Arg Phe Thr Ile Ser Lys Thr Ser Ser Thr Thr
                85                  90                  95

Val Thr Leu Gln Leu Asn Ser Leu Thr Ala Ala Asp Thr Ala Thr Tyr
            100                 105                 110

Phe Cys Val Arg Gly Leu Tyr Ser Gly Ser Ile Asn Asn Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205
```

Thr Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Thr Cys Pro Pro Glu Leu Leu Gly Gly Pro Ser Val Phe Ile Phe
            245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Ala Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460

<210> SEQ ID NO 35
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atggacacga gggcccccac tcagctgctg gggctcctgc tgctctggct cccagatgcc     60
agatgtgcgc ttgtgatgac ccagactcca tccctgtgt ctgcagctgt ggaggcaca    120 gtcaccatca gttgccaggc cagtcagagt gtttataaca acgactactt atcctggtat    180
cagcagaaac cagggcagcc tcccaaactc ctgatctatt atgcatccac tctggcatct    240
ggggtctcat cgcggttcaa aggcagtgga tctgggacac agttcactct caccatcagc    300
gacgtgcagt gtgacgatgc tgccgcttac tattgtgcag gcgttaaagg ttatagtaat    360
gataataatg gtttcggcgg agggaccgag gtggtggtca aa                      402

<210> SEQ ID NO 36
<211> LENGTH: 134
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 36

Met Asp Thr Arg Ala Pro Thr Gln Leu Leu Gly Leu Leu Leu Trp
1               5                   10                  15

Leu Pro Asp Ala Arg Cys Ala Leu Val Met Thr Gln Thr Pro Ser Pro
            20                  25                  30

Val Ser Ala Ala Val Gly Gly Thr Val Thr Ile Ser Cys Gln Ala Ser
        35                  40                  45

Gln Ser Val Tyr Asn Asn Asp Tyr Leu Ser Trp Tyr Gln Gln Lys Pro
    50                  55                  60

Gly Gln Pro Pro Lys Leu Leu Ile Tyr Tyr Ala Ser Thr Leu Ala Ser
65              70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Ala Tyr Tyr Cys
            100                 105                 110

Ala Gly Val Lys Gly Tyr Ser Asn Asp Asn Asn Gly Phe Gly Gly Gly
        115                 120                 125

Thr Glu Val Val Val Lys
    130

<210> SEQ ID NO 37
<211> LENGTH: 238
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 37

Met Asp Thr Arg Ala Pro Thr Gln Leu Leu Gly Leu Leu Leu Trp
1               5                   10                  15

Leu Pro Asp Ala Arg Cys Ala Leu Val Met Thr Gln Thr Pro Ser Pro
            20                  25                  30

Val Ser Ala Ala Val Gly Gly Thr Val Thr Ile Ser Cys Gln Ala Ser
        35                  40                  45

Gln Ser Val Tyr Asn Asn Asp Tyr Leu Ser Trp Tyr Gln Gln Lys Pro
    50                  55                  60

Gly Gln Pro Pro Lys Leu Leu Ile Tyr Tyr Ala Ser Thr Leu Ala Ser
65              70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Ala Tyr Tyr Cys
            100                 105                 110

Ala Gly Val Lys Gly Tyr Ser Asn Asp Asn Asn Gly Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
            195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 38
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggagactg ggctgcgctg gcttctcctg gtcgctgtgc tcaaaggggt ccagtgtcag      60
tcgttggagg agtccggggg agacctggtc aagcctgggg catccctgac actcacctgc    120
acagcctctg gattctcctt cacgagcaac tactacatgt gctgggtccg ccaggctcca    180
gggaaggggc tggagtgggt cgcgtgcatt tttcttggta gtagtggtaa cactgtctac    240
gcgaactggg cgaaaggccg attcaccatc tccaaaacct cgtcgaccac ggtgactctg    300
caaatgacca gtctgacagt cgcggacacg gccacctatt tctgtgcgag agactatgtt    360
aatggttatg actactttaa cttgtggggc ccaggcacct tggtcaccgt ctcctca      417

<210> SEQ ID NO 39
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Thr
        35                  40                  45

Ser Asn Tyr Tyr Met Cys Trp Val Arg Gln Ala Pro Gly Lys Gly Leu
    50                  55                  60

Glu Trp Val Ala Cys Ile Phe Leu Gly Ser Ser Gly Asn Thr Val Tyr
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Val Ala Asp Thr Ala Thr
            100                 105                 110

Tyr Phe Cys Ala Arg Asp Tyr Val Asn Gly Tyr Asp Tyr Phe Asn Leu
        115                 120                 125

Trp Gly Pro Gly Thr Leu Val Thr Val Ser Ser
    130                 135

<210> SEQ ID NO 40
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Thr
        35                  40                  45

Ser Asn Tyr Tyr Met Cys Trp Val Arg Gln Ala Pro Gly Lys Gly Leu
    50                  55                  60

Glu Trp Val Ala Cys Ile Phe Leu Gly Ser Ser Gly Asn Thr Val Tyr
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Val Ala Asp Thr Ala Thr
            100                 105                 110

Tyr Phe Cys Ala Arg Asp Tyr Val Asn Gly Tyr Asp Tyr Phe Asn Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Thr Cys Pro Pro Pro Glu Leu Leu Gly Gly Pro Ser Val Phe
                245                 250                 255

Ile Phe Pro Pro Lys Pro Lys Asp Thr Leu Met Ile Ser Arg Thr Pro
            260                 265                 270

Glu Val Thr Cys Val Val Val Asp Val Ser Gln Asp Asp Pro Glu Val
        275                 280                 285

Gln Phe Thr Trp Tyr Ile Asn Asn Glu Gln Val Arg Thr Ala Arg Pro
    290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
            340                 345                 350

Lys Ala Arg Gly Gln Pro Leu Glu Pro Lys Val Tyr Thr Met Gly Pro
        355                 360                 365

Pro Arg Glu Glu Leu Ser Ser Arg Ser Val Ser Leu Thr Cys Met Ile
    370                 375                 380

Asn Gly Phe Tyr Pro Ser Asp Ile Ser Val Glu Trp Glu Lys Asn Gly
385                 390                 395                 400
```

```
Lys Ala Glu Asp Asn Tyr Lys Thr Thr Pro Ala Val Leu Asp Ser Asp
                405                 410                 415
Gly Ser Tyr Phe Leu Tyr Ser Lys Leu Ser Val Pro Thr Ser Glu Trp
            420                 425                 430
Gln Arg Gly Asp Val Phe Thr Cys Ser Val Met His Glu Ala Leu His
        435                 440                 445
Asn His Tyr Thr Gln Lys Ser Ile Ser Arg Ser Pro Gly Lys
    450                 455                 460

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Phe Ser Phe Thr Ser Asn Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Leu Gly Ser Ser Gly
1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Tyr Val Asn Gly Tyr Asp Tyr Phe Asn Leu
1               5                   10

<210> SEQ ID NO 44
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggacacga gggcccccac tcagctgctg gggctcctgc tgctctggct cccaggtgcc      60
acatttgccc aagtgctgac ccagactgca tcccccgtgt ctgcggctgt ggaggcaca     120 gtcaccatca attgccagtc cagtcagagt gtttataata agaacttagc ctggtatcag    180
cagaaaccag ggcagcctcc caaaggcctg atctattcta catcgactct agattctggg    240
gtcccatcgc ggttcagcgg cagtggatct gggacacagt tcactctcac catcagcgac    300
gtgcagtgtg acgatgctgc cacttactac tgtctaggca gttatgattg tagtagtgct    360
gattgtaatg ctttcggcgg agggaccgag gtggtggtca aa                       402
```

<210> SEQ ID NO 45
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Gly Thr Val Thr Ile Asn Cys Gln Ser Ser
        35                  40                  45

Gln Ser Val Tyr Asn Lys Asn Leu Ala Trp Tyr Gln Gln Lys Pro Gly
    50                  55                  60

Gln Pro Pro Lys Gly Leu Ile Tyr Ser Thr Ser Thr Leu Asp Ser Gly
65                  70                  75                  80

Val Pro Ser Arg Phe Ser Gly Ser Gly Ser Gly Thr Gln Phe Thr Leu
                85                  90                  95

Thr Ile Ser Asp Val Gln Cys Asp Asp Ala Ala Thr Tyr Tyr Cys Leu
            100                 105                 110

Gly Ser Tyr Asp Cys Ser Ser Ala Asp Cys Asn Ala Phe Gly Gly Gly
        115                 120                 125

Thr Glu Val Val Val Lys
    130

<210> SEQ ID NO 46
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Gly Thr Val Thr Ile Asn Cys Gln Ser Ser
        35                  40                  45

Gln Ser Val Tyr Asn Lys Asn Leu Ala Trp Tyr Gln Gln Lys Pro Gly
    50                  55                  60

Gln Pro Pro Lys Gly Leu Ile Tyr Ser Thr Ser Thr Leu Asp Ser Gly
65                  70                  75                  80

Val Pro Ser Arg Phe Ser Gly Ser Gly Ser Gly Thr Gln Phe Thr Leu
                85                  90                  95

Thr Ile Ser Asp Val Gln Cys Asp Asp Ala Ala Thr Tyr Tyr Cys Leu
            100                 105                 110

Gly Ser Tyr Asp Cys Ser Ser Ala Asp Cys Asn Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

```
Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ser Ser Gln Ser Val Tyr Asn Lys Asn Leu Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Thr Ser Thr Leu Asp Ser
1               5

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Gly Ser Tyr Asp Cys Ser Ser Ala Asp Cys Asn Ala
1               5                   10

<210> SEQ ID NO 50
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atggagactg ggctgcgctg gcttctcctg gtcgctgtgc tcaaaggtgt ccaatgtcag      60
tcgctggagg agtccggggg aggcctggtc aagcctgggg catccctgac actcacctgc    120
acagcctctg gattctcctt cagtgacagt tggtacttgt gttgggtccg ccaggctcca    180
gggaaggggc tggagtggat cgcatgcatt tatactggtg atggtgacac ttattacgcg    240
acctgggcga aaggccgatt caccatctcc aagacctcgt cgaccacagt gactctacaa    300
atgaccagtc tgacagccgc ggacacggcc acctatttct gtgcgagggg tgcccaattt    360
```
tacttgtggg gccaaggcac cctggtcacc gtctcctca    399

<210> SEQ ID NO 51
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

Gly Ala Ser Leu Thr Leu Thr Cys Thr Ala Ser Gly Phe Ser Phe Ser
        35                  40                  45

Asp Ser Trp Tyr Leu Cys Trp Val Arg Gln Ala Pro Gly Lys Gly Leu
    50                  55                  60

Glu Trp Ile Ala Cys Ile Tyr Thr Gly Asp Gly Asp Thr Tyr Tyr Ala
65                  70                  75                  80

Thr Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Gly Ala Gln Phe Tyr Leu Trp Gly Gln Gly Thr Leu
        115                 120                 125

Val Thr Val Ser Ser
    130

<210> SEQ ID NO 52
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

Gly Ala Ser Leu Thr Leu Thr Cys Thr Ala Ser Gly Phe Ser Phe Ser
        35                  40                  45

Asp Ser Trp Tyr Leu Cys Trp Val Arg Gln Ala Pro Gly Lys Gly Leu
    50                  55                  60

Glu Trp Ile Ala Cys Ile Tyr Thr Gly Asp Gly Asp Thr Tyr Tyr Ala
65                  70                  75                  80

Thr Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Gly Ala Gln Phe Tyr Leu Trp Gly Gln Gly Thr Leu
        115                 120                 125

Val Thr Val Ser Ser Gly Gln Pro Lys Ala Pro Ser Val Phe Pro Leu
    130                 135                 140

```
Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Pro Glu Val Gln Phe Thr Trp Tyr Ile
        275                 280                 285

Asn Asn Glu Gln Val Arg Thr Ala Arg Pro Pro Leu Arg Glu Gln Gln
290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Ser Phe Ser Asp Ser Trp
1               5

<210> SEQ ID NO 54
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 54

Tyr Thr Gly Asp Gly
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ala Gln Phe Tyr Leu
1               5

<210> SEQ ID NO 56
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggacacga gggcccccac tcagctgctg gggctcctgc tgctctggct cccaggtgcc      60
acatttgccc aggtgctgac ccagactcca tcctccgtgt ctgcagctgt gggaggcaca     120
gtcaccatca attgccagtc cagtcagagt gtttatgcca acacctactt atcctggtat     180
cagcagaaac cagggcagcc tcccaagcaa ctgatctatt ctgcatccag tctggcatct     240
ggggtcccac cgcggttcaa aggcagtgga tctgggacac agttcgctct caccatcagc     300
gacgtgcagt gtgacgatgc tgccacttac tactgtctag cagatatagt tgtggtctt     360 gctgattgtg ctgctttcgg cggagggacc gaggtggtgg tcaaa                    405

<210> SEQ ID NO 57
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ser Ser
            35                  40                  45

Gln Ser Val Tyr Ala Asn Thr Tyr Leu Ser Trp Tyr Gln Gln Lys Pro
        50                  55                  60

Gly Gln Pro Pro Lys Gln Leu Ile Tyr Ser Ala Ser Ser Leu Ala Ser
65                  70                  75                  80

Gly Val Pro Pro Arg Phe Lys Gly Ser Gly Ser Gly Thr Gln Phe Ala
                85                  90                  95

Leu Thr Ile Ser Asp Val Gln Cys Asp Asp Ala Ala Thr Tyr Tyr Cys
            100                 105                 110
```

```
Leu Gly Arg Tyr Ser Cys Gly Leu Ala Asp Cys Ala Ala Phe Gly Gly
        115                 120                 125

Gly Thr Glu Val Val Val Lys
    130                 135

<210> SEQ ID NO 58
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ser Ser
        35                  40                  45

Gln Ser Val Tyr Ala Asn Thr Tyr Leu Ser Trp Tyr Gln Gln Lys Pro
    50                  55                  60

Gly Gln Pro Pro Lys Gln Leu Ile Tyr Ser Ala Ser Ser Leu Ala Ser
65                  70                  75                  80

Gly Val Pro Pro Arg Phe Lys Gly Ser Gly Ser Gly Thr Gln Phe Ala
                85                  90                  95

Leu Thr Ile Ser Asp Val Gln Cys Asp Asp Ala Ala Thr Tyr Tyr Cys
            100                 105                 110

Leu Gly Arg Tyr Ser Cys Gly Leu Ala Asp Cys Ala Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ser Ser Gln Ser Val Tyr Ala Asn Thr Tyr Leu Ser
1               5                   10

<210> SEQ ID NO 60
```

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Ala Ser Ser Leu Ala Ser
1               5

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Gly Arg Tyr Ser Cys Gly Leu Ala Asp Cys Ala Ala
1               5                   10

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Asn Gly Ile Cys
1               5

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Leu Tyr Val Gly Ser Ser Asp Thr Thr Tyr Tyr Ala Ser Trp Ala
1               5                   10                  15

Lys

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Asn Tyr Tyr Met Cys
1               5

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 65

Cys Ile Tyr Thr Gly Asp Asp Asp Thr Phe Tyr Ala Ser Trp Ala Lys
1               5                   10                  15

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Asn Tyr Tyr Met Cys
1               5

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Ile Phe Leu Gly Ser Ser Gly Asn Thr Val Tyr Ala Asn Trp Ala
1               5                   10                  15

Lys

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ser Trp Tyr Leu Cys
1               5

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Ile Tyr Thr Gly Asp Gly Asp Thr Tyr Tyr Ala Thr Trp Ala Lys
1               5                   10                  15

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Phe Ser Phe Ser Asn Asn Gly Ile Cys
1               5                   10

<210> SEQ ID NO 71
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Asp Phe Ser Ile Asn Tyr Tyr Met Cys
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Ser Phe Thr Ser Asn Tyr Tyr Met Cys
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Phe Ser Phe Ser Asp Ser Trp Tyr Leu Cys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 74

Arg Ala Ser Gln Asp Ile Ser Lys Tyr Leu Asn
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 75

His Thr Ser Arg Leu His Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 76

Gln Gln Gly Asn Thr Leu Pro Tyr Thr
1               5
```

```
<210> SEQ ID NO 77
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 77

Gly Val Ser Leu Pro Asp Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 78

Trp Gly Ser Glu Thr
1               5

<210> SEQ ID NO 79
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 79

His Tyr Tyr Tyr Gly Gly Ser Tyr Ala Met Asp Tyr
1               5                   10

<210> SEQ ID NO 80
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 80

Asp Tyr Gly Val Ser
1               5

<210> SEQ ID NO 81
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 81

Val Ile Trp Gly Ser Glu Thr Thr Tyr Tyr Asn Ser Ala Leu Lys Ser
1               5                   10                  15

<210> SEQ ID NO 82
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 82

Gly Val Ser Leu Pro Asp Tyr Gly Val Ser
1               5                   10
```

ANTIGEN BINDING MOLECULES SPECIFIC FOR AN ANTI-CD19 SCFV

CROSS REFERENCE TO RELATED APPLICATIONS

This application claims priority to U.S. Provisional Patent Application Ser. No. 62/401,007 filed Sep. 28, 2016, the entire disclosure of which is hereby incorporated by reference.

SEQUENCE LISTING

The instant application contains a Sequence Listing, which has been submitted electronically in ASCII format, and is hereby incorporated by reference in its entirety. Said ASCII copy, created on Sep. 26, 2017, is named K-103602_SL.txt and is 74,224 bytes in size.

FIELD OF THE INVENTION

This disclosure relates to antigen binding molecules, such as antibodies, which specifically bind to the anti-CD19 scFv FMC63, as well as molecules comprising these sequences and cells presenting such molecules, polynucleotides encoding such antigen binding molecules, as well as humanized forms of the antigen binding molecules; methods of using the antigen binding molecules are also disclosed.

BACKGROUND OF THE INVENTION

Antigen binding molecules, including antibodies, and fragments such as Fabs, F(ab')$_2$, scFvs, etc, are used in immunotherapy and solid phase-based applications such as biosensors, affinity chromatography, and immunoassays. These antibodies and other antigen binding molecules gain their utility by virtue of their ability to specifically bind their targets.

Anti-idiotypic antibodies are a subset of antibodies, and are antibodies raised against immunizing antibodies. These anti-idiotypic antibodies demonstrated specific binding against the idiotopes (unique antigenic determinants on the surface of the antibodies) of the immunizing antibodies. Anti-idiotypic antibodies can be generally classified into three distinct groups: (1) antibodies are those that recognize idiotopes distinct from the antigen-binding site (ABS) on immunizing antibodies; (2) antibodies that recognize epitopes within the ABS and mimic the structure, and forming the so-called "internal image," of the nominal antigen; and (3) antibodies that recognize epitopes within the ABS without the structural resemblance of the nominal antigen (see, e.g., Pan et al., (1995) *FASEB J* 9:43-49).

FMC63 is an IgG2a mouse monoclonal antibody that recognizes CD19, which is expressed on the surface of B cells (Zola et al., (1991) *Immunol Cell Biol* 69:411-22). Single chain variable fragments (scFv) formed from FMC63 comprise the targeting component of some chimeric antigen receptors (CARs) (Kochenderfer et al., (2009) *J Immunother* 32(7):689-702), and the scFv of FMC63 has previously been used to generate anti-FMC63 antibodies (Jena et al., (2013) *PLoS ONE* 8(3):e57838).

Disclosed herein are rabbit antigen binding molecules, including antibodies, that specifically bind to the anti-CD19 scFv FMC63 (SEQ ID NO: 1), as well as molecules comprising these sequences and cells presenting such molecules. Humanized forms of the disclosed rabbit antigen binding molecules also form as aspect of the disclosure. Applications and uses of these antigen binding molecules are also disclosed.

SUMMARY OF THE INVENTION

In one aspect, an isolated antigen binding molecule that specifically binds a molecule comprising SEQ ID NO: 1 is provided. In some embodiments, the antigen binding molecule specifically binds a molecule comprising one or more peptides (e.g., complementarity determining regions (CDRs)) selected from the group consisting of SEQ ID NOs:74-82. In some embodiments, the antigen binding molecule is selected from the group consisting of an antibody, an scFv, a Fab, a Fab', a Fv, a F(ab')$_2$, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody an IgG2 antibody having at least one mutation in the hinge region, an IgG3 antibody, an IgG3 antibody having at least one mutation in the hinge region, an IgG4 antibody, an IgG4 antibody having at least one mutation in the hinge region, an antibody comprising at least one non-naturally occurring amino acid, and any combination thereof.

In some embodiments, the antigen binding molecule comprises a heavy chain (HC) and in further embodiments the HC comprises a heavy chain variable region (VH) sequence selected from the group consisting of SEQ ID NOs: 3, 15, 21, 33, 39 and 51. In still other embodiments, the variable region (VH) of the antigen binding molecule comprises one or more of (a) a CDR1, (b) a CDR2, and (c) a CDR3. In some embodiments, the antigen binding molecule comprises a heavy chain CDR1 selected from the group consisting of SEQ ID NOs: 5, 23, 41 and 53. In some embodiments, the antigen binding molecule comprises a heavy chain CDR2 selected from the group consisting of SEQ ID NOs: 6, 24, 42 and 54. In some embodiments the antigen binding molecule comprises a heavy chain CDR3 selected from the group consisting of SEQ ID NOs: 7, 25, 43 and 55. In additional embodiments, the antigen binding molecule comprises a heavy chain comprising a heavy chain CDR1, a heavy chain CDR2, and a heavy chain CDR3, each CDR comprising an amino acid sequence shown in FIGS. 5-21. In still further embodiments, an antigen binding molecule which comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule provided herein.

In some embodiments, the antigen binding molecule comprises a light chain (LC) and in further embodiments the LC comprises a light chain variable region (VL) sequence selected from the group consisting of SEQ ID NOs: 8, 18, 27, 36, 45 and 57. In additional embodiments, the variable region (VL) and comprises one or more of (a) a CDR1, (b) a CDR2, and (c) a CDR3. In some embodiments, the antigen binding molecule comprises a light chain CDR1 selected from the group consisting of SEQ ID NOs: 11, 29, 47 and 59. In some embodiments, the antigen binding molecule comprises a light chain CDR2 selected from the group consisting of SEQ ID NOs: 12, 30, 48 and 60. In some embodiments, the antigen binding molecule comprises a light chain CDR3 selected from the group consisting of SEQ ID NOs: 13, 31, 49 and 61. In some embodiments, the light chain comprises a light chain CDR1, a light chain CDR2, and a light chain CDR3, each CDR comprising an amino acid sequence shown in one of FIGS. 5-21. In still further embodiments, an antigen binding molecule which comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VL of an antigen binding molecule provided herein.

In some embodiments, an antigen binding molecule comprises (a) a VH comprising the amino acid sequence of SEQ ID NO: 3; and (b) a VL comprising the amino acid sequence of SEQ ID NO: 9. In some embodiments, an antigen binding molecule comprises: (a) a VH CDR1 region comprising the amino acid sequence of SEQ ID NO: 5; (b) a VH CDR2 region comprising the amino acid sequence of SEQ ID NO: 6; (c) a VH CDR3 region comprising the amino acid sequence of SEQ ID NO: 7; (d) a VL CDR1 region comprising the amino acid sequence of SEQ ID NO: 11; (e) a VL CDR2 region comprising the amino acid sequence of SEQ ID NO: 12; and (f) a VL CDR3 region comprising the amino acid sequence of SEQ ID NO: 13.

In some embodiments, an antigen binding molecule comprises (a) a VH comprising the amino acid sequence of SEQ ID NO: 15; and (b) a VL comprising the amino acid sequence of SEQ ID NO: 18. In some embodiments, an antigen binding molecule comprises (a) a VH CDR1 region comprising the amino acid sequence of SEQ ID NO: 5; (b) a VH CDR2 region comprising the amino acid sequence of SEQ ID NO: 6; (c) a VH CDR3 region comprising the amino acid sequence of SEQ ID NO: 7; (d) a VL CDR1 region comprising the amino acid sequence of SEQ ID NO: 11; (e) a VL CDR2 region comprising the amino acid sequence of SEQ ID NO: 12; and (f) a VL CDR3 region comprising the amino acid sequence of SEQ ID NO: 13.

In some embodiments, an antigen binding molecule comprises (a) a VH comprising the amino acid sequence of SEQ ID NO: 21; and (b) a VL comprising the amino acid sequence of SEQ ID NO: 27. In some embodiments, an antigen binding molecule comprises (a) a VH CDR1 region comprising the amino acid sequence of SEQ ID NO: 23; (b) a VH CDR2 region comprising the amino acid sequence of SEQ ID NO: 24; (c) a VH CDR3 region comprising the amino acid sequence of SEQ ID NO: 25; (d) a VL CDR1 region comprising the amino acid sequence of SEQ ID NO: 29; (e) a VL CDR2 region comprising the amino acid sequence of SEQ ID NO: 30; and (f) a VL CDR3 region comprising the amino acid sequence of SEQ ID NO: 31.

In some embodiments, an antigen binding molecule comprises (a) a VH comprising the amino acid sequence of SEQ ID NO: 33; and (b) a VL comprising the amino acid sequence of SEQ ID NO: 36. In some embodiments, an antigen binding molecule comprises (a) a VH CDR1 region comprising the amino acid sequence of SEQ ID NO: 23; (b) a VH CDR2 region comprising the amino acid sequence of SEQ ID NO: 24; (c) a VH CDR3 region comprising the amino acid sequence of SEQ ID NO: 25; (d) a VL CDR1 region comprising the amino acid sequence of SEQ ID NO: 29; (e) a VL CDR2 region comprising the amino acid sequence of SEQ ID NO: 30; and (f) a VL CDR3 region comprising the amino acid sequence of SEQ ID NO: 31.

In some embodiments, an antigen binding molecule comprises (a) a VH comprising the amino acid sequence of SEQ ID NO: 39; and (b) a VL comprising the amino acid sequence of SEQ ID NO: 45. In some embodiments, an antigen binding molecule comprises (a) a VH CDR1 region comprising the amino acid sequence of SEQ ID NO: 41; (b) a VH CDR2 region comprising the amino acid sequence of SEQ ID NO: 42; (c) a VH CDR3 region comprising the amino acid sequence of SEQ ID NO: 43; (d) VL CDR1 region comprising the amino acid sequence of SEQ ID NO: 47; (e) a VL CDR2 region comprising the amino acid sequence of SEQ ID NO: 48; and (f) a VL CDR3 region comprising the amino acid sequence of SEQ ID NO: 49.

In a specific embodiment, an antigen binding molecule comprises (a) a VH comprising the amino acid sequence of SEQ ID NO: 51; and (b) a VL comprising the amino acid sequence of SEQ ID NO: 57. In some embodiments, an antigen binding molecule comprises (a) a VH CDR1 region comprising the amino acid sequence of SEQ ID NO: 53; (b) a VH CDR2 region comprising the amino acid sequence of SEQ ID NO: 54; (c) a VH CDR3 region comprising the amino acid sequence of SEQ ID NO: 55; (d) a VL CDR1 region comprising the amino acid sequence of SEQ ID NO: 59; (e) a VL CDR2 region comprising the amino acid sequence of SEQ ID NO: 60; and (f) a VL CDR3 region comprising the amino acid sequence of SEQ ID NO: 61.

In various embodiments, an antigen binding molecule provided herein further comprises a detectable label, and can be selected from the group consisting of a fluorescent label, a photochromic compound, a proteinaceous fluorescent label, a magnetic label, a radiolabel, and a hapten. In various embodiments, a fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry.

In another aspect, a composition comprising an antigen binding molecule disclosed herein is provided. Also provided is a polynucleotide encoding the heavy chain of an antigen binding molecule disclosed herein, and a polynucleotide encoding the light chain of an antigen binding molecule disclosed herein. A vector comprising the polynucleotides is also disclosed. Further, a cell comprising one or more such vectors is disclosed. In various embodiments, the cell comprises a cell selected from the group consisting of a CHO cell, a Sp2/0 cell, a rabbit cell and an *E. coli* cell. A method of making an antigen binding molecule disclosed herein comprising incubating a cell disclosed herein under suitable conditions is provided.

In another aspect, a method of administering a dose of a medicament to a subject, the dose comprising a preselected number of cells presenting a therapeutic molecule comprising SEQ ID NO: 1, is provided. In some embodiments the method comprises (a) providing a sample of known volume comprising a population comprising a known number of cells, which cells are known or suspected to be presenting a molecule comprising SEQ ID NO: 1; (b) providing an aliquot of the sample comprising a population of cells presenting a therapeutic molecule comprising SEQ ID NO: 1; (c) providing an antigen binding molecule that specifically binds the SEQ ID NO: 1, the antigen binding molecule further comprising a detectable label; (d) contacting the aliquot of (b) with the antigen binding molecule of (c) under conditions that permit the formation of a binding complex comprising a cell present in the sample and the antigen binding molecule; (e) determining the fraction of cells present in a binding complex of (d) in the aliquot; (f) determining the concentration of cells presenting a molecule comprising SEQ ID NO: 1 in the sample, based on the fraction of cells determined in (e); (g) determining the volume of the sample that comprises the selected number of cells; and (h) administering the volume of the sample determined in (g) to the subject.

In some embodiments of the method, (a) the molecule comprising SEQ ID NO: 1 is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In another embodiment, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In an additional embodiment, the detectable label is selected from the group consisting of a fluorescent label, a photochromic compound, a proteinaceous fluorescent label, a magnetic label, a radiolabel, and a hapten. In further embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. In an embodiment, the dose is $1.0 \times 10^6$ cells per kilogram of the subject. Additionally, in various embodiments of the disclosed method the antigen binding molecule comprises an antigen binding molecule disclosed herein, and humanized forms thereof.

In another aspect, a method of administering a dose of a medicament to a subject, the dose comprising a preselected number of cells presenting a therapeutic molecule comprising CDR sequences according to any one of SEQ ID Nos: 74-82, is provided. In some embodiments, the method comprises (a) providing a sample of known volume comprising a population comprising a known number of cells, which cells are known or suspected to be presenting a molecule comprising CDR sequences according to any one of SEQ ID Nos: 74-82; (b) providing an aliquot of the sample comprising a population of cells presenting a therapeutic molecule comprising CDR sequences according to any one of SEQ ID Nos: 74-82; (c) providing an antigen binding molecule that specifically binds a molecule comprising CDR sequences according to any one of SEQ ID Nos: 74-82, the antigen binding molecule further comprising a detectable label; (d) contacting the aliquot of (b) with the antigen binding molecule of (c) under conditions that permit the formation of a binding complex comprising a cell present in the sample and the antigen binding molecule; (e) determining the fraction of cells present in a binding complex of (d) in the aliquot; (f) determining the concentration of cells presenting a molecule comprising CDR sequences according to any one of SEQ ID Nos: 74-82 in the sample, based on the fraction of cells determined in (e); (g) determining the volume of the sample that comprises the selected number of cells; and (h) administering the volume of the sample determined in (g) to the subject.

In some embodiments of the method, (a) the molecule comprising CDR sequences according to any one of SEQ ID Nos: 74-82 is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In some embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In some embodiments, the detectable label is selected from the group consisting of a fluorescent label, a photochromic compound, a proteinaceous fluorescent label, a magnetic label, a radiolabel, and a hapten. In further embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. In an embodiment, the dose is $1.0 \times 10^6$ cells per kilogram of the subject. Additionally, in various embodiments of the disclosed method the antigen binding molecule comprises an antigen binding molecule disclosed herein, and humanized forms thereof.

In another aspect, a method of determining a number of cells presenting a molecule comprising SEQ ID NO: 1 in a sample is provided. In an embodiment, the method comprises (a) providing a sample comprising cells known or suspected to be presenting a molecule comprising SEQ ID NO: 1; (b) contacting the sample of (a) with an antigen binding molecule that specifically binds the molecule comprising SEQ ID NO: 1, the antigen binding molecule further comprising a detectable label, under conditions that permit the formation of a binding complex comprising a cell present in the sample and the antigen binding molecule; and (c) determining the number of cells present in a binding complex of (b) in the sample.

In some embodiments of the disclosed method, (a) the molecule comprising SEQ ID NO: 1 is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In some embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CD1-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In some embodiments, the detectable label is selected from the group consisting of a fluorescent label, a photochromic compound, a proteinaceous fluorescent label, a magnetic label, a radiolabel, and a hapten. In some embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. Additionally, in various embodiments of the disclosed method, the antigen binding molecule comprises an antigen binding molecule disclosed herein, and humanized forms thereof.

In another aspect, a method of determining a number of cells presenting a molecule comprising CDR sequences according to any one of SEQ ID Nos: 74-82 in a sample is provided. In some embodiments, the method comprises (a) providing a sample comprising cells known or suspected to be presenting a molecule comprising CDR sequences according to any one of SEQ ID Nos: 74-82; (b) contacting the sample of (a) with an antigen binding molecule that specifically binds the molecule comprising CDR sequences according to any one of SEQ ID Nos: 74-82 is provided, the antigen binding molecule further comprising a detectable label, under conditions that permit the formation of a binding complex comprising a cell present in the sample and the antigen binding molecule; and (c) determining the number of cells present in a binding complex of (b) in the sample.

In some embodiments of the disclosed method, (a) the molecule comprising CDR sequences according to any one of SEQ ID Nos: 74-82 is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In some embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In some embodiments, the detectable label is selected from the group consisting of a fluorescent label, a photochromic compound, a proteinaceous fluorescent label, a magnetic label, a radiolabel, and a hapten. In some embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. Additionally, in various embodiments of the disclosed method the antigen binding molecule comprises an antigen binding molecule disclosed herein, and humanized forms thereof.

In another aspect, a method of isolating a molecule comprising SEQ ID NO: 1, is provided. In an embodiment, the method comprises (a) providing a sample known or suspected to comprise a molecule comprising SEQ ID NO: 1; (b) providing an antigen binding molecule that specifically binds a molecule comprising SEQ ID NO: 1, optionally comprising a detectable label; (c) contacting the sample with the antigen binding molecule, under conditions that permit the formation of a binding complex comprising the molecule comprising SEQ ID NO: 1 and the antigen binding molecule; (d) separating any molecules not part of a binding complex from formed binding complexes; and (e) separating a formed binding complex into: (a) a molecule comprising SEQ ID NO: 1, and (b) an antigen binding molecule.

In embodiments of the disclosed method, the molecule comprising SEQ ID NO: 1 is a CAR. In embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, WIC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In some embodiments, the antigen binding molecule is disposed on a surface selected from the group consisting of an agarose bead, a magnetic bead, a plastic welled plate, a glass welled plate, a ceramic welled plate and a cell culture bag. some embodiments, the detectable label is selected from the group consisting of a fluorescent label, a photochromic compound, a proteinaceous fluorescent label, a magnetic label, a radiolabel, and a hapten. In some embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. Additionally, in various embodiments of the disclosed method the antigen binding molecule comprises an antigen binding molecule disclosed herein, and humanized forms thereof.

In another aspect, a method of isolating a molecule comprising CDR sequences according to any one of SEQ ID Nos: 74-82, is provided. In an embodiment, the method comprises (a) providing a sample known or suspected to comprise a molecule comprising CDR sequences according to any one of SEQ ID Nos: 74-82; (b) providing an antigen binding molecule that specifically binds a molecule comprising CDR sequences according to any one of SEQ ID Nos: 74-82, optionally comprising a detectable label; (c) contacting the sample with the antigen binding molecule, under conditions that permit the formation of a binding complex comprising the molecule comprising CDR sequences according to any one of SEQ ID Nos: 74-82 and the antigen binding molecule; (d) separating any molecules not part of a binding complex from formed binding complexes; and (e) separating a formed binding complex into: (a) a molecule comprising CDR sequences according to any one of SEQ ID Nos: 74-82, and (b) an antigen binding molecule.

In some embodiments of the disclosed method, the molecule comprising CDR sequences according to any one of SEQ ID Nos: 74-82 is a CAR. In embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In some embodiments, the antigen binding molecule is disposed on a surface selected from the group consisting of an agarose bead, a magnetic bead, a plastic welled plate, a glass welled plate, a ceramic welled plate and a cell culture bag. In some embodiments, the detectable label is selected from the group consisting of a fluorescent label, a photochromic compound, a proteinaceous fluorescent label, a magnetic label, a radiolabel, and a hapten. In some embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. Additionally, in various embodiments of the disclosed method the antigen binding molecule comprises an antigen binding molecule disclosed herein, and humanized forms thereof.

In another aspect, a method of determining the presence or absence of a molecule comprising SEQ ID NO: 1 in a sample. In some embodiments, the method comprises (a) providing a sample known or suspected to comprise a molecule comprising SEQ ID NO: 1; (b) providing an antigen binding molecule comprising a detectable label that specifically binds a molecule comprising SEQ ID NO: 1; (c) contacting the sample with the antigen binding molecule under conditions that permit the formation of a binding complex; (d) separating any molecules not part of a binding complex from formed binding complexes; and (e) detecting the presence or absence of a binding complex.

In some embodiments, the molecule comprising SEQ ID NO: 1 is a CAR, and in further embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, WIC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In additional embodiments, the antigen binding molecule is disposed on a surface selected from the group consisting of an agarose bead, a magnetic bead, a plastic welled plate, a glass welled plate, a ceramic welled plate and a cell culture bag. In further embodiments, the detectable label is selected from the group consisting of a fluorescent label, a photochromic compound, a proteinaceous fluorescent label, a magnetic label, a radiolabel, and a hapten. In still further embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. Additionally, in various embodiments of the disclosed method the antigen binding molecule comprises an antigen binding molecule disclosed herein, and humanized forms thereof.

In another aspect, a method of determining the presence or absence of a molecule comprising CDR sequences according to any one of SEQ ID Nos: 74-82 in a sample. In some embodiments, the method comprises (a) providing a sample known or suspected to comprise a molecule comprising CDR sequences according to any one of SEQ ID Nos: 74-82; (b) providing an antigen binding molecule comprising a detectable label that specifically binds a molecule comprising CDR sequences according to any one of SEQ ID Nos: 74-82; (c) contacting the sample with the antigen binding molecule under conditions that permit the formation of a binding complex; (d) separating any molecules not part of a binding complex from formed binding complexes; and (e) detecting the presence or absence of a binding complex.

In some embodiments, the molecule comprising CDR sequences according to any one of SEQ ID Nos: 74-82 is a CAR, and in further embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In additional embodiments, the antigen binding molecule is disposed on a surface selected from the group consisting of an agarose bead, a magnetic bead, a plastic welled plate, a glass welled plate, a ceramic welled plate and a cell culture bag. In further embodiments, the detectable label is selected from the group consisting of a fluorescent label, a photochromic compound, a proteinaceous fluorescent label, a magnetic label, a radiolabel, and a hapten. In still further embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. Additionally, in various embodiments of the disclosed method the antigen binding molecule comprises an antigen binding molecule disclosed herein, and humanized forms thereof.

In yet another aspect, a method of increasing the concentration of cells presenting a molecule comprising SEQ ID NO: 1 is provided. In some embodiments, the method comprises (a) providing a sample comprising a cell known or suspected to present a molecule comprising SEQ ID NO: 1; (b) providing an antigen binding molecule that specifically binds a molecule comprising SEQ ID NO: 1, optionally comprising a detectable label; (c) contacting the sample with the antigen binding molecule under conditions that permit the formation of a binding complex comprising the molecule comprising SEQ ID NO: 1 and the antigen binding molecule; (d) removing any components not part of a binding complex; and (e) repeating steps (a)-(d) a desired number of times.

In an embodiment, (a) the molecule comprising SEQ ID NO: 1 is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In other embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. Additionally, in various embodiments of the disclosed method the antigen binding molecule comprises an antigen binding molecule disclosed herein, and humanized forms thereof. In further embodiments, the detectable label is selected from the group consisting of a fluorescent label, a photochromic compound, a proteinaceous fluorescent label, a magnetic label, a radiolabel, and a hapten. In embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry.

In yet another aspect, a method of increasing the concentration of cells presenting a molecule comprising CDR sequences according to any one of SEQ ID Nos: 74-82 is provided. In an embodiment, the method comprises (a) providing a sample comprising a cell known or suspected to present a molecule comprising CDR sequences according to any one of SEQ ID Nos: 74-82; (b) providing an antigen binding molecule that specifically binds a molecule comprising CDR sequences according to any one of SEQ ID Nos: 74-82, optionally comprising a detectable label; (c) contacting the sample with the antigen binding molecule under conditions that permit the formation of a binding complex comprising the molecule comprising CDR sequences according to any one of SEQ ID Nos: 74-82 and the antigen binding molecule; (d) removing any components not part of a binding complex; and (e) repeating steps (a)-(d) a desired number of times.

In an embodiment, (a) the molecule comprising CDR sequences according to any one of SEQ ID Nos: 74-82 is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In other embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/ RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. Additionally, in various embodiments of the disclosed method the antigen binding molecule comprises an antigen binding molecule disclosed herein, and humanized forms thereof. In further embodiments, the detectable label is selected from the group consisting of a fluorescent label, a photochromic compound, a proteinaceous fluorescent label, a magnetic label, a radiolabel, and a hapten. In embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange Lucifer Yellow, NBD, R-Phycoerythrin (PE), PE-Cy5 conjugates, PE-Cy7 conjugates, Red 613, PerCP, Tru-Red, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry.

In another aspect, a method of depleting a population of immune cells presenting a molecule comprising SEQ ID NO: 1 is provided. In some embodiments, the method comprises (a) providing a population of immune cells to be depleted, wherein the immune cells are known or suspected to be presenting a molecule comprising SEQ ID NO: 1; and (b) contacting the immune cells with an antigen binding molecule that specifically binds to (a) the molecule comprising SEQ ID NO: 1, and (b) an activating molecule expressed on the surface of the an immune cell not presenting the molecule comprising SEQ ID NO: 1, under conditions that permit the formation of a ternary binding complex comprising the molecule comprising SEQ ID NO: 1, the activating molecule and the antigen binding molecule. In further embodiments, (a) the molecule comprising SEQ ID NO: 1 is a CAR; and (b) the immune cell selected from the group consisting of CD8+ T cells, CD4+ T cells, tumor infiltrating lymphocytes (TILs), NK cells, TCR-expressing cells, dendritic cells, and NK-T cells. In still further embodiments, the CAR further comprises a molecule, or a fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CD1-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/ RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. Additionally, in various embodiments of the disclosed method the antigen binding molecule comprises an antigen binding molecule disclosed herein, and humanized forms thereof.

In another aspect, a method of depleting a population of immune cells presenting a molecule comprising CDR sequences according to any one of SEQ ID Nos: 74-82 is provided. In some embodiments, the method comprises (a) providing a population of immune cells to be depleted, wherein the immune cells are known or suspected to be presenting a molecule comprising CDR sequences according to any one of SEQ ID Nos: 74-82; and (b) contacting the immune cells with an antigen binding molecule that specifically binds to (a) the molecule comprising CDR sequences according to any one of SEQ ID Nos: 74-82, and (b) an activating molecule expressed on the surface of the an immune cell not presenting the molecule comprising CDR sequences according to any one of SEQ ID Nos: 74-82, under conditions that permit the formation of a ternary binding complex comprising the molecule comprising CDR sequences according to any one of SEQ ID Nos: 74-82, the activating molecule and the antigen binding molecule.

In further embodiments, (a) the molecule comprising CDR sequences according to any one of SEQ ID Nos: 74-82 is a CAR; and (b) the immune cell selected from the group consisting of CD8+ T cells, CD4+ T cells, tumor infiltrating lymphocytes (TILs), NK cells, TCR-expressing cells, dendritic cells, and NK-T cells. In still further embodiments, the CAR further comprises a molecule, or a fragment thereof, selected from the group consisting of CD28, OX-40, 4-1BB/

CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof. In additional embodiments, the immune cell is a T cell and in still further embodiments the T cell is disposed in vitro or the T cell is disposed in vivo. In other embodiments, the T cell is in one of blood, extracted tissue, tissue grown ex vivo, and cell culture media. In some embodiments, the T cell is an autologous T cell, and in other embodiments the T cell is an allogenic T cell. Additionally, in various embodiments of the disclosed method the antigen binding molecule comprises an antigen binding molecule disclosed herein, and humanized forms thereof.

BRIEF DESCRIPTION OF THE FIGURES

FIG. 3 is a series of images depicting the results of immunohistochemistry (IHC) studies performed using cells presenting a CAR comprising the anti-CD19 scFv FMC63; the left figure demonstrates the specific binding of antibody Clone 7 to the CAR, while the right figure demonstrates the specific binding of antibody Clone 13 to the CAR.

FIGS. 4A and 4B are a series of photographs depicting the results of immunohistochemistry (IHC) studies performed using cells presenting a CAR comprising the anti-CD19 scFv FMC63; FIG. 4A demonstrates the specific binding of antibody Clones 7 and 13 to the CAR, while FIG. 4B demonstrates the results for both antibodies using a PBMC control.

FIG. 5 is a series of sequences showing the coding and amino acid sequences for the VH region of Clone 7, the full length heavy chain amino acid sequence, and the heavy chain CDR1, CDR 2 and CDR 3 amino acid sequences for this clone.

FIG. 6 is a series of sequences showing the coding and amino acid sequences for the VL region of Clone 7, the full length light chain amino acid sequence, and the light chain CDR1, CDR 2 and CDR 3 amino acid sequences for this clone.

FIG. 7 is a series of sequences showing the coding and amino acid sequences for the VH region of Clone 13, the full length heavy chain amino acid sequence and the heavy chain CDR1, CDR 2 and CDR 3 amino acid sequences for this clone.

FIG. 8 is a series of sequences showing the coding and amino acid sequences for the VL region of Clone 13, the full length light chain amino acid sequence and the light chain CDR1, CDR 2 and CDR 3 amino acid sequences for this clone.

FIG. 9 is a series of sequences showing the coding and amino acid sequences for the VH region of Clone 14-1, the full length heavy chain amino acid sequence and the heavy chain CDR1, CDR 2 and CDR 3 amino acid sequences for this clone.

FIG. 10 is a series of sequences showing the coding and amino acid sequences for the VL region of Clone 14-1, the full length light chain amino acid sequence and the light chain CDR1, CDR 2 and CDR 3 amino acid sequences for this clone.

FIG. 11 is a series of sequences showing the coding and amino acid sequences for the VH region of Clone 14-7, the full length heavy chain amino acid sequence and the heavy chain CDR1, CDR 2 and CDR 3 amino acid sequences for this clone.

FIG. 12 is a series of sequences showing the coding and amino acid sequences for the VL region of Clone 14-7, the full length light chain amino acid sequence and the light chain CDR1, CDR 2 and CDR 3 amino acid sequences for this clone.

FIG. 13 is a series of sequences showing the coding and amino acid sequences for the VH region of Clone 15, the full length heavy chain amino acid sequence and the heavy chain CDR1, CDR 2 and CDR 3 amino acid sequences for this clone.

FIG. 14 is a series of sequences showing the coding and amino acid sequences for the VL region of Clone 15, the full length light chain amino acid sequence and the light chain CDR1, CDR 2 and CDR 3 amino acid sequences for this clone.

FIG. 15 is a series of sequences showing the coding and amino acid sequences for the VH region of Clone 17, the full length heavy chain amino acid sequence and the heavy chain CDR1, CDR 2 and CDR 3 amino acid sequences for this clone.

FIG. 16 is a series of sequences showing the coding and amino acid sequences for the VL region of Clone 17, the full length light chain amino acid sequence and the light chain CDR1, CDR 2 and CDR 3 amino acid sequences for this clone.

FIG. 19 is a table showing the CDR1, CDR2 and CDR3 sequences of the heavy and light chains of the six distinct antibodies identified, assigned based on the Kabat numbering scheme.

FIG. 20 is a table showing the CDR1, CDR2 and CDR3 sequences of the heavy and light chains of the six distinct antibodies identified, assigned based on the Chothia numbering scheme.

FIG. 21 is a table showing the CDR1, CDR2 and CDR3 sequences of the heavy and light chains of the six distinct antibodies identified, assigned based on the IMGT numbering scheme.

DETAILED DESCRIPTION OF THE INVENTION

Figure 1A:
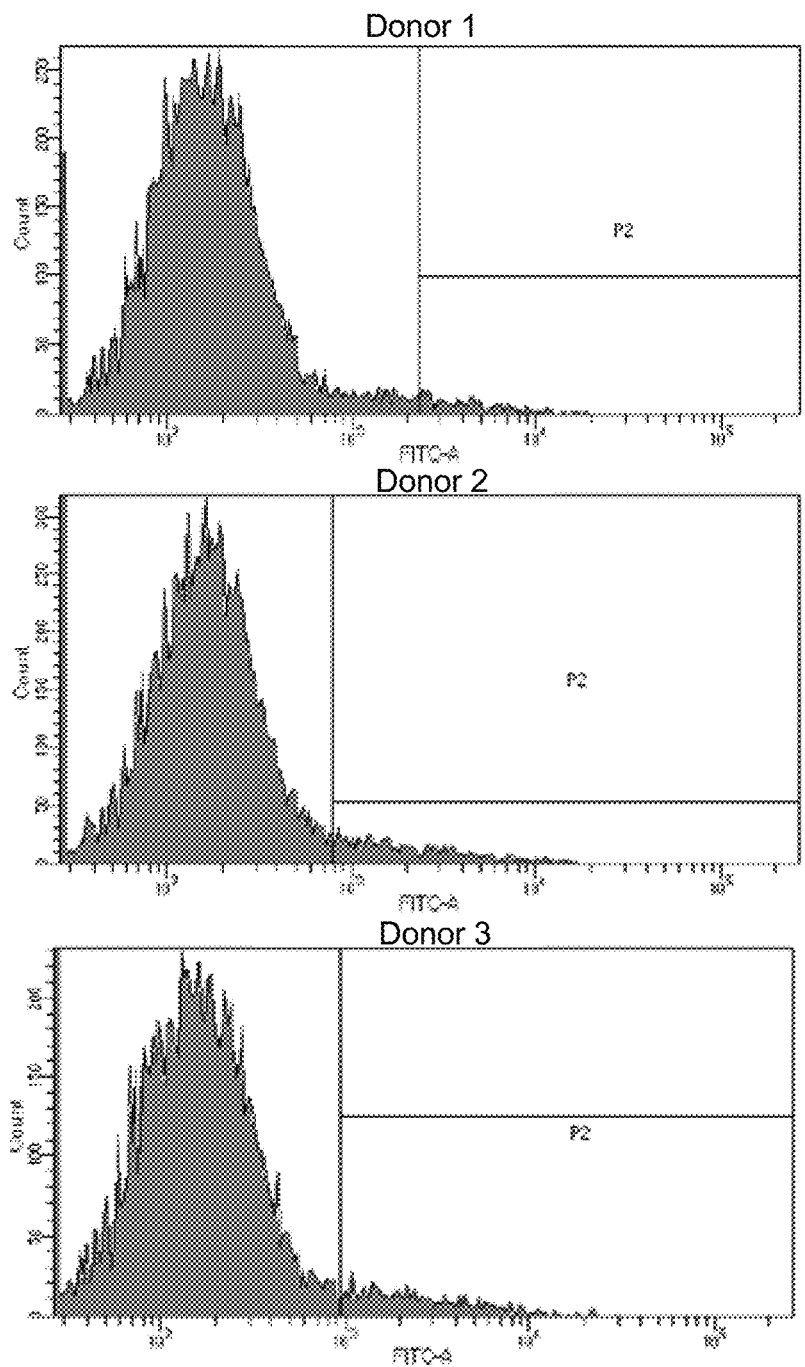
FIGS. 1A and 1B are a series of plots showing the results of flow cytometry experiments performed using untransduced cells (FIG. 1A) and cells transduced with a construct encoding a CAR comprising the anti-CD19 scFv FMC63 (FIG. 1B) and then contacted with anti-scFv antibodies corresponding to three different parental clones (Clone 14, Clone 15 and Clone 17); the plots demonstrate specific binding of the antibodies to the expressed CAR.

The present invention relates to anti-idiotypic antigen binding molecules, including antibodies, which specifically bind to antigen binding molecules that specifically bind the amino acid sequence of the anti-CD19 scFv FMC63 (see, Nicholson et al., (1997) *Mol Immunol* 34(16-17):1157-65).

The anti-CD19 scFv FMC63 has the amino acid sequence:

```
                                    (SEQ ID NO: 1)
DIQMTQTTSSLSASLGDRVTISCRASQDISKYLNWYQQKPDGT

VKLLIYHTSRLHSGVPSRFSGSGSGTDYSLTISNLEQEDIATYF

CQQGNTLPYTFGGGTKLEITGSTSGSGKPGSGEGSTKGEVKLQ

ESGPGLVAPSQSLSVTCTVSGVSLPDYGVSWIRQPPRKGLEWL

GVIWGSETTYYNSALKSRLTIIKDNSKSQVFLKMNSLQTDDTA

IYYCAKHYYYGGSYAMDYWGQGTSVTVSS
```

Humanized forms of the antigen binding molecules, molecules comprising the anti-CD19 scFv FMC63 and cells presenting a molecule comprising the anti-CD19 scFv FMC63 are also provided. Additionally, polynucleotides encoding the antigen binding molecules, as well as vectors comprising the polynucleotides, and in vitro cells comprising the polynucleotides and vectors, are also disclosed.

Methods of using the disclosed antigen binding molecules are provided. The antigen binding molecules, polynucleotides, vectors, in vitro cells and methods described herein can be used in a range of applications, e.g., as reagents to detect the presence of moieties comprising the anti-CD19 scFv FMC63, as well as molecules comprising this sequence and cells presenting such molecules, quantifying the amount of a moiety comprising anti-CD19 scFv FMC63, as well as molecules comprising this sequence and cells presenting such molecules, screening for moieties comprising the anti-CD19 scFv FMC63, as well as molecules comprising this sequence and cells presenting such molecules, purifying moieties comprising the anti-CD19 scFv FMC63, as well as molecules comprising this sequence and cells presenting such molecules, and biomarker studies focused on moieties comprising the anti-CD19 scFv FMC63, as well as molecules comprising this sequence and cells presenting such molecules. Therapeutic uses are also provided, for example applications in which the biological activity of a moiety comprising the anti-CD19 scFv FMC63, as well as cells presenting such molecules, is modulated (enhanced or repressed), as well as dose ranging studies related to therapeutics comprising the anti-CD19 scFv FMC63, as well as molecules comprising this sequence and cells presenting such molecules, and cells presenting such molecules.

The antigen binding molecules (antibodies) disclosed herein were generated from hybridomas generated using B-cells of rabbit origin, but can be readily humanized using standard methods known to those of skill in the art, as well as those described herein. Representative humanized forms of the disclosed antigen binding molecules can be generated as described herein.

I. Definitions

In order that the present disclosure may be more readily understood, certain terms are first defined. As used in this application, except as otherwise expressly provided herein, each of the following terms shall have the meaning set forth below. Additional definitions are set forth throughout the application. The headings provided herein are not limitations of the various aspects of the disclosure, which aspects should be understood by reference to the specification as a whole.

It is understood that, wherever aspects are described herein with the language "comprising," otherwise analogous aspects described in terms of "consisting of" and/or "consisting essentially of" are also provided.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, *The Concise Dictionary of Biomedicine and Molecular Biology*, 2$^{nd}$ ed., (2001), CRC Press; *The Dictionary of Cell & Molecular Biology*, 5$^{th}$ ed., (2013), Academic Press; and *The Oxford Dictionary Of Biochemistry And Molecular Biology*, Cammack et al. eds., 2$^{nd}$ ed, (2006), Oxford University Press, provide those of skill in the art with a general dictionary for many of the terms used in this disclosure.

As used herein, the twenty conventional (e.g., naturally occurring) amino acids and their abbreviations follow conventional usage. See, e.g., *Immunology—A Synthesis* (2nd Edition), Golub and Green, eds., Sinauer Assoc., Sunderland, Mass. (1991), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present invention. Examples of unconventional amino acids include: 4-hydroxyproline, gamma-carboxyglutamate, epsilon-N,N,N-trimethyllysine, e-N-acetyllysine, O-phosphoserine, N-acetylserine, N-formylmethionine, 3-methylhistidine, 5-hydroxylysine, sigma-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term the terms "a" and "an" are used per standard convention and mean one or more, unless context dictates otherwise.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. Alternatively, "about" or "comprising essentially of" can mean a range of up to 10% (i.e., ±10%). For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

As used herein, the term "and/or" is to be understood as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or," as used in a phrase such as 'A, B, and/or C" is intended to encompass each of the following aspects: A, B, and C; A, B, or C; A or C; A or B; B or C; A and C; A and B; B and C; A (alone); B (alone); and C (alone).

As used herein, the term the use of the alternative (e.g., "or") should be understood to mean either one, both, or any combination thereof of the alternatives.

As used herein, the term "allogeneic" refers to any material derived from one individual which is then introduced to another individual of the same species, e.g., allogeneic T cell transplantation.

As used herein, the term "antibody" (Ab) includes, without limitation, a glycoprotein immunoglobulin which binds specifically to an antigen. In general, an antibody can comprise at least two heavy (HC) chains and two light (LC) chains interconnected by disulfide bonds, or an antigen binding molecule thereof. Each HC chain comprises a heavy chain variable region (abbreviated herein as VH) and a heavy chain constant region. The heavy chain constant region comprises three constant domains, CH1, CH2 and CH3. Each LC chain comprises a light chain variable region (abbreviated herein as VL) and a light chain constant region. The light chain constant region comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system (C1q). The term "antibody" also encompasses an intact immunoglobulin or an antigen binding portion thereof that competes with the intact antibody for specific binding, unless otherwise specified. Antigen binding portions can be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

The term "antibody" includes, both naturally occurring and non-naturally occurring (recombinantly-produced) antibodies, human and non-human antibodies, monospecific antibodies, multispecific antibodies (including bispecific antibodies), immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies (see, e.g., Stocks, (2004) *Drug Discovery Today* 9(22):960-66), antibody fusions (which term encompasses antibody-drug conjugates) and which are sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments thereof. In certain embodiments, antibodies described herein refer to polyclonal antibody populations.

A non-human antibody can be humanized using recombinant methods to reduce its immunogenicity in humans, as disclosed herein, with respect to antibodies that specifically bind the anti-CD19 scFv FMC63, as well as molecules comprising this sequence and cells presenting such molecules. Where not expressly stated, and unless the context indicates otherwise, the term "antibody" also includes an antigen-binding fragment of an antigen binding molecule of any of the aforementioned immunoglobulins, and includes a monovalent and a divalent fragment or portion, and a single chain antibody (i.e., a scFv).

In various embodiments, an antibody specifically binds the anti-CD19 scFv FMC63 (SEQ ID NO: 1), as well as molecules comprising this sequence and cells presenting such molecules. In some embodiments, the antibody specifically binds to a CAR (or component thereof) comprising SEQ ID NO: 1, as well as molecules comprising this sequence, and cells presenting such molecules; cells presenting SEQ ID NO: 1 can, but need not be, an immune cell, such as a T cell.

As used herein, the term "antigen" means any molecule that provokes an immune response or is capable of being bound by an antibody or other antigen binding molecule. The immune response can involve either antibody production, or the activation of specific immunologically-competent cells, or both. Those of skill in the art will readily understand that any macromolecule, including virtually all proteins or peptides (including the anti-CD19 scFv FMC63; SEQ ID NO: 1), as well as molecules comprising this sequence and cells presenting such molecules), can serve as an antigen. Generally, an antigen can be endogenously expressed, i.e. expressed by genomic DNA, or it can be recombinantly expressed, or it can be chemically synthesized. In one particular embodiment, an antigen comprises all or a portion of the anti-CD19 scFv FMC63, as well as molecules comprising this sequence, which is optionally conjugated to an adjuvant such as keyhole limpet hemocyanin (KLH), or to an Fc to facilitate screening.

As used herein, the term "antigen binding molecule" means a protein comprising a portion that binds to an antigen or target protein and, optionally, a scaffold or framework portion that allows the antigen binding portion to adopt a conformation that promotes binding of the antigen binding molecule to the antigen. Examples of the representative types of antigen binding molecules include a scFv, a human, mouse or rabbit antibody; a humanized antibody; a chimeric antibody; a recombinant antibody; a single chain antibody; a diabody; a triabody; a tetrabody; a Fab fragment; a F(ab')2 fragment; an IgD antibody; an IgE antibody; an IgM antibody; an IgG1 antibody; an IgG2 anti-body; an IgG3 antibody; or an IgG4 antibody, and fragments thereof.

An antigen binding molecule can comprise, for example, an alternative protein scaffold or artificial scaffold with grafted complementarity determining regions (CDRs) or CDR derivatives. Such scaffolds include, but are not limited to, antibody-derived scaffolds comprising mutations introduced to, for example, stabilize the three-dimensional structure of the antigen binding molecule as well as wholly synthetic scaffolds comprising, for example, a biocompatible polymer. See, e.g., Korndorfer et al., 2003, *Proteins: Structure, Function, and Bioinformatics*, 53(1):121-129 (2003); Roque et al., *Biotechnol. Prog.* 20:639-654 (2004). In addition, peptide antibody mimetics ("PAMs") can be used, as well as scaffolds based on antibody mimetics utilizing various components (e.g., fibronectin) as a scaffold. An antigen binding molecule can have, for example, the structure of a naturally occurring immunoglobulin.

An antigen binding molecule can have one or more binding sites. If there is more than one binding site, the binding sites can be identical to one another or they can be different. For example, a naturally occurring human immunoglobulin typically has two identical binding sites, while a "bispecific" or "bifunctional" antibody has two different binding sites, and is capable of specifically binding two different antigens (e.g., the anti-CD19 scFv FMC63 and a cell surface activator molecule).

In various embodiments, an antigen binding molecule is an antibody or fragment thereof, including one or more of the complementarity determining regions (CDRs) disclosed herein and shown in FIGS. 5-21, which specifically bind the anti-CD19 scFv FMC63, as well as molecules comprising the anti-CD19 scFv FMC63, and cells presenting such molecules. In further embodiments, the antigen binding molecule binds to a CAR comprising the anti-CD19 scFv FMC63, as well as molecules comprising the anti-CD19 scFv FMC63, and can be expressed on an immune cell, such as a T cell.

The term "autologous" refers to any material derived from the same individual to which it is later to be re-introduced. For example, the engineered autologous cell therapy (eACT™) methods described herein involve collection of lymphocytes from a patient, which are then engineered to express a construct, e.g., a CAR construct, and then administered back to the same patient.

As used herein, the term "binding affinity" means the strength of the sum total of non-covalent interactions between a single binding site of a molecule (e.g., an antigen binding molecule such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by standard techniques known to one of ordinary skill in the art, such as BIAcore® or KinExA or surface plasmon resonance.

As used herein, the term "complementarity determining region" or "CDR" means an amino acid sequence that contributes to antigen binding specificity and affinity. Framework regions can aid in maintaining the proper confirmation of the CDRs to promote binding between the antigen binding molecule and an antigen. A number of definitions of the CDRs are commonly in use: Kabat numbering, Chothia numbering, AbM numbering, or contact numbering. The AbM definition is a compromise between the Kabat and Chothia systems, and is used by Oxford Molecular's AbM antibody modelling software. Table A defines CDRs using each numbering system. The contact definition is based on an analysis of the available complex crystal structures.

TABLE A

| Loop | Kabat | AbM | Chothia | Contact |
| --- | --- | --- | --- | --- |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B | H26--H35B | H26--H32..34 | H30--H35B |
| H1 | H31--H35 | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen binding molecule thereof. In certain aspects, the CDRs of an antibody can be determined according to the Kabat numbering system (see, e.g., Kabat et al. in Sequences of *Proteins of Immunological Interest*, 5th Ed., NIH Publication 91-3242, Bethesda Md. 1991). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In some embodiments, the CDRs of the antibodies described herein can be described according to the Kabat numbering scheme, as shown in FIG. 6 (although they can readily be construed in other numbering systems using Table A above).

In certain aspects, the CDRs of an antibody can be determined according to the Chothia numbering scheme, which refers to the location of immunoglobulin structural loops (see, e.g., Chothia C & Lesk A M, (1987), *J Mol Biol* 196: 901-917; Al-Lazikani B et al., (1997) *J Mol Biol* 273: 927-948; Chothia C et al., (1992) *J Mol Biol* 227: 799-817; Tramontano A et al., (1990) *J Mol Biol* 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). See Table A. In some embodiments, the CDRs of the antibodies described herein have been determined according to the Chothia numbering scheme, as shown in FIG. 20.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen binding molecule provided herein (or fragment thereof) can be replaced with an amino acid residue with a similar side chain.

Conservative amino acid substitutions, which are encompassed by the present disclosure, can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:

hydrophobic: norleucine, Met, Ala, Val, Leu, Ile;

neutral hydrophilic: Cys, Ser, Thr, Asn, Gln;

acidic: Asp, Glu;

basic: His, Lys, Arg;

residues that influence chain orientation: Gly, Pro; and aromatic: Trp, Tyr, Phe.

Non-conservative substitutions can involve the exchange of a member of one to of these classes for a member from another class. Such substituted residues can be introduced, for example, into regions of a human antibody that are homologous with non-human antibodies, or into the non-homologous regions of the molecule. Exemplary conservative amino acid substitutions are set forth in Table B below.

TABLE B

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "cross competes" means the situation in which the interaction between an antigen and a first antigen binding molecule or binding fragment thereof blocks, limits, inhibits, or otherwise reduces the ability of a reference antigen binding molecule or binding fragment thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross competes with a reference antigen binding molecule binds the same or an overlapping epitope as the reference antigen binding molecule. In other embodiments, the antigen binding molecule that cross competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., (1983) *Method Enzymol* 9:242-53); solid phase direct biotin-avidin EIA (Kirkland et al., (1986) *J Immunol* 137:3614-19); solid phase direct labeled assay, solid phase direct labeled sandwich assay (Harlow and Lane, 1988, *Antibodies, A Laboratory Manual*, Cold Spring Harbor Press); solid phase direct label RIA using $I^{125}$ label (Morel et al., (1988) *Molec Immunol* 25:7-15); solid phase direct biotin-avidin EIA (Cheung et al., (1990) *Virology* 176:546-52); and direct labeled RIA (Moldenhauer et al., (1990) *Scand J Immunol* 32:77-82).

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding molecule (a derivative) can have a greater circulating half-life than an antigen binding molecule that is not chemically modified. In some embodiments, a derivative antigen binding molecule is covalently modified to include one or more water soluble polymer attachments, including, but not limited to, polyethylene glycol, polyoxyethylene glycol, or polypropylene glycol.

As used herein, the term "diabody" or dAB means bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., (1993) *Proc Natl Acad Sci U.S.A.* 90:6444-48, Poljak et al., (1994) *Structure* 2: 1121-23, and Perisic et al., (1994) *Structure* 2(12): 1217-26). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege et al., (1994) *Acta Crystallogr D Biol Crystallogr* 50(Pt 4): 339-350; McPherson, (1990) *Eur J Biochem* 189: 1-23; Chayen, (1997) *Structure* 5: 1269-1274; McPherson, (1976) *J Biol Chem* 251: 6300-6303). Antibody:antigen crystals can be studied using well known X-ray diffraction techniques and may be refined using computer software such as X-PLOR (Yale University, 1992, distributed by Molecular Simulations, Inc.; see, e.g., *Meth Enzymol* (1985) Vols 114 & 115, eds Wyckoff et al.), and BUSTER (Bricogne, (1993) *Acta Crystallogr D Biol Crystallogr* 49(Pt 1): 37-60; Bricogne, (1997) *Meth Enzymol* 276A: 361-423, ed. Carter; Roversi et al., (2000) *Acta Crystallogr D Biol Crystallogr* 56(Pt 10): 1316-1323). Mutagenesis mapping studies can be accomplished using any method known to one of skill in the art. See, e.g., Champe et al., (1995) *J Biol Chem* 270: 1388-94 and Cunningham & Wells, (1989) *Science* 244: 1081-85 for a description of mutagenesis techniques, including alanine and arginine scanning mutagenesis techniques.

As used herein, the term "Fab fragment" means is a monovalent fragment having the VL, VH, CL and CH domains; a "F(ab')$_2$ fragment" is a bivalent fragment having two Fab fragments linked by a disulfide bridge at the hinge region; a "Fv fragment" has the VH and VL domains of a single arm of an antibody; and a "dAb fragment" has a VH domain, a VL domain, or an antigen-binding fragment of a VH or VL domain.

As used herein, the terms "immunospecifically binds," "immunospecifically recognizes," "specifically binds," and "specifically recognizes" are analogous terms and are used interchangeably in the context of antigen binding molecules, and means that a given molecule preferentially binds to an antigen (e.g., epitope or immune complex) as such binding is understood by one skilled in the art. For example, an antigen binding molecule that specifically binds to an antigen may bind to other peptides or polypeptides, but with a comparatively lower affinity as determined by, e.g., immunoassays, BIAcore®, KinExA 3000 instrument (Sapidyne Instruments, Boise, Id.), or other assays known in the art. In some embodiments, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, molecules that specifically bind to an antigen (e.g., the anti-CD19 scFv FMC63; SEQ ID NO: 1), as well as molecules comprising this sequence and cells presenting such molecules) bind with a dissociation constant ($K_d$) of about $1 \times 10^{-7}$ M. In some embodiments, the antigen binding molecule specifically binds an antigen (e.g., the anti-CD19 scFv FMC63, as well as molecules comprising this sequence and cells presenting such molecules) with "high affinity" when the $K_d$ is about $1 \times 10^{-9}$ M to about $5 \times 10^{-9}$ M. In some embodiments, the antigen binding molecule specifically binds an antigen (e.g., the anti-CD19 scFv FMC63, as well as molecules comprising this sequence and cells presenting such molecules) with "very high affinity" when the $K_d$ is $1 \times 10^{-10}$ M to about $5 \times 10^{-10}$ M.

In still another embodiment, molecules that specifically bind to an antigen (e.g., the anti-CD19 scFv FMC63, as well as molecules comprising this sequence and cells presenting such molecules) do not cross react with other proteins under similar binding conditions. In some embodiments, molecules that specifically bind to an antigen (e.g., the anti-CD19 scFv FMC63, as well as molecules comprising this sequence and cells presenting such molecules) do not cross react with other proteins that do not comprise the anti-CD19 scFv FMC63, molecules comprising this sequence and cells presenting such molecules. In some embodiments, provided herein is an antibody or fragment thereof that binds to the anti-CD19 scFv FMC63, as well as molecules comprising this sequence and cells presenting such molecules, with higher affinity than to another unrelated antigen. In certain embodiments, provided herein is an antigen binding molecule (e.g., an antibody) or fragment thereof that binds to the anti-CD19 scFv FMC63, as well as molecules comprising this sequence and cells presenting such molecules, with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In some embodiments, the extent of binding of an antigen binding molecule, antibody or antigen binding fragment thereof that specifically binds the anti-CD19 scFv FMC63, as well as molecules comprising this sequence and cells presenting such molecules, described herein compared to an unrelated protein which does not comprise the anti- CD19 scFv FMC63, as well as molecules comprising this sequence and cells presenting such molecules, is less than 10%, 15%, or 20% of the binding of the antibody to linker fragment protein as measured by, e.g., a radioimmunoassay.

As used herein, the term "heavy chain" when used in reference to an antibody can refer to any distinct type, e.g., alpha ($\alpha$), delta ($\delta$), epsilon ($\epsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "immunoglobulin" means an immune molecule from any of the commonly known isotypes, including but not limited to IgA, secretory IgA, IgG and IgM. IgG subclasses are also well known to those in the art and include but are not limited to human IgG1, IgG2, IgG3 and IgG4. Many of the molecules described herein are immunoglobulins. As used herein, "isotype" means the antibody class or subclass (e.g., IgM or IgG1) that is encoded by the heavy chain constant region genes.

An immunoglobulin is a tetrameric molecule, normally composed of two identical pairs of polypeptide chains, each pair having one "light" (about 25 kDa) and one "heavy" chain (about 50-70 kDa). The amino-terminal portion of each chain includes a variable region of about 100 to 130 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, or IgE, respectively. Within light and heavy chains, the variable and constant regions are joined by a "J" region of about 12 or more amino acids, with the heavy chain also including a "D" region of about 10 more amino acids. See generally, Berzofsky & Berkower, Ch. 7 in *Fundamental Immunology* (Paul, W., ed., Lippincott Williams & Wilkins (2012); which chapter and volume is incorporated by reference in its entirety for all purposes). The variable regions of each light/heavy chain pair form the antibody binding site such that an intact immunoglobulin has two primary binding sites.

Naturally occurring immunoglobulin chains exhibit the same general structure of relatively conserved framework regions (FR) joined by three hypervariable regions, also called complementarity determining regions or "CDRs." From N-terminus to C-terminus, both light and heavy chains comprise the domains FR1, CDR1, FR2, CDR2, FR3, CDR3 and FR4. The assignment of amino acids to each domain can be done in accordance with the definitions of Kabat (see, e.g., Kabat et al. in *Sequences of Proteins of Immunological Interest*, 5th Ed., NIH Publication 91-3242, Bethesda Md. (1991)) or Chothia (Chothia, used herein, (see, e.g., Chothia & Lesk (1987), *J. Mol. Biol.* 196:901-917; Chothia et al., 1989, *Nature* 342:878-883 or Honegger & Pluckthun (2001), *J Mol Biol* 309:657-670). The Kabat, Chothia, IGMT and Abm (Oxford Molecular) numbering systems are described more fully herein.

As used herein, the term "in vitro cell" refers to any cell that is cultured ex vivo. An in vitro cell can include a human cell such as a T cell or dendritic cell, or it can include CHO, sP2/0, rabbit and other non-human cells.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are known in the art. In specific embodiments, the light chain is a human light chain.

The term "neutralizing" refers to an antigen binding molecule, scFv, antibody, or a fragment thereof, that binds to a ligand (e.g., a moiety comprising the anti-CD19 scFv FMC63, as well as molecules comprising this sequence and cells presenting such molecules) and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "patient" means any human who is being treated for an abnormal physiological condition, such as cancer or has been formally diagnosed with a disorder, those without formally recognized disorders, those receiving medical attention, those at risk of developing the disorders, etc. The terms "subject" and "patient" are used interchangeably herein and include both human and non-human animal subjects.

As used herein, the terms "peptide," "polypeptide," and "protein" are used interchangeably herein, and mean a compound comprising amino acid residues covalently linked by peptide bonds. A protein or peptide must contain at least two amino acids, but no limitation is placed on the maximum number of amino acids that can comprise a protein's or peptide's sequence. The term polypeptide encompasses any peptide or protein comprising two or more amino acids joined to each other by peptide bonds. As used herein, the term refers to both short chains, which also commonly are referred to as peptides, oligopeptides and oligomers, and to longer chains, which generally are referred to as proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The term "polypeptide" includes natural peptides, recombinant peptides, synthetic peptides, or a combination thereof.

In some aspects, the polypeptides and/or proteins have deletions from, additions to, and/or substitutions of one or more amino acids of antigen binding molecule. Useful polypeptide fragments may include immunologically functional fragments of antigen binding molecules, including not limited to one or more CDR regions, variable domains of a heavy and/or light chain, a portion of other portions of an antibody chain, and the like. Moieties that can be substituted for one or more amino acids of an antigen binding molecule include, e.g., D or L forms of amino acids, an amino acid different from the amino acid normally found in the same position of an antigen binding molecule (relative to SEQ ID NOs: 2-73), deletions, non-naturally occurring amino acids, and chemical analogs of amino acids.

Peptide analogs are commonly used in the pharmaceutical industry as non-peptide drugs with properties analogous to those of the template peptide and form an aspect of the instant disclosure. These types of non-peptide compound are termed "peptide mimetics" or "peptidomimetics." See, e.g., Fauchere, (1986) *Adv. Drug Res*. (Testa, ed.) 15:29-69; Veber & Freidinger, (1985) *TINS*, p. 392; and Evans et al., (1987) *J. Med. Chem*, 30:1229-39, which are incorporated herein by reference for any purpose.

Polypeptides, peptides, proteins and analogous molecules comprising the anti-CD19 scFv FMC63, as well as molecules comprising this sequence and cells presenting such molecules, are specifically encompassed by the terms.

As used herein, the term "percent identity" means the percent of identical residues between the amino acids or nucleotides in the compared molecules. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, ed.), (1988) New York: Oxford University Press; *Biocomputing Informatics and Genome Projects*, (Smith, ed.), 1993, New York: Academic Press; *Computer Analysis of Sequence Data, Part I*, (Griffin and Griffin, eds.), 1994, New Jersey: Humana Press; von Heinje, (1987) *Sequence Analysis in Molecular Biology*, New York: Academic Press; *Sequence Analysis Primer*, (Gribskov and Devereux, eds.), 1991, New York: M. Stockton Press; and Carillo et al., (1988) *J. Applied Math.* 48:1073.

In calculating percent identity, the sequences being compared are aligned in a way that gives the largest match between the sequences. The computer program used to determine percent identity can be, e.g., MOE (Chemical Computing Group) or DNASTAR (University of Wisconsin, Madison, Wis.). The computer algorithm GAP can be used to align the two polypeptides or polynucleotides for which the percent sequence identity is to be determined. The sequences are aligned for optimal matching of their respective amino acid or nucleotide (the "matched span," as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, e.g., Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89: 10915-10919 for the BLOSUM 62 comparison matrix) is also used by the algorithm.

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if desired to result in an alignment that spans at least 50 contiguous amino acids of the target polypeptide.

As used herein, the terms "single-chain antibody" and "single chain fragment variable (scFv)" are used interchangeably and mean an antigen binding molecule in which a VL and a VH region are joined via a linker to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Natl. Acad. Sci. U.S.A.* 85:5879-83 (1988). FMC63 is a specific example of a scFv.

A "therapeutically effective amount," "effective dose," "effective amount," or "therapeutically effective dosage" of a therapeutic agent, (e.g., a moiety comprising the anti-CD19 scFv FMC63, as well as molecules comprising this sequence and cells presenting such molecules), is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Hartl and Jones (1997) "*Genetics: Principles and Analysis,*" 4$^{th}$ ed, Jones & Bartlett). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

As used herein, the terms "variable region" or "variable domain" are used interchangeably and mean a portion of an antibody, generally, a portion of a light or heavy chain, typically about the amino-terminal end of the antibody and comprising about 100-130 amino acids in the heavy chain and about 90 to 115 amino acids in the light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). The CDRs of the light and heavy chains are primarily responsible for the interaction and specificity of the antibody with antigen.

In certain embodiments, the variable region of an antigen binding molecule is a human variable region. In further embodiments, the variable region comprises rodent, human or murine CDRs and human framework regions (FRs). In further embodiments, the variable region is a primate (e.g., a non-human primate) variable region. In yet further embodiments, the variable region is a rabbit variable region. In other embodiments, the variable region comprises human CDRs and non-human (e.g., rabbit, murine, rat or non-human primate) framework regions (FRs). In other embodiments, the variable region comprises non-human (e.g., rabbit, murine, rat or non-human primate) CDRs and human framework regions (FRs).

The terms "VH," "VH domain" and "VH chain" are used interchangeably and mean the heavy chain variable region of an antigen binding molecule, antibody or an antigen binding fragment thereof.

The terms "VL," "VL domain" and "VL chain" are used interchangeably and mean the light chain variable region of an antigen binding molecule, antibody or an antigen binding fragment thereof.

Various aspects of the invention are described in further detail in the following subsections.

II. Antigen Binding Molecules and Polynucleotides Encoding the Same

The present disclosure is directed to antigen binding molecules, including antibodies, that specifically bind the anti-CD19 scFv FMC63 (SEQ ID NO: 1), as well as molecules comprising this sequence and cells presenting such molecules, and/or those which cross compete with one or more antigen binding molecules described herein (i.e., one or more of those described in FIGS. 5-21 and/or disclosed in the appended Sequence Listing). Polynucleotides encoding the antigen binding molecules are also provided, and form an aspect of the instant disclosure.

An antibody or antigen binding molecule encoded of the present invention can be single chained or double chained. In some embodiments, the antibody or antigen binding molecule is single chained. In certain embodiments, the antigen binding molecule is selected from the group consisting of an scFv, a Fab, a Fab', a Fv, a F(ab')$_2$, a dAb, and any combination thereof. In one particular embodiment, the antibody or antigen binding molecule comprises an scFv.

In certain embodiments, an antigen binding molecule such as an antibody comprises a single chain, wherein the heavy chain variable region and the light chain variable region are connected by a linker (e.g., an scFv). In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises between about 8 amino acids and about 18 amino acids (e.g., 10 amino acids).

In some embodiments, the antigen binding molecules of the present invention specifically bind to the anti-CD19 scFv FMC63, as well as molecules comprising this sequence and cells presenting such molecules. In certain embodiments, an antigen binding molecule of the present disclosure specifically binds the anti-CD19 scFv FMC63, as well as molecules comprising this sequence and cells presenting such molecules with a $K_D$ of less than $1 \times 10^{-6}$ M, less than $1 \times 10^{-7}$ M, less than $1 \times 10^{-8}$ M, or less than $1 \times 10^{-9}$ M. In one particular embodiment, an antigen binding molecule specifically binds to the anti-CD19 scFv FMC63, as well as molecules comprising this sequence and cells presenting such molecules, with a $K_D$ of less than $1 \times 10^{-7}$ M. In another embodiment, an antigen binding molecule specifically binds the anti-CD19 scFv FMC63, as well as molecules comprising this sequence and cells presenting such molecules, with a $K_D$ of less than $1 \times 10^{-8}$ M. In some embodiments, an antigen binding molecule binds the anti-CD19 scFv FMC63, as well as molecules comprising this sequence and cells presenting such molecules, with a $K_D$ of about $1 \times 10^{-7}$ M, about $2 \times 10^{-7}$ M, about $3 \times 10^{-7}$ M, about $4 \times 10^{-7}$ M, about $5 \times 10^{-7}$ M, about $6 \times 10^{-7}$ M, about $7 \times 10^{-7}$ M, about $8 \times 10^{-7}$ M, about $9 \times 10^{-7}$ M, about $1 \times 10^{-8}$ M, about $2 \times 10^{-8}$ M, about $3 \times 10^{-8}$ M, about $4 \times 10^{-8}$ M, about $5 \times 10^{-8}$ M, about $6 \times 10^{-8}$ M, about $7 \times 10^{-8}$ M, about $8 \times 10^{-8}$ M, about $9 \times 10^{-8}$ M, about $1 \times 10^{-9}$ M, about $2 \times 10^{-9}$ M, about $3 \times 10^{-9}$ M, about $4 \times 10^{-9}$ M, about $5 \times 10^{-9}$ M, about $6 \times 10^{-9}$ M, about $7 \times 10^{-9}$ M, about $8 \times 10^{-9}$ M, about $9 \times 10^{-9}$ M, about $1 \times 10^{-10}$ M, or about $5 \times 10^{-10}$ M. $K_D$ can be calculated using standard methodologies, as described herein.

In specific embodiments, an antigen binding molecule of the instant disclosure is an antibody identified herein as Clone 7, Clone 13, Clone 14-1, Clone 14-7, Clone 15, or Clone 17, and each comprises the following heavy and light chain amino acid, coding, variable, and CDR sequences, as provided and labeled:

```
Clone 7 VH DNA
                                                         (SEQ ID NO: 2)
ATGGAGACTGGGCTGCGCTGGCTTCTCCTGGTCGCTGTGCTCAAAGGTGT

CCAGTGTCAGGAGCAGCTGGAGGAGTCCGGGGGAGACCTGGTCAAGCCT

GGAGGAACCCTGACAGTCACCTGCAAAGCCTCTGGATTCTCCTTCAGTA

ACAATGGAATTTGCTGGGTCCGCCAGGCTCCAGGGAAGGGGCTGGAGTG

GATCGGATGTCTTTATGTTGGTAGTAGTGATACCACTTACTACGCGAGCT

GGGCGAAAGGCCGATTCACCATCTCCAAAAGCTCGTCGACCACGGTGAC

TCTACAAATGACCAGTCTGACAGTCGCGGACACGGCCACCTATTTCTGTA

CGATAAATCTCGGCTTGTGGGCCCCGGCACCCTGGTCACCGTCTCCTCA

Clone 7 VH AA (CDRs underlined)
                                                         (SEQ ID NO: 3)
METGLRWLLLVAVLKGVQCQEQLEESGGDLVKPGGTLTVTCKASGFSFSN

NGICWVRQAPGKGLEWIGCLYVGSSDTTYYASWAKGRFTISKSSSTTVTLQ

MTSLTVADTATYFCTINLGLWGPGTLVTVSS

Clone 7 HC AA (CDRs underlined)
                                                         (SEQ ID NO: 4)
METGLRWLLLVAVLKGVQCQEQLEESGGDLVKPGGTLTVTCKASGFSFSN

NGICWVRQAPGKGLEWIGCLYVGSSDTTYYASWAKGRFTISKSSSTTVTLQ

MTSLTVADTATYFCTINLGLWGPGTLVTVSSGQPKAPSVFPLAPCCGDTPSS

TVTLGCLVKGYLPEPVTVTWNSGTLTNGVRTFPSVRQSSGLYSLSSVVSVTS
```

```
SSQPVTCNVAHPATNTKVDKTVAPSTCSKPTCPPPELLGGPSVFIFPPKPKDT

LMISRTPEVTCVVVDVSQDDPEVQFTWYINNEQVRTARPPLREQQFNSTIRV

VSTLPIAHQDWLRGKEFKCKVHNKALPAPIEKTISKARGQPLEPKVYTMGPP

REELSSRSVSLTCMINGFYPSDISVEWEKNGKAEDNYKTTPAVLDSDGSYFL

YSKLSVPTSEWQRGDVFTCSVMHEALHNHYTQKSISRSPGK

Clone 7 VH CDR1 AA
                                                   (SEQ ID NO: 5)
GFSFSNN Clone 7 VH CDR2 AA
                                                   (SEQ ID NO: 6)
YVGSSD Clone 7 VH CDR3 AA
                                                   (SEQ ID NO: 7)
NLGL Clone 7 VL DNA
                                                   (SEQ ID NO: 8)
ATGGACACGAGGGCCCCCACTCAGCTGCTGGGGCTCCTGCTGCTCTGGCT

CCCAGGTGCCACATTTGCCATCGTGGTGACCCAGACTCCATCTTCCAAGT

CTGTCCCTGTGGGAGGCACAGTCACCATCAATTGCCAGGCCAGTGAGAG

TGTTTATAATAGCGACTGGTTAGCCTGGTATCAGCAGAAACCAGGGCAG

CCTCCCAAGCAACTGATCTATGCTGCATCCACTCTGGCATCTGGGGTCCC

ATCGCGCTTCAAAGGCAGTGGATCTGGGACACAGTTCACTCTCACCATC

AGCGATGTGGTGTGTGACGATGCTGCCACTTATTATTGTGCAGGATATAA

AAGTAGTAGTACTGATGGGATTGCTTTCGGCGGAGGGACCGAGGTGGTG

GTCAAA

Clone 7 VL AA (CDRs underlined)
                                                   (SEQ ID NO: 9)
MDTRAPTQLLGLLLLWLPGATFAIVVTQTPSSKSVPVGGTVTINCQASESVY

NSDWLAWYQQKPGQPPKQLIYAASTLASGVPSRFKGSGSGTQFTLTISDVV

CDDAATYYCAGYKSSSTDGIAFGGGTEVVVK

Clone 7 LC AA (CDRs underlined)
                                                   (SEQ ID NO: 10)
MDTRAPTQLLGLLLLWLPGATFAIVVTQTPSSKSVPVGGTVTINCQASESVY

NSDWLAWYQQKPGQPPKQLIYAASTLASGVPSRFKGSGSGTQFTLTISDVV

CDDAATYYCAGYKSSSTDGIAFGGGTEVVVKGDPVAPTVLIFPPAADQVAT

GTVTIVCVANKYFPDVTVTWEVDGTTQTTGIENSKTPQNSADCTYNLSSTLT

LTSTQYNSHKEYTCKVTQGTTSVVQSFNRGDC

Clone 7 VL CDR1 AA
                                                   (SEQ ID NO: 11)
QASESVYNSDWLA Clone 7 VL CDR2 AA
                                                   (SEQ ID NO: 12)
AASTLAS Clone 7 VL CDR3 AA
                                                   (SEQ ID NO: 13)
AGYKSSSTDGIA Clone 13 VH DNA
                                                   (SEQ ID NO: 14)
ATGGAGACTGGGCTGCGCTGGCTTCTCCTGGTCGCTGTGCTCAAAGGTGT

CCAGTGTCAGGAGCAGCTGGAGGAGTCCGGGGGAGACCTGGTCAAGCCT
```

```
GGAGGAACCCTGACAGTCACCTGCAAAGCCTCTGGATTCTCCTTCAGTA

ACAATGGAATTTGCTGGGTCCGCCAGGCTCCAGGGAAGGGGCTGGAGTG

GATCGGATGTCTTTATGTTGGTAGTAGTGATACCACTTACTACGCGAGCT

GGGCGAAAGGCCGATTCACCATCTCCAAAAGCTCGTCGACCACGGTGAC

TCTACAAATGACCAGTCTGACAGTCGCGGACACGGCCACCTATTTCTGTA

CGATAAATCTCGGCTTGTGGGGCCCCGGCACCCTGGTCACCGTCTCCTCA
```

Clone 13 VH AA (CDRs underlined)
(SEQ ID NO: 15)
METGLRWLLLVAVLKGVQCQEQLEESGGDLVKPGGTLTVTCKAS<u>GFSFSN</u>

<u>N</u>GICWVRQAPGKGLEWIGCL<u>YVGSSD</u>TTYYASWAKGRFTISKSSSTTVTLQ

MTSLTVADTATYFCTI<u>NLGL</u>WGPGTLVTVSS

Clone 13 HC AA (CDRs underlined)
(SEQ ID NO: 16)
METGLRWLLLVAVLKGVQCQEQLEESGGDLVKPGGTLTVTCKAS<u>GFSFSN</u>

<u>N</u>GICWVRQAPGKGLEWIGCL<u>YVGSSD</u>TTYYASWAKGRFTISKSSSTTVTLQ

MTSLTVADTATYFCTI<u>NLGL</u>WGPGTLVTVSSGQPKAPSVFPLAPCCGDTPSS

TVTLGCLVKGYLPEPVTVTWNSGTLTNGVRTFPSVRQSSGLYSLSSVVSVTS

SSQPVTCNVAHPATNTKVDKTVAPSTCSKPTCPPPELLGGPSVFIFPPKPKDT

LMISRTPEVTCVVVDVSQDDPEVQFTWYINNEQVRTARPPLREQQFNSTIRV

VSTLPIAHQDWLRGKEFKCKVHNKALPAPIEKTISKARGQPLEPKVYTMGPP

REELSSRSVSLTCMINGFYPSDISVEWEKNGKAEDNYKTTPAVLDSDGSYFL

YSKLSVPTSEWQRGDVFTCSVMHEALHNHYTQKSISRSPGK

Clone 13 VH CDR1 AA
(SEQ ID NO: 5)
GFSFSNN

Clone 13 VH CDR2 AA
(SEQ ID NO: 6)
YVGSSD

Clone 13 VH CDR3 AA
(SEQ ID NO: 7)
NLGL

Clone 13 VL DNA
(SEQ ID NO: 17)
```
ATGGACACGAGGGCCCCCACTCAGCTGCTGGGGCTCCTGCTGCTCTGGCT

CCCAGGTGCCACACTTGCCATCGTGGTGACCCAGACTCCATCTTCCAAGT

CTGTCCCTGTGGGAGGCACAGTCACCATCAATTGCCAGGCCAGTGAGAG

TGTTTATAATAGCGACTGGTTAGCCTGGTATCAGCAGAAACCAGGGCAG

CCTCCCAAGCAACTGATCTATGCTGCATCCACTCTGGCATCTGGGGTCCC

ATCGCGCTTCAAAGGCAGTGGATCTGGGACACAGTTCACTCTCACCATC

AGCGATGTGGTGTGTGACGATGCTGCCACTTATTATTGTGCAGGATATAA

AAGTAGTAGTACTGATGGGATTGCTTTCGGCGGAGGGACCGAGGTGGTG

GTCAAA
```

Clone 13 VL AA (CDRs underlined)
(SEQ ID NO: 18)
MDTRAPTQLLGLLLLWLPGATLAIVVTQTPSSKSVPVGGTVTINC<u>QASESVY</u>

<u>NSDWLA</u>WYQQKPGQPPKQLIY<u>AASTLAS</u>GVPSRFKGSGSGTQFTLTISDVV

CDDAATYYC<u>AGYKSSSTDGIA</u>FGGGTEVVVK

Clone 13 LC AA (CDRs underlined)

```
                                                          (SEQ ID NO: 19)
MDTRAPTQLLGLLLLWLPGATLAIVVTQTPSSKSVPVGGTVTINCQASESVY

NSDWLAWYQQKPGQPPKQLIYAASTLASGVPSRFKGSGSGTQFTLTISDVV

CDDAATYYCAGYKSSSTDGIAFGGGTEVVVKGDPVAPTVLIFPPAADQVAT

GTVTIVCVANKYFPDVTVTWEVDGTTQTTGIENSKTPQNSADCTYNLSSTLT

LTSTQYNSHKEYTCKVTQGTTSVVQSFNRGDC

Clone 13 VL CDR1 AA
                                                          (SEQ ID NO: 11)
QASESVYNSDWLA Clone 13 VL CDR2 AA
                                                          (SEQ ID NO: 12)
AASTLAS Clone 13 VL CDR3 AA
                                                          (SEQ ID NO: 13)
AGYKSSSTDGIA Clone 14-1 VH DNA
                                                          (SEQ ID NO: 20)
ATGGAGACTGGGCTGCGCTGGCTTCTCCTGGTCGCTGTGCTCAAAGGTGT

CCAGTGTCAGGAGCAGCTGGAGGAGTCCGGGGGAGGCCTGGTCAAGCCT

GGGGCATCCCTGACACTCACCTGCAAAGCCTCTGGATTCGACTTCAGTAT

CAACTACTACATGTGCTGGGTCCGCCAGGCTCCAGGGAAGGGGTTGGAG

TGGATCGCATGCATTTATACTGGTGATGATGACACTTTCTACGCGAGCTG

GGCGAAAGGCCGGTTCACCATCTCCAAAACCTCGTCGACCACGGTGACT

CTACAACTGAACAGTCTGACAGCCGCGGACACGGCCACCTATTTCTGTGT

GAGAGGTCTATATAGTGGTAGTATTAATAACCTGTGGGGCCCAGGCACC

CTGGTCACCGTCTCCTCA

Clone 14-1 VH AA (CDRs underlined)
                                                          (SEQ ID NO: 21)
METGLRWLLLLVAVLKGVQCQEQLEESGGGLVKPGASLTLTCKASGFDFSIN

YYMCWVRQAPGKGLEWIACIYTGDDDTFYASWAKGRFTISKTSSTTVTLQL

NSLTAADTATYFCVRGLYSGSINNLWGPGTLVTVSS

Clone 14-1 HC AA (CDRs underlined)
                                                          (SEQ ID NO: 22)
METGLRWLLLLVAVLKGVQCQEQLEESGGGLVKPGASLTLTCKASGFDFSIN

YYMCWVRQAPGKGLEWIACIYTGDDDTFYASWAKGRFTISKTSSTTVTLQL

NSLTAADTATYFCVRGLYSGSINNLWGPGTLVTVSSGQPKAPSVFPLAPCCG

DTPSSTVTLGCLVKGYLPEPVTVTWNSGTLTNGVRTFPSVRQSSGLYSLSSV

VSVTSSSQPVTCNVAHPATNTKVDKTVAPSTCSKPTCPPPELLGGPSVFIFPP

KPKDTLMISRTPEVTCVVVDVSQDDPEVQFTWYINNEQVRTARPPLREQQF

NSTIRVVSTLPIAHQDWLRGKEFKCKVHNKALPAPIEKTISKARGQPLEPKV

YTMGPPREELSSRSVSLTCMINGFYPSDISVEWEKNGKAEDNYKTTPAVLDS

DGSYFLYSKLSVPTSEWQRGDVFTCSVMHEALHNHYTQKSISRSPGK

Clone 14-1 VH CDR1 AA
                                                          (SEQ ID NO: 23)
GFDFSINY Clone 14-1 VH CDR2 AA
                                                          (SEQ ID NO: 24)
YTGDD Clone 14-1 VH CDR3 AA
                                                          (SEQ ID NO: 25)
```

GLYSGSINNL

Clone 14-1 VL DNA
(SEQ ID NO: 26)
ATGGACACGAGGGCCCCCACTCAGCTGCTGGGGCTCCTGCTGCTCTGGCT

CCCAGATGCCAGATGTGCGCTTGTGATGACCCAGACTCCATCCCCTGTGT

CTGCAGCTGTGGGAGGCACAGTCACCATCAGTTGCCAGGCCAGTCAGAG

TGTTTATAACAACGACTACTTATCCTGGTATCAGCAGAAACCAGGGCAG

CCTCCCAAACTCCTGATCTATTATGCATCCACTCTGGCATCTGGGGTCTC

ATCGCGGTTCAAAGGCAGTGGATCTGGGACACAGTTCACTCTCACCATC

AGCGACGTGCAGTGTGACGATGCTGCCGCTTACTATTGTGCAGGCGTTA

AAGGTTATAGTAATGATAATAATGGTTTCGGCGGAGGGACCGAGGTGGT

GGTCAAA

Clone 14-1 VL AA (CDRs underlined)
(SEQ ID NO: 27)
MDTRAPTQLLGLLLLWLPDARCALVMTQTPSPVSAAVGGTVTISC<u>QASQSV YNNDYLS</u>WYQQKPGQPPKLLIY<u>YASTLAS</u>GVSSRFKGSGSGTQFTLTISDVQ CDDAAAYYC<u>AGVKGYSNDNNG</u>FGGGTEVVVK Clone 14-1 LC AA (CDRs underlined)
(SEQ ID NO: 28)
MDTRAPTQLLGLLLLWLPDARCALVMTQTPSPVSAAVGGTVTISC<u>QASQSV YNNDYLS</u>WYQQKPGQPPKLLIY<u>YASTLAS</u>GVSSRFKGSGSGTQFTLTISDVQ CDDAAAYYC<u>AGVKGYSNDNNG</u>FGGGTEVVVKGDPVAPTVLIFPPAADQVA

TGTVTIVCVANKYFPDVTVTWEVDGTTQTTGIENSKTPQNSADCTYNLSSTL

TLTSTQYNSHKEYTCKVTQGTTSVVQSFNRGDC

Clone 14-1 VL CDR1 AA
(SEQ ID NO: 29)
QASQSVYNNDYLS

Clone 14-1 VL CDR2 AA
(SEQ ID NO: 30)
YASTLAS

Clone 14-1 VL CDR3 AA
(SEQ ID NO: 31)
AGVKGYSNDNNG

Clone 14-7 VH DNA
(SEQ ID NO: 32)
ATGGAGACTGGGCTGCGCTGGCTTCTCCTGGTCGCTGTGCTCAAAGGTGT

CCAATGTCAGTCGCTGGAGGAGTCCGGGGGAGGCCTGGTCAAGCCTGGG

GCATCCCTGACACTCACCTGCAAAGCCTCTGGATTCGACTTCAGTATCAA

CTACTACATGTGCTGGGTCCGCCAGGCTCCAGGGAAGGGGTTGGAGTGG

ATCGCATGCATTTATACTGGTGATGATGACACTTTCTACGCGAGCTGGGC

GAAAGGCCGGTTCACCATCTCCAAAACCTCGTCGACCACGGTGACTCTA

CAACTGAACAGTCTGACAGCCGCGGACACGGCCACCTATTTCTGTGTGA

GAGGTCTATATAGTGGTAGTATTAATAACCTGTGGGGCCCAGGCACCCT

GGTCACCGTCTCCTCA

Clone 14-7 VH AA (CDRs underlined)
(SEQ ID NO: 33)
METGLRWLLLVAVLKGVQCQSLEESGGGLVKPGASLTLTCKAS<u>GFDFSINY</u>

YMCWVRQAPGKGLEWIAC<u>IYTGDDDTFYASWAK</u>GRFTISKTSSTTVTLQLN

SLTAADTATYFCVR<u>GLYSGSINNL</u>WGPGTLVTVSS

Clone 14-7 HC AA (CDRs underlined)
(SEQ ID NO: 34)
METGLRWLLLVAVLKGVQCQSLEESGGGLVKPGASLTLTCKAS<u>GFDFSINY</u>

YMCWVRQAPGKGLEWIACI<u>YTGDDD</u>TFYASWAKGRFTISKTSSTTVTLQLN

SLTAADTATYFCVR<u>GLYSGSINNL</u>WGPGTLVTVSSGQPKAPSVFPLAPCCGD

TPSSTVTLGCLVKGYLPEPVTVTWNSGTLTNGVRTFPSVRQSSGLYSLSSVV

SVTSSSQPVTCNVAHPATNTKVDKTVAPSTCSKPTCPPPELLGGPSVFIFPPKP

KDTLMISRTPEVTCVVVDVSQDDPEVQFTWYINNEQVRTARPPLREQQFNS

TIRVVSTLPIAHQDWLRGKEFKCKVHNKALPAPIEKTISKARGQPLEPKVYT

MGPPREELSSRSVSLTCMINGFYPSDISVEWEKNGKAEDNYKTTPAVLDSDG

SYFLYSKLSVPTSEWQRGDVFTCSVMHEALHNHYTQKSISRSPGK

Clone 14-7 VH CDR1 AA
(SEQ ID NO: 23)
GFDFSINY

Clone 14-7 VH CDR2 AA
(SEQ ID NO: 24)
YTGDD

Clone 14-7 VH CDR3 AA
(SEQ ID NO: 25)
GLYSGSINNL

Clone 14-7 VL DNA
(SEQ ID NO: 35)
ATGGACACGAGGGCCCCCACTCAGCTGCTGGGGCTCCTGCTGCTCTGGCT

CCCAGATGCCAGATGTGCGCTTGTGATGACCCAGACTCCATCCCCTGTGT

CTGCAGCTGTGGGAGGCACAGTCACCATCAGTTGCCAGGCCAGTCAGAG

TGTTTATAACAACGACTACTTATCCTGGTATCAGCAGAAACCAGGGCAG

CCTCCCAAACTCCTGATCTATTATGCATCCACTCTGGCATCTGGGGTCTC

ATCGCGGTTCAAAGGCAGTGGATCTGGGACACAGTTCACTCTCACCATC

AGCGACGTGCAGTGTGACGATGCTGCCGCTTACTATTGTGCAGGCGTTA

AAGGTTATAGTAATGATAATAATGGTTTCGGCGGAGGGACCGAGGTGGT

GGTCAAA

Clone 14-7 VL AA (CDRs underlined)
(SEQ ID NO: 36)
MDTRAPTQLLGLLLLWLPDARCALVMTQTPSPVSAAVGGTVTISC<u>QASQSV
YNNDYLS</u>WYQQKPGQPPKLLIY<u>YASTLAS</u>GVSSRFKGSGSGTQFTLTISDVQ CDDAAAYYC<u>AGVKGYSNDNNG</u>FGGGTEVVVK Clone 14-7 LC AA (CDRs underlined)
(SEQ ID NO: 37)
MDTRAPTQLLGLLLLWLPDARCALVMTQTPSPVSAAVGGTVTISC<u>QASQSV
YNNDYLS</u>WYQQKPGQPPKLLIY<u>YASTLAS</u>GVSSRFKGSGSGTQFTLTISDVQ CDDAAAYYC<u>AGVKGYSNDNNG</u>FGGGTEVVVKGDPVAPTVLIFPPAADQVA

TGTVTIVCVANKYFPDVTVTWEVDGTTQTTGIENSKTPQNSADCTYNLSSTL

TLTSTQYNSHKEYTCKVTQGTTSVVQSFNRGDC

Clone 14-7 VL CDR1 AA
(SEQ ID NO: 29)
QASQSVYNNDYLS

Clone 14-7 VL CDR2 AA
(SEQ ID NO: 30)
YASTLAS

-continued

Clone 14-7 VL CDR3 AA
(SEQ ID NO: 31)
AGVKGYSNDNNG

Clone 15 VH DNA
(SEQ ID NO: 38)
ATGGAGACTGGGCTGCGCTGGCTTCTCCTGGTCGCTGTGCTCAAAGGGGT

CCAGTGTCAGTCGTTGGAGGAGTCCGGGGGAGACCTGGTCAAGCCTGGG

GCATCCCTGACACTCACCTGCACAGCCTCTGGATTCTCCTTCACGAGCAA

CTACTACATGTGCTGGGTCCGCCAGGCTCCAGGGAAGGGGCTGGAGTGG

GTCGCGTGCATTTTTCTTGGTAGTAGTGGTAACACTGTCTACGCGAACTG

GGCGAAAGGCCGATTCACCATCTCCAAAACCTCGTCGACCACGGTGACT

CTGCAAATGACCAGTCTGACAGTCGCGGACACGGCCACCTATTTCTGTGC

GAGAGACTATGTTAATGGTTATGACTACTTTAACTTGTGGGGCCCAGGCA

CCTTGGTCACCGTCTCCTCA

Clone 15 VH AA (CDRs underlined)
(SEQ ID NO: 39)
METGLRWLLLVAVLKGVQCQSLEESGGDLVKPGASLTLTCTAS<u>GFSFTSNY</u>

YMCWVRQAPGKGLEWVACI<u>FLGSSG</u>NTVYANWAKGRFTISKTSSTTVTLQ

MTSLTVADTATYFCAR<u>DYVNGYDYFNL</u>WGPGTLVTVSS

Clone 15 HC AA (CDRs underlined)
(SEQ ID NO: 40)
METGLRWLLLVAVLKGVQCQSLEESGGDLVKPGASLTLTCTAS<u>GFSFTSNY</u>

YMCWVRQAPGKGLEWVACI<u>FLGSSG</u>NTVYANWAKGRFTISKTSSTTVTLQ

MTSLTVADTATYFCAR<u>DYVNGYDYFNL</u>WGPGTLVTVSSGQPKAPSVFPLAP

CCGDTPSSTVTLGCLVKGYLPEPVTVTWNSGTLTNGVRTFPSVRQSSGLYSL

SSVVSVTSSSQPVTCNVAHPATNTKVDKTVAPSTCSKPTCPPPELLGGPSVFI

FPPKPKDTLMISRTPEVTCVVVDVSQDDPEVQFTWYINNEQVRTARPPLREQ

QFNSTIRVVSTLPIAHQDWLRGKEFKCKVHNKALPAPIEKTISKARGQPLEPK

VYTMGPPREELSSRSVSLTCMINGFYPSDISVEWEKNGKAEDNYKTTPAVLD

SDGSYFLYSKLSVPTSEWQRGDVFTCSVMHEALHNHYTQKSISRSPGK

Clone 15 VH CDR1 AA
(SEQ ID NO: 41)
GFSFTSNY

Clone 15 VH CDR2 AA
(SEQ ID NO: 42)
FLGSSG

Clone 15 VH CDR3 AA
(SEQ ID NO: 43)
DYVNGYDYFNL

Clone 15 VL DNA
(SEQ ID NO: 44)
ATGGACACGAGGGCCCCCACTCAGCTGCTGGGGCTCCTGCTGCTCTGGCT

CCCAGGTGCCACATTTGCCCAAGTGCTGACCCAGACTGCATCCCCCGTGT

CTGCGGCTGTTGGAGGCACAGTCACCATCAATTGCCAGTCCAGTCAGAG

TGTTTATAATAAGAACTTAGCCTGGTATCAGCAGAAACCAGGGCAGCCT

CCCAAAGGCCTGATCTATTCTACATCGACTCTAGATTCTGGGGTCCCATC

GCGGTTCAGCGGCAGTGGATCTGGGACACAGTTCACTCTCACCATCAGC

GACGTGCAGTGTGACGATGCTGCCACTTACTACTGTCTAGGCAGTTATGA

TTGTAGTAGTGCTGATTGTAATGCTTTCGGCGGAGGGACCGAGGTGGTG

-continued

GTCAAA

Clone 15 VL AA (CDRs underlined)
(SEQ ID NO: 45)
MDTRAPTQLLGLLLLWLPGATFAQVLTQTASPVSAAVGGTVTINC<u>QSSQSV</u>

<u>YNKNLA</u>WYQQKPGQPPKGLIY<u>STSTLDS</u>GVPSRFSGSGSGTQFTLTISDVQC

DDAATYYC<u>LGSYDCSSADCNA</u>FGGGTEVVVK

Clone 15 LC AA (CDRs underlined)
(SEQ ID NO: 46)
MDTRAPTQLLGLLLLWLPGATFAQVLTQTASPVSAAVGGTVTINC<u>QSSQSV</u>

<u>YNKNLA</u>WYQQKPGQPPKGLIY<u>STSTLDS</u>GVPSRFSGSGSGTQFTLTISDVQC

DDAATYYC<u>LGSYDCSSADCNA</u>FGGGTEVVVKGDPVAPTVLIFPPAADQVAT

GTVTIVCVANKYFPDVTVTWEVDGTTQTTGIENSKTPQNSADCTYNLSSTLT

LTSTQYNSHKEYTCKVTQGTTSVVQSFNRGDC

Clone 15 VL CDR1 AA
(SEQ ID NO: 47)
QSSQSVYNKNLA

Clone 15 VL CDR2 AA
(SEQ ID NO: 48)
STSTLDS

Clone 15 VL CDR3 AA
(SEQ ID NO: 49)
LGSYDCSSADCNA

Clone 17 VH DNA
(SEQ ID NO: 50)
ATGGAGACTGGGCTGCGCTGGCTTCTCCTGGTCGCTGTGCTCAAAGGTGT

CCAATGTCAGTCGCTGGAGGAGTCCGGGGGAGGCCTGGTCAAGCCTGGG

GCATCCCTGACACTCACCTGCACAGCCTCTGGATTCTCCTTCAGTGACAG

TTGGTACTTGTGTTGGGTCCGCCAGGCTCCAGGGAAGGGGCTGGAGTGG

ATCGCATGCATTTATACTGGTGATGGTGACACTTATTACGCGACCTGGGC

GAAAGGCCGATTCACCATCTCCAAGACCTCGTCGACCACAGTGACTCTA

CAAATGACCAGTCTGACAGCCGCGGACACGGCCACCTATTTCTGTGCGA

GGGGTGCCCAATTTTACTTGTGGGGCCAAGGCACCCTGGTCACCGTCTCC

TCA

Clone 17 VH AA (CDRs underlined)
(SEQ ID NO: 51)
METGLRWLLLVAVLKGVQCQSLEESGGGLVKPGASLTLTCTAS<u>GFSFSDSW</u>

YLCWVRQAPGKGLEWIACI<u>YTGDG</u>DTYYATWAKGRFTISKTSSTTVTLQMT

SLTAADTATYFCAR<u>GAQFYL</u>WGQGTLVTVSS

Clone 17 HC AA (CDRs underlined)
(SEQ ID NO: 52)
METGLRWLLLVAVLKGVQCQSLEESGGGLVKPGASLTLTCTAS<u>GFSFSDSW</u>

YLCWVRQAPGKGLEWIACI<u>YTGDG</u>DTYYATWAKGRFTISKTSSTTVTLQMT

SLTAADTATYFCAR<u>GAQFYL</u>WGQGTLVTVSSGQPKAPSVFPLAPCCGDTPS

STVTLGCLVKGYLPEPVTVTWNSGTLTNGVRTFPSVRQSSGLYSLSSVVSVT

SSSQPVTCNVAHPATNTKVDKTVAPSTCSKPTCPPPELLGGPSVFIFPPKPKD

TLMISRTPEVTCVVVDVSQDDPEVQFTWYINNEQVRTARPPLREQQFNSTIR

VVSTLPIAHQDWLRGKEFKCKVHNKALPAPIEKTISKARGQPLEPKVYTMGP

PREELSSRSVSLTCMINGFYPSDISVEWEKNGKAEDNYKTTPAVLDSDGSYF

```
-continued
LYSKLSVPTSEWQRGDVFTCSVMHEALHNHYTQKSISRSPGK

Clone 17 VH CDR1 AA
                                                  (SEQ ID NO: 53)
GFSFSDSW Clone 17 VH CDR2 AA
                                                  (SEQ ID NO: 54)
YTGDG Clone 17 VH CDR3 AA
                                                  (SEQ ID NO: 55)
GAQFYL Clone 17 VL DNA
                                                  (SEQ ID NO: 56)
ATGGACACGAGGGCCCCCACTCAGCTGCTGGGGCTCCTGCTGCTCTGGCT

CCCAGGTGCCACATTTGCCCAGGTGCTGACCCAGACTCCATCCTCCGTGT

CTGCAGCTGTGGGAGGCACAGTCACCATCAATTGCCAGTCCAGTCAGAG

TGTTTATGCCAACACCTACTTATCCTGGTATCAGCAGAAACCAGGGCAGC

CTCCCAAGCAACTGATCTATTCTGCATCCAGTCTGGCATCTGGGGTCCCA

CCGCGGTTCAAAGGCAGTGGATCTGGGACACAGTTCGCTCTCACCATCA

GCGACGTGCAGTGTGACGATGCTGCCACTTACTACTGTCTAGGCAGATAT

AGTTGTGGTCTTGCTGATTGTGCTGCTTTCGGCGGAGGGACCGAGGTGGT

GGTCAAA

Clone 17 VL AA (CDRs underlined)
                                                  (SEQ ID NO: 57)
MDTRAPTQLLGLLLLWLPGATFAQVLTQTPSSVSAAVGGTVTINCQSSQSV

YANTYLSWYQQKPGQPPKQLIYSASSLASGVPPRFKGSGSGTQFALTISDVQ

CDDAATYYCLGRYSCGLADCAAFGGGTEVVVK

Clone 17 LC AA (CDRs underlined)
                                                  (SEQ ID NO: 58)
MDTRAPTQLLGLLLLWLPGATFAQVLTQTPSSVSAAVGGTVTINCQSSQSV

YANTYLSWYQQKPGQPPKQLIYSASSLASGVPPRFKGSGSGTQFALTISDVQ

CDDAATYYCLGRYSCGLADCAAFGGGTEVVVKGDPVAPTVLIFPPAADQV

ATGTVTIVCVANKYFPDVTVTWEVDGTTQTTGIENSKTPQNSADCTYNLSS

TLTLTSTQYNSHKEYTCKVTQGTTSVVQSFNRGDC

Clone 17 VL CDR1 AA
                                                  (SEQ ID NO: 59)
QSSQSVYANTYLS Clone 17 VL CDR2 AA
                                                  (SEQ ID NO: 60)
SASSLAS Clone 17 VL CDR3 AA
                                                  (SEQ ID NO: 61)
LGRYSCGLADCAA
```

In some embodiments, the antigen binding molecules of the present disclosure are antibodies and antigen binding fragments thereof. In some embodiments, the antibodies of the present disclosure comprise at least one CDR set forth in FIGS. 5-21. In another aspect, the present disclosure provides hybridomas capable of producing the antibodies disclosed herein, and also methods of producing antibodies from hybridomas, as described herein and as known in the art.

Humanized antibodies are described herein and may be prepared by known techniques. In some embodiments, a humanized monoclonal antibody comprises the variable domain of a murine or rabbit antibody (or all or part of the antigen binding site thereof) and a constant domain derived from a human antibody. Alternatively, a humanized antibody fragment may comprise an antigen binding site of a murine or rabbit monoclonal antibody and a variable domain fragment (lacking the antigen binding site) derived from a human antibody. Procedures for the production of engineered monoclonal antibodies include those described in Riechmann et al., (1988) *Nature* 332:323, Liu et al., (1987) *Proc. Nat. Acad. Sci. USA* 84:3439, Larrick et al., (1989) *Bio/Technology* 7:934, and Winter et al., (1993) *TIPS* 14:139. In some embodiments, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) *FASEB J.* 9:133-39; Tamura et al., (2000) *J. Immunol.* 164:1432-41; Zhang et al., (2005) *Mol. Immunol.* 42(12): 1445-1451; Hwang et al., *Methods*. (2005) 36(1):35-42; Dall' Acqua et al., (2005) *Methods* 36(1):43-60; and Clark, (2000) *Immunology Today* 21(8):397-402.

An antigen binding molecule of the present invention can also be a fully human monoclonal antibody. Fully human monoclonal antibodies can be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., (1997) *Curr. Opin. Biotechnol.* 8:455-58).

Examples of techniques for production and use of transgenic animals for the production of human or partially human antibodies are described in U.S. Pat. Nos. 5,814,318, 5,569,825, and 5,545,806; Davis et al., *Antibody Engineering: Methods and Protocols*, (Lo, ed) Humana Press, NJ, 191-200 (2003); Kellermann et al., (2002) *Curr Opin Biotechnol.* 13:593-97; Russel et al., (2000) *Infect Immun.* 68:1820-26; Gallo et al., (2000) *Eur J. Immun.* 30:534-40; Davis et al., (1999) *Cancer Metastasis Rev.* 18:421-25; Green, (1999) *J Immunol Methods* 231:11-23; Jakobovits, (1998) *Advanced Drug Delivery Reviews* 31:33-42; Green et al., (1998) *J Exp Med.* 188:483-95; Jakobovits, (1998) *Exp. Opin. Invest. Drugs.* 7:607-14; Tsuda et al., (1997) *Genomics*, 42:413-21; Mendez et al., (1997) *Nat. Genet.* 15:146-56; Jakobovits, (1994) *Curr Biol.* 4:761-63; Arbones et al., (1994) *Immunity* 1:247-60; Green et al., (1994) *Nat. Genet.* 7:13-21; Jakobovits et al., (1993) *Nature* 362:255-58; Jakobovits et al., (1993) *Proc Natl Acad Sci USA* 90:2551-55; Chen et al., (1993) *Intl Immunol* 5:647-656; Choi et al., (1993) *Nature Genetics* 4:117-23; Fishwild et al., (1996) *Nature Biotechnology* 14:845-51; Lonberg et al., (1994) *Nature* 368: 856-59; Lonberg, (1994) *Handbook of Experimental Pharmacology* 113: 49-101; Neuberger, (1996) *Nature Biotech* 14:826; Taylor et al., (1992) *Nucleic Acids Research* 20:6287-95; Taylor et al., (1994) *Intl Immunol* 6:579-91; Tomizuka et al., (1997) *Nature Genetics* 16:133-43; Tomizuka et al., (2000) *Proc Nat Acad Sci USA* 97:722-27; Tuaillon et al., (1993) *Proc Nat Acad Sci USA* 90:3720-24; Tuaillon et al., (1994) *J Immunol* 152:2912-20; Lonberg et al., (1994) *Nature* 368:856; Taylor et al., (1994) *Intl Immunol* 6:579; U.S. Pat. No. 5,877,397; Bruggemann et al., (1997) *Curr. Opin. Biotechnol.* 8:455-58; Jakobovits et al., (1995) *Ann. N.Y. Acad. Sci.* 764:525-35.

An additional method for obtaining antigen binding molecules of the invention is by the use of phage display, which is well-established for this purpose. See, e.g., Winter et al., (1994) *Ann. Rev. Immunol.* 12:433-55; Burton et al., (1994) *Adv. Immunol* 57:191-280. Human or murine immunoglobulin variable region gene combinatorial libraries can be created in phage vectors that can be screened to select Ig fragments (Fab, Fv, sFv, or multimers thereof) that bind the anti-CD19 scFv FMC63, as well as molecules comprising this sequence and cells presenting such molecules. See, e.g., U.S. Pat. No. 5,223,409; Huse et al., (1989) *Science* 246: 1275-81; Sastry et al., (1989) *Proc. Natl. Acad. Sci. USA* 86:5728-32; Alting-Mees et al., (1990) *Strategies in Molecular Biology* 3:1-9; Kang et al., (1991) *Proc. Natl. Acad. Sci. USA* 88:4363-66; Hoogenboom et al., (1992) *J Mol. Biol.* 227:381-388; Schlebusch et al., (1997) *Hybridoma* 16:47-52 and references cited therein. For example, a library containing a plurality of polynucleotide sequences encoding Ig variable region fragments can be inserted into the genome of a filamentous bacteriophage, such as M13 or lambda phage (λImmunoZap™(H) and λImmunoZap™(L) vectors (Stratagene, La Jolla, Calif.) can also be used in this approach) or a variant thereof, in frame with the sequence encoding a phage coat protein.

Briefly, mRNA is isolated from a B-cell population, and used to create heavy and light chain immunoglobulin cDNA expression libraries in the λImmunoZap™(H) and λImmunoZap™(L) vectors. These vectors can be screened individually or co-expressed to form Fab fragments or antibodies. Positive plaques can subsequently be converted to a non-lytic plasmid that allows high level expression of monoclonal antibody fragments from *E. coli*.

In some embodiments, in a hybridoma the variable regions of a gene expressing a monoclonal antibody of interest are amplified using nucleotide primers. These primers can be synthesized by one of ordinary skill in the art, or can be purchased from commercial sources, which also sell primers for mouse and human variable regions including, among others, primers for $V_{Ha}$, $V_{Hb}$, $V_{Hc}$, $V_{Hd}$, $C_{H1}$, $V_L$ and $C_L$ regions). These primers can be used to amplify heavy or light chain variable regions, which can then be inserted into vectors such as λImmunoZap™(H) and λImmunoZap™(L) (Stratagene), respectively. These vectors can then be introduced into *E. coli*, yeast, or mammalian-based systems for expression. Large amounts of a single-chain protein containing a fusion of the $V_H$ and $V_L$ domains can be produced using these methods.

Once cells producing the antigen binding molecules provided herein have been obtained using any of the above-described immunization and other techniques, the specific antibody genes can be cloned by isolating and amplifying DNA or mRNA therefrom according to standard procedures as described herein. The antibodies produced therefrom can be sequenced and the CDRs identified and the DNA coding for the CDRs can be manipulated as described previously to generate other antibodies according to the invention.

It will be understood by one skilled in the art that some proteins, such as antibodies, can undergo a variety of post-translational modifications. The type and extent of these modifications often depends on the host cell line used to express the protein as well as the culture conditions. Such modifications can include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, (1995) *J Chromatog* 705:129-34.

An alternative method for production of a murine monoclonal antibody (from which FMC63 can be derived) is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, e.g., Baines and Thorpe, (1992) in *Methods in Molecular Biology,* 10:79-104 (The Humana Press). Monoclonal antibodies can be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, and an anti-idiotype antibody.

Although the disclosed antigen binding molecules were produced in a rabbit system, human, partially human, or humanized antibodies may be suitable for many applications, particularly those involving administration of the antibody to a human subject, other types of antigen binding molecules will be suitable for certain applications. Such antibodies can be prepared as described herein and form an aspect of the instant disclosure.

The instant disclosure provides antigen binding molecules that specifically bind to the anti-CD19 scFv FMC63 (SEQ ID NO: 1), molecules comprising this sequence and cells presenting such molecules. Antigen binding molecules that cross compete with the disclosed antigen binding molecules disclosed herein for an aspect of the disclosure. In certain embodiments, the antigen binding molecule cross competes with a reference antibody comprising an amino acid sequence selected from the group consisting of SEQ ID NOs: 1-60. In certain embodiments, the antigen binding molecule cross competes with a reference antibody, wherein the reference antibody comprises a VH CDR1 comprising an amino acid sequence of SEQ ID NOs: 5, 23, 41 and 53. In certain embodiments, the antigen binding molecule cross competes with a reference antibody, wherein the reference antibody comprises a VH CDR2 comprising an amino acid sequence of SEQ ID NOs: 6, 24, 42 and 54. In certain embodiments, the antigen binding molecule cross competes with a reference antibody, wherein the reference antibody comprises a VH CDR3 comprising an amino acid sequence of SEQ ID NOs: 7, 25, 43 and 55. In certain embodiments, the antigen binding molecule cross competes with a reference antibody, wherein the reference antibody comprises a VL CDR1 comprising an amino acid sequence of SEQ ID NOs: 11, 29, 47 and 59. In certain embodiments, the antigen binding molecule cross competes with a reference antibody, wherein the reference antibody comprises a VL CDR2 comprising an amino acid sequence of SEQ ID NOs: 12, 30, 48 and 60. In certain embodiments, the antigen binding molecule cross competes with a reference antibody, wherein the reference antibody comprises a VL CDR3 comprising an amino acid sequence of SEQ ID NOs: 13, 31, 49 and 61.

In some embodiments, the polynucleotides of the present invention encodes an antibody or antigen binding molecule that specifically binds the anti-CD19 scFv FMC63 (SEQ ID NO: 1), as well as molecules comprising these sequences and cells presenting such molecules, wherein the antibody or antigen binding molecule binds the same or an overlapping epitope as a reference antibody disclosed herein (e.g., those comprising sequences presented in FIGS. 5-21). In certain embodiments, the antibody or antigen binding molecule binds the same or an overlapping epitope as a reference antibody.

II.A. Clone 7

In some embodiments, an antigen binding molecule or antibody that specifically binds to the anti-CD19 scFv FMC63 (SEQ ID NO: 1), molecules comprising this sequence and cells presenting such molecules, comprises a VH CDR1 comprising, consisting of, or consisting essentially of the amino acid sequence GFSFNN (SEQ ID NO: 5).

In some embodiments, an antigen binding molecule or antibody that specifically binds to the anti-CD19 scFv FMC63 (SEQ ID NO: 1), molecules comprising this sequence and cells presenting such molecules, comprises a VH CDR2 comprising, consisting of, or consisting essentially of the amino acid sequence YVGSSD (SEQ ID NO: 6).

In some embodiments, an antigen binding molecule or antibody that specifically binds to the anti-CD19 scFv FMC63 (SEQ ID NO: 1), molecules comprising this sequence and cells presenting such molecules, comprises a VH CDR3 comprising, consisting of, or consisting essentially of the amino acid sequence NLGL (SEQ ID NO: 7).

In some embodiments, an antigen binding molecule or antibody that specifically binds to the anti-CD19 scFv FMC63 (SEQ ID NO: 1), molecules comprising this sequence and cells presenting such molecules, comprises a heavy chain VH comprising: (a) a VH CDR1 comprising, consisting of, or consisting essentially of the amino acid sequence GFSFNN (SEQ ID NO: 5); and/or (b) a VH CDR2 comprising, consisting of, or consisting essentially of the amino acid sequence YVGSSD (SEQ ID NO: 6); and/or (c) a VH CDR3 comprising, consisting of, or consisting essentially of the amino acid sequence NLGL (SEQ ID NO: 7).

In some embodiments, the antigen binding molecule or antibody that specifically binds to the anti-CD19 scFv FMC63 (SEQ ID NO: 1), molecules comprising this sequence and cells presenting this sequence, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 5, 19, 20 and 21. In a particular embodiment, the VH CDRs are those presented in FIG. 5.

In some embodiments, the antigen binding molecule or antibody that specifically binds to the anti-CD19 scFv FMC63 (SEQ ID NO: 1), molecules comprising this sequence and cells presenting this sequence, comprises a heavy chain variable region sequence comprising an amino acid sequence of FIG. 5 (SEQ ID NO: 3).

In some embodiments, the antigen binding molecule or antibody that specifically binds to the anti-CD19 scFv FMC63 (SEQ ID NO: 1), molecules comprising this sequence and cells presenting this sequence, comprises the VH framework regions (FRs) described herein. In specific embodiments, the antibody or antigen binding molecule comprises the VH FRs as set forth in, or derivable from, the sequences presented in FIG. 5 (e.g., one, two, three, or four of the FRs in one sequence of FIG. 5).

In some embodiments, the antigen binding molecule or antibody that specifically binds to the anti-CD19 scFv FMC63 (SEQ ID NO: 1), molecules comprising this sequence and cells presenting this sequence, comprises a heavy chain sequence disclosed herein (e.g., SEQ ID NO: 4 in FIG. 5). In some embodiments, the antibody or antigen binding molecule comprises a heavy chain variable region comprising the amino acid sequence of SEQ ID NO: 3.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:3.

In some embodiments, an antigen binding molecule or antibody that specifically binds to the anti-CD19 scFv FMC63 (SEQ ID NO: 1), molecules comprising this sequence and cells presenting such molecules, comprises a VL CDR1 comprising, consisting of, or consisting essentially of the amino acid sequence QASESVYNSDWLA (SEQ ID NO: 11).

In some embodiments, an antigen binding molecule or antibody that specifically binds to the anti-CD19 scFv FMC63 (SEQ ID NO: 1), molecules comprising this sequence and cells presenting such molecules, comprises a VL CDR2 comprising, consisting of, or consisting essentially of the amino acid sequence AASTLAS (SEQ ID NO: 12).

In some embodiments, an antigen binding molecule or antibody that specifically binds to the anti-CD19 scFv FMC63 (SEQ ID NO: 1), molecules comprising this sequence and cells presenting such molecules, comprises a VL CDR3 comprising, consisting of, or consisting essentially of the amino acid sequence AGYKSSSTDGIA (SEQ ID NO: 13).

In some embodiments, an antigen binding molecule or antibody that specifically binds to the anti-CD19 scFv FMC63 (SEQ ID NO: 1), molecules comprising this sequence and cells presenting such molecules, comprises a light chain VL comprising: (a) a VL CDR1 comprising, consisting of, or consisting essentially of the amino acid sequence QASESVYNSDWLA (SEQ ID NO: 11); and/or (b) a VL CDR2 comprising, consisting of, or consisting essentially of the amino acid sequence AASTLAS (SEQ ID NO: 12); and/or (c) a VL CDR3 comprising, consisting of, or consisting essentially of the amino acid sequence AGYKSSSTDGIA (SEQ ID NO: 13).

In some embodiments, the antigen binding molecule or antibody that specifically binds to the anti-CD19 scFv FMC63 (SEQ ID NO: 1), molecules comprising this sequence and cells presenting this sequence, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 6, 19, 20 and 21. In a particular embodiment, the VL CDRs are those presented in FIG. 6.

In some embodiments, the antigen binding molecule or antibody that specifically binds to the anti-CD19 scFv FMC63 (SEQ ID NO: 1), molecules comprising this sequence and cells presenting this sequence, comprises a light chain variable region sequence comprising an amino acid sequence of FIG. 6 (SEQ ID NO: 9)

In some embodiments, the antigen binding molecule or antibody that specifically binds to the anti-CD19 scFv FMC63 (SEQ ID NO: 1), molecules comprising this sequence and cells presenting this sequence, comprises the VL framework regions (FRs) described herein. In specific embodiments, the antibody or antigen binding molecule comprises the VL FRs as set forth in, or derivable from, the sequences presented in FIG. 6 (e.g., one, two, three, or four of the FRs in one sequence of FIG. 6).

In some embodiments, the antigen binding molecule or antibody that specifically binds to the anti-CD19 scFv FMC63 (SEQ ID NO: 1), molecules comprising this sequence and cells presenting this sequence, comprises a light chain sequence disclosed herein (e.g., SEQ ID NO: 10 in FIG. 6). In some embodiments, the antibody or antigen binding molecule comprises a light chain variable region comprising the amino acid sequence of SEQ ID NO: 9.

In various embodiments, the light chain variable region is 80%, 85%, 90%, 91%, 92%, 93%, 94%, 95%, 96%, 97%, 98% or 99% identical to the light chain variable region sequence of SEQ ID NO: 9.

In some embodiments, the antibody or antigen binding molecule that specifically binds to the anti-CD19 scFv FMC63 (SEQ ID NO: 1), molecules comprising this sequence and cells presenting this sequence, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region comprising the amino acid sequence of SEQ ID NO: 5; (b) a VH CDR2 region comprising the amino acid sequence of SEQ ID NO: 6; (c) a VH CDR3 region comprising the amino acid sequence of SEQ ID NO: 7; (d) a VL CDR1 region comprising the amino acid sequence of SEQ ID NO: 11; (e) a VL CDR2 region comprising the amino acid sequence of SEQ ID NO: 12; and (f) a VL CDR3 region comprising the amino acid sequence of SEQ ID NO: 13.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 5, 6, respectively, and in FIGS. 19, 20 and 21.

In some embodiments, the antibody or antigen binding molecule that specifically binds to the anti-CD19 scFv FMC63 (SEQ ID NO: 1), molecules comprising this sequence and cells presenting this sequence, comprises a heavy chain variable region sequence disclosed herein (e.g., in FIG. 5) and a light chain variable region sequence disclosed herein (e.g., in FIG. 6).

In some embodiments, the antibody or antigen binding molecule comprises: (a) a heavy chain variable region comprising the amino acid sequence of SEQ ID NO: 3; and (b) a light chain variable region comprising the amino acid sequence of SEQ ID NO: 9. Nucleotide sequences encoding the heavy chain variable region and the light chain variable region are provided in FIGS. 5 and 6, respectively.

In some embodiments, the antibody or antigen binding molecule that specifically binds to the anti-CD19 scFv FMC63 (SEQ ID NO: 1), molecules comprising this sequence and cells presenting this sequence, comprises a heavy chain sequence disclosed herein (e.g., in FIG. 5) and a light chain sequence disclosed herein (e.g., in FIG. 6).

In some embodiments, the antibody or antigen binding molecule comprises: (a) a heavy chain comprising the amino acid sequence of SEQ ID NO: 4; and (b) a light chain comprising the amino acid sequence of SEQ ID NO: 10.

In some embodiments, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 4; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 10.

II.B. Clone 13

In some embodiments, an antigen binding molecule or antibody that specifically binds to the anti-CD19 scFv FMC63 (SEQ ID NO: 1), molecules comprising this sequence and cells presenting such molecules, comprises a VH CDR1 comprising, consisting of, or consisting essentially of the amino acid sequence GFSFNN (SEQ ID NO: 5).

In some embodiments, an antigen binding molecule or antibody that specifically binds to the anti-CD19 scFv FMC63 (SEQ ID NO: 1), molecules comprising this sequence and cells presenting such molecules, comprises a VH CDR2 comprising, consisting of, or consisting essentially of the amino acid sequence YVGSSD (SEQ ID NO: 6).

In some embodiments, an antigen binding molecule or antibody that specifically binds to the anti-CD19 scFv FMC63 (SEQ ID NO: 1), molecules comprising this sequence and cells presenting such molecules, comprises a VH CDR3 comprising, consisting of, or consisting essentially of the amino acid sequence NLGL (SEQ ID NO: 7).

In some embodiments, an antigen binding molecule or antibody that specifically binds to the anti-CD19 scFv FMC63 (SEQ ID NO: 1), molecules comprising this sequence and cells presenting such molecules, comprises a heavy chain VH comprising: (a) a VH CDR1 comprising, consisting of, or consisting essentially of the amino acid sequence GFSFNN (SEQ ID NO: 5); and/or (b) a VH CDR2 comprising, consisting of, or consisting essentially of the amino acid sequence YVGSSD (SEQ ID NO: 6); and/or (c) a VH CDR3 comprising, consisting of, or consisting essentially of the amino acid sequence NLGL (SEQ ID NO: 7).

In some embodiments, the antigen binding molecule or antibody that specifically binds to the anti-CD19 scFv FMC63 (SEQ ID NO: 1), molecules comprising this sequence and cells presenting this sequence, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 7, 19, 20 and 21. In a particular embodiment, the VH CDRs are those presented in FIG. 7.

In some embodiments, the antigen binding molecule or antibody that specifically binds to the anti-CD19 scFv FMC63 (SEQ ID NO: 1), molecules comprising this sequence and cells presenting this sequence, comprises a heavy chain variable region sequence comprising an amino acid sequence of FIG. 7 (SEQ ID NO: 15).

In some embodiments, the antigen binding molecule or antibody that specifically binds to the anti-CD19 scFv FMC63 (SEQ ID NO: 1), molecules comprising this sequence and cells presenting this sequence, comprises the VH framework regions (FRs) described herein. In specific embodiments, the antibody or antigen binding molecule comprises the VH FRs as set forth in, or derivable from, the sequences presented in FIG. 7 (e.g., one, two, three, or four of the FRs in one sequence of FIG. 7).

In some embodiments, the antigen binding molecule or antibody that specifically binds to the anti-CD19 scFv FMC63 (SEQ ID NO: 1), molecules comprising this sequence and cells presenting this sequence, comprises a heavy chain sequence disclosed herein (e.g., SEQ ID NO: 16 in FIG. 7). In some embodiments, the antibody or antigen binding molecule comprises a heavy chain variable region comprising the amino acid sequence of SEQ ID NO: 15.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO: 15.

In some embodiments, an antigen binding molecule or antibody that specifically binds to the anti-CD19 scFv FMC63 (SEQ ID NO: 1), molecules comprising this sequence and cells presenting such molecules, comprises a VL CDR1 comprising, consisting of, or consisting essentially of the amino acid sequence QASESVYNSDWLA (SEQ ID NO: 11).

In some embodiments, an antigen binding molecule or antibody that specifically binds to the anti-CD19 scFv FMC63 (SEQ ID NO: 1), molecules comprising this sequence and cells presenting such molecules, comprises a VL CDR2 comprising, consisting of, or consisting essentially of the amino acid sequence AASTLAS (SEQ ID NO: 12).

In some embodiments, an antigen binding molecule or antibody that specifically binds to the anti-CD19 scFv FMC63 (SEQ ID NO: 1), molecules comprising this sequence and cells presenting such molecules, comprises a VL CDR3 comprising, consisting of, or consisting essentially of the amino acid sequence AGYKSSSTDGIA (SEQ ID NO: 13).

In some embodiments, an antigen binding molecule or antibody that specifically binds to the anti-CD19 scFv FMC63 (SEQ ID NO: 1), molecules comprising this sequence and cells presenting such molecules, comprises a light chain VL comprising: (a) a VL CDR1 comprising, consisting of, or consisting essentially of the amino acid sequence QASESVYNSDWLA (SEQ ID NO: 11); and/or (b) a VL CDR2 comprising, consisting of, or consisting essentially of the amino acid sequence AASTLAS (SEQ ID NO: 12); and/or (c) a VL CDR3 comprising, consisting of, or consisting essentially of the amino acid sequence AGYKSSSTDGIA (SEQ ID NO: 13).

In some embodiments, the antigen binding molecule or antibody that specifically binds to the anti-CD19 scFv FMC63 (SEQ ID NO: 1), molecules comprising this sequence and cells presenting this sequence, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 8, 19, 20 and 21. In a particular embodiment, the VL CDRs are those presented in FIG. 8.

In some embodiments, the antigen binding molecule or antibody that specifically binds to the anti-CD19 scFv FMC63 (SEQ ID NO: 1), molecules comprising this sequence and cells presenting this sequence, comprises a light chain variable region sequence comprising an amino acid sequence of FIG. 8 (SEQ ID NO: 18)

In some embodiments, the antigen binding molecule or antibody that specifically binds to the anti-CD19 scFv FMC63 (SEQ ID NO: 1), molecules comprising this sequence and cells presenting this sequence, comprises the VL framework regions (FRs) described herein. In specific embodiments, the antibody or antigen binding molecule comprises the VL FRs as set forth in, or derivable from, the sequences presented in FIG. 8 (e.g., one, two, three, or four of the FRs in one sequence of FIG. 8).

In some embodiments, the antigen binding molecule or antibody that specifically binds to the anti-CD19 scFv FMC63 (SEQ ID NO: 1), molecules comprising this sequence and cells presenting this sequence, comprises a light chain sequence disclosed herein (e.g., SEQ ID NO: 19 in FIG. 8). In some embodiments, the antibody or antigen binding molecule comprises a light chain variable region comprising the amino acid sequence of SEQ ID NO: 18.

In various embodiments, the light chain variable region is 80%, 85%, 90%, 91%, 92%, 93%, 94%, 95%, 96%, 97%, 98% or 99% identical to the light chain variable region sequence of SEQ ID NO: 18.

In some embodiments, the antibody or antigen binding molecule that specifically binds to the anti-CD19 scFv FMC63 (SEQ ID NO: 1), molecules comprising this sequence and cells presenting this sequence, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region comprising the amino acid sequence of SEQ ID NO: 5; (b) a VH CDR2 region comprising the amino acid sequence of SEQ ID NO: 6; (c) a VH CDR3 region comprising the amino acid sequence of SEQ ID NO: 7; (d) a VL CDR1 region comprising the amino acid sequence of SEQ ID NO: 11; (e) a VL CDR2 region comprising the amino acid sequence of SEQ ID NO: 12; and (f) a VL CDR3 region comprising the amino acid sequence of SEQ ID NO: 13.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 7, 8, respectively, and in FIGS. 19, 20 and 21.

In some embodiments, the antibody or antigen binding molecule that specifically binds to the anti-CD19 scFv FMC63 (SEQ ID NO: 1), molecules comprising this sequence and cells presenting this sequence, comprises a heavy chain variable region sequence disclosed herein (e.g., in FIG. 7) and a light chain variable region sequence disclosed herein (e.g., in FIG. 8).

In some embodiments, the antibody or antigen binding molecule comprises: (a) a heavy chain variable region comprising the amino acid sequence of SEQ ID NO: 15; and (b) a light chain variable region comprising the amino acid sequence of SEQ ID NO: 18. Nucleotide sequences encoding the heavy chain variable region and the light chain variable region are provided in FIGS. 7 and 8, respectively.

In some embodiments, the antibody or antigen binding molecule that specifically binds to the anti-CD19 scFv FMC63 (SEQ ID NO: 1), molecules comprising this sequence and cells presenting this sequence, comprises a heavy chain sequence disclosed herein (e.g., in FIG. 7) and a light chain sequence disclosed herein (e.g., in FIG. 8).

In some embodiments, the antibody or antigen binding molecule comprises: (a) a heavy chain comprising the amino acid sequence of SEQ ID NO: 16; and (b) a light chain comprising the amino acid sequence of SEQ ID NO: 19.

In some embodiments, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 16; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 19.

II.C. Clone 14-1

In some embodiments, an antigen binding molecule or antibody that specifically binds to the anti-CD19 scFv FMC63 (SEQ ID NO: 1), molecules comprising this sequence and cells presenting such molecules, comprises a VH CDR1 comprising, consisting of, or consisting essentially of the amino acid sequence GFDFSINY (SEQ ID NO: 23).

In some embodiments, an antigen binding molecule or antibody that specifically binds to the anti-CD19 scFv FMC63 (SEQ ID NO: 1), molecules comprising this sequence and cells presenting such molecules, comprises a VH CDR2 comprising, consisting of, or consisting essentially of the amino acid sequence YTGDD (SEQ ID NO: 24).

In some embodiments, an antigen binding molecule or antibody that specifically binds to the anti-CD19 scFv FMC63 (SEQ ID NO: 1), molecules comprising this sequence and cells presenting such molecules, comprises a VH CDR3 comprising, consisting of, or consisting essentially of the amino acid sequence GLYSGSINNL (SEQ ID NO: 25).

In some embodiments, an antigen binding molecule or antibody that specifically binds to the anti-CD19 scFv FMC63 (SEQ ID NO: 1), molecules comprising this sequence and cells presenting such molecules, comprises a heavy chain VH comprising: (a) a VH CDR1 comprising, consisting of, or consisting essentially of the amino acid sequence GFDFSINY (SEQ ID NO: 23); and/or (b) a VH CDR2 comprising, consisting of, or consisting essentially of the amino acid sequence YTGDD (SEQ ID NO: 24); and/or (c) a VH CDR3 comprising, consisting of, or consisting essentially of the amino acid sequence GLYSGSINNL (SEQ ID NO: 25).

In some embodiments, the antigen binding molecule or antibody that specifically binds to the anti-CD19 scFv FMC63 (SEQ ID NO: 1), molecules comprising this sequence and cells presenting this sequence, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 19, 20, and 21. In a particular embodiment, the VH CDRs are those presented in FIG. 9.

In some embodiments, the antigen binding molecule or antibody that specifically binds to the anti-CD19 scFv FMC63 (SEQ ID NO: 1), molecules comprising this sequence and cells presenting this sequence, comprises a heavy chain variable region sequence comprising an amino acid sequence of FIG. 9 (SEQ ID NO: 21).

In some embodiments, the antigen binding molecule or antibody that specifically binds to the anti-CD19 scFv FMC63 (SEQ ID NO: 1), molecules comprising this sequence and cells presenting this sequence, comprises the VH framework regions (FRs) described herein. In specific embodiments, the antibody or antigen binding molecule comprises the VH FRs as set forth in, or derivable from, the sequences presented in FIG. 9 (e.g., one, two, three, or four of the FRs in one sequence of FIG. 9).

In some embodiments, the antigen binding molecule or antibody that specifically binds to the anti-CD19 scFv FMC63 (SEQ ID NO: 1), molecules comprising this sequence and cells presenting this sequence, comprises a heavy chain sequence disclosed herein (e.g., SEQ ID NO: 22 in FIG. 9). In some embodiments, the antibody or antigen binding molecule comprises a heavy chain variable region comprising the amino acid sequence of SEQ ID NO: 21.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:21.

In some embodiments, an antigen binding molecule or antibody that specifically binds to the anti-CD19 scFv FMC63 (SEQ ID NO: 1), molecules comprising this sequence and cells presenting such molecules, comprises a VL CDR1 comprising, consisting of, or consisting essentially of the amino acid sequence QASQSVYNNDYLS (SEQ ID NO: 29).

In some embodiments, an antigen binding molecule or antibody that specifically binds to the anti-CD19 scFv FMC63 (SEQ ID NO: 1), molecules comprising this sequence and cells presenting such molecules, comprises a VL CDR2 comprising, consisting of, or consisting essentially of the amino acid sequence YASTLAS (SEQ ID NO: 30).

In some embodiments, an antigen binding molecule or antibody that specifically binds to the anti-CD19 scFv FMC63 (SEQ ID NO: 1), molecules comprising this sequence and cells presenting such molecules, comprises a VL CDR3 comprising, consisting of, or consisting essentially of the amino acid sequence AGVKGYSNDNNG (SEQ ID NO: 31).

In some embodiments, an antigen binding molecule or antibody that specifically binds to the anti-CD19 scFv FMC63 (SEQ ID NO: 1), molecules comprising this sequence and cells presenting such molecules, comprises a light chain VL comprising: (a) a VL CDR1 comprising, consisting of, or consisting essentially of the amino acid sequence QASQSVYNNDYLS (SEQ ID NO: 29); and/or (b) a VL CDR2 comprising, consisting of, or consisting essentially of the amino acid sequence YASTLAS (SEQ ID NO: 30); and/or (c) a VL CDR3 comprising, consisting of, or consisting essentially of the amino acid sequence AGVK-GYSNDNNG (SEQ ID NO: 31).

In some embodiments, the antigen binding molecule or antibody that specifically binds to the anti-CD19 scFv FMC63 (SEQ ID NO: 1), molecules comprising this sequence and cells presenting this sequence, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 19, 20 and 21. In a particular embodiment, the VL CDRs are those presented in FIG. 10.

In some embodiments, the antigen binding molecule or antibody that specifically binds to the anti-CD19 scFv FMC63 (SEQ ID NO: 1), molecules comprising this sequence and cells presenting this sequence, comprises a light chain variable region sequence comprising an amino acid sequence of FIG. 10 (SEQ ID NO: 27).

In some embodiments, the antigen binding molecule or antibody that specifically binds to the anti-CD19 scFv FMC63 (SEQ ID NO: 1), molecules comprising this sequence and cells presenting this sequence, comprises the VL framework regions (FRs) described herein. In specific embodiments, the antibody or antigen binding molecule comprises the VL FRs as set forth in, or derivable from, the sequences presented in FIG. 10 (e.g., one, two, three, or four of the FRs in one sequence of FIG. 10).

In some embodiments, the antigen binding molecule or antibody that specifically binds to the anti-CD19 scFv FMC63 (SEQ ID NO: 1), molecules comprising this sequence and cells presenting this sequence, comprises a light chain sequence disclosed herein (e.g., SEQ ID NO: 28 in FIG. 10). In some embodiments, the antibody or antigen binding molecule comprises a light chain variable region comprising the amino acid sequence of SEQ ID NO: 27.

In various embodiments, the light chain variable region is 80%, 85%, 90%, 91%, 92%, 93%, 94%, 95%, 96%, 97%, 98% or 99% identical to the light chain variable region sequence of SEQ ID NO: 27.

In some embodiments, the antibody or antigen binding molecule that specifically binds to the anti-CD19 scFv FMC63 (SEQ ID NO: 1), molecules comprising this sequence and cells presenting this sequence, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region comprising the amino acid sequence of SEQ ID NO: 23; (b) a VH CDR2 region comprising the amino acid sequence of SEQ ID NO: 24; (c) a VH CDR3 region comprising the amino acid sequence of SEQ ID NO: 25; (d) a VL CDR1 region comprising the amino acid sequence of SEQ ID NO: 29; (e) a VL CDR2 region comprising the amino acid sequence of SEQ ID NO: 30; and (f) a VL CDR3 region comprising the amino acid sequence of SEQ ID NO: 31.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 9, 10, respectively, and in FIGS. 19, 20 and 21.

In some embodiments, the antibody or antigen binding molecule that specifically binds to the anti-CD19 scFv FMC63 (SEQ ID NO: 1), molecules comprising this sequence and cells presenting this sequence, comprises a heavy chain variable region sequence disclosed herein (e.g., in FIG. 9) and a light chain variable region sequence disclosed herein (e.g., in FIG. 10).

In some embodiments, the antibody or antigen binding molecule comprises: (a) a heavy chain variable region comprising the amino acid sequence of SEQ ID NO: 22; and (b) a light chain variable region comprising the amino acid sequence of SEQ ID NO: 28. Nucleotide sequences encoding the heavy chain variable region and the light chain variable region are provided in FIGS. 9 and 10, respectively.

In some embodiments, the antibody or antigen binding molecule that specifically binds to the anti-CD19 scFv FMC63 (SEQ ID NO: 1), molecules comprising this sequence and cells presenting this sequence, comprises a heavy chain sequence disclosed herein (e.g., in FIG. 9) and a light chain sequence disclosed herein (e.g., in FIG. 10).

In some embodiments, the antibody or antigen binding molecule comprises: (a) a heavy chain comprising the amino acid sequence of SEQ ID NO: 22; and (b) a light chain comprising the amino acid sequence of SEQ ID NO: 28.

In some embodiments, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 22; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 28.

II.D. Clone 14-7

In some embodiments, an antigen binding molecule or antibody that specifically binds to the anti-CD19 scFv FMC63 (SEQ ID NO: 1), molecules comprising this sequence and cells presenting such molecules, comprises a VH CDR1 comprising, consisting of, or consisting essentially of the amino acid sequence GFDFSINY (SEQ ID NO: 23).

In some embodiments, an antigen binding molecule or antibody that specifically binds to the anti-CD19 scFv FMC63 (SEQ ID NO: 1), molecules comprising this sequence and cells presenting such molecules, comprises a VH CDR2 comprising, consisting of, or consisting essentially of the amino acid sequence YTGDD (SEQ ID NO: 24).

In some embodiments, an antigen binding molecule or antibody that specifically binds to the anti-CD19 scFv FMC63 (SEQ ID NO: 1), molecules comprising this sequence and cells presenting such molecules, comprises a VH CDR3 comprising, consisting of, or consisting essentially of the amino acid sequence GLYSGSINNL (SEQ ID NO: 25).

In some embodiments, an antigen binding molecule or antibody that specifically binds to the anti-CD19 scFv FMC63 (SEQ ID NO: 1), molecules comprising this sequence and cells presenting such molecules, comprises a heavy chain VH comprising: (a) a VH CDR1 comprising, consisting of, or consisting essentially of the amino acid sequence GFDFSINY (SEQ ID NO: 23); and/or (b) a VH CDR2 comprising, consisting of, or consisting essentially of the amino acid sequence YTGDD (SEQ ID NO: 24); and/or (c) a VH CDR3 comprising, consisting of, or consisting essentially of the amino acid sequence GLYSGSINNL (SEQ ID NO: 25).

In some embodiments, the antigen binding molecule or antibody that specifically binds to the anti-CD19 scFv FMC63 (SEQ ID NO: 1), molecules comprising this sequence and cells presenting this sequence, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 19, 20 and 21. In a particular embodiment, the VH CDRs are those presented in FIG. 11.

In some embodiments, the antigen binding molecule or antibody that specifically binds to the anti-CD19 scFv FMC63 (SEQ ID NO: 1), molecules comprising this sequence and cells presenting this sequence, comprises a heavy chain variable region sequence comprising an amino acid sequence of FIG. 11 (SEQ ID NO: 33).

In some embodiments, the antigen binding molecule or antibody that specifically binds to the anti-CD19 scFv FMC63 (SEQ ID NO: 1), molecules comprising this sequence and cells presenting this sequence, comprises the VH framework regions (FRs) described herein. In specific embodiments, the antibody or antigen binding molecule comprises the VH FRs as set forth in, or derivable from, the sequences presented in FIG. 11 (e.g., one, two, three, or four of the FRs in one sequence of FIG. 11).

In some embodiments, the antigen binding molecule or antibody that specifically binds to the anti-CD19 scFv FMC63 (SEQ ID NO: 1), molecules comprising this sequence and cells presenting this sequence, comprises a heavy chain sequence disclosed herein (e.g., in FIG. 11). In some embodiments, the antibody or antigen binding molecule comprises a heavy chain variable region comprising the amino acid sequence of SEQ ID NO: 33.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO: 33.

In some embodiments, an antigen binding molecule or antibody that specifically binds to the anti-CD19 scFv FMC63 (SEQ ID NO: 1), molecules comprising this sequence and cells presenting such molecules, comprises a VL CDR1 comprising, consisting of, or consisting essentially of the amino acid sequence QASQSVYNNDYLS (SEQ ID NO: 29).

In some embodiments, an antigen binding molecule or antibody that specifically binds to the anti-CD19 scFv FMC63 (SEQ ID NO: 1), molecules comprising this sequence and cells presenting such molecules, comprises a VL CDR2 comprising, consisting of, or consisting essentially of the amino acid sequence YASTLAS (SEQ ID NO: 30).

In some embodiments, an antigen binding molecule or antibody that specifically binds to the anti-CD19 scFv FMC63 (SEQ ID NO: 1), molecules comprising this sequence and cells presenting such molecules, comprises a VL CDR3 comprising, consisting of, or consisting essentially of the amino acid sequence AGVKGYSNDNNG (SEQ ID NO: 31).

In some embodiments, an antigen binding molecule or antibody that specifically binds to the anti-CD19 scFv FMC63 (SEQ ID NO: 1), molecules comprising this sequence and cells presenting such molecules, comprises a light chain VL comprising: (a) a VL CDR1 comprising, consisting of, or consisting essentially of the amino acid sequence QASQSVYNNDYLS (SEQ ID NO: 29); and/or (b) a VL CDR2 comprising, consisting of, or consisting essentially of the amino acid sequence YASTLAS (SEQ ID NO: 30); and/or (c) a VL CDR3 comprising, consisting of, or consisting essentially of the amino acid sequence AGVKGYSNDNNG (SEQ ID NO: 31).

Figure 22:
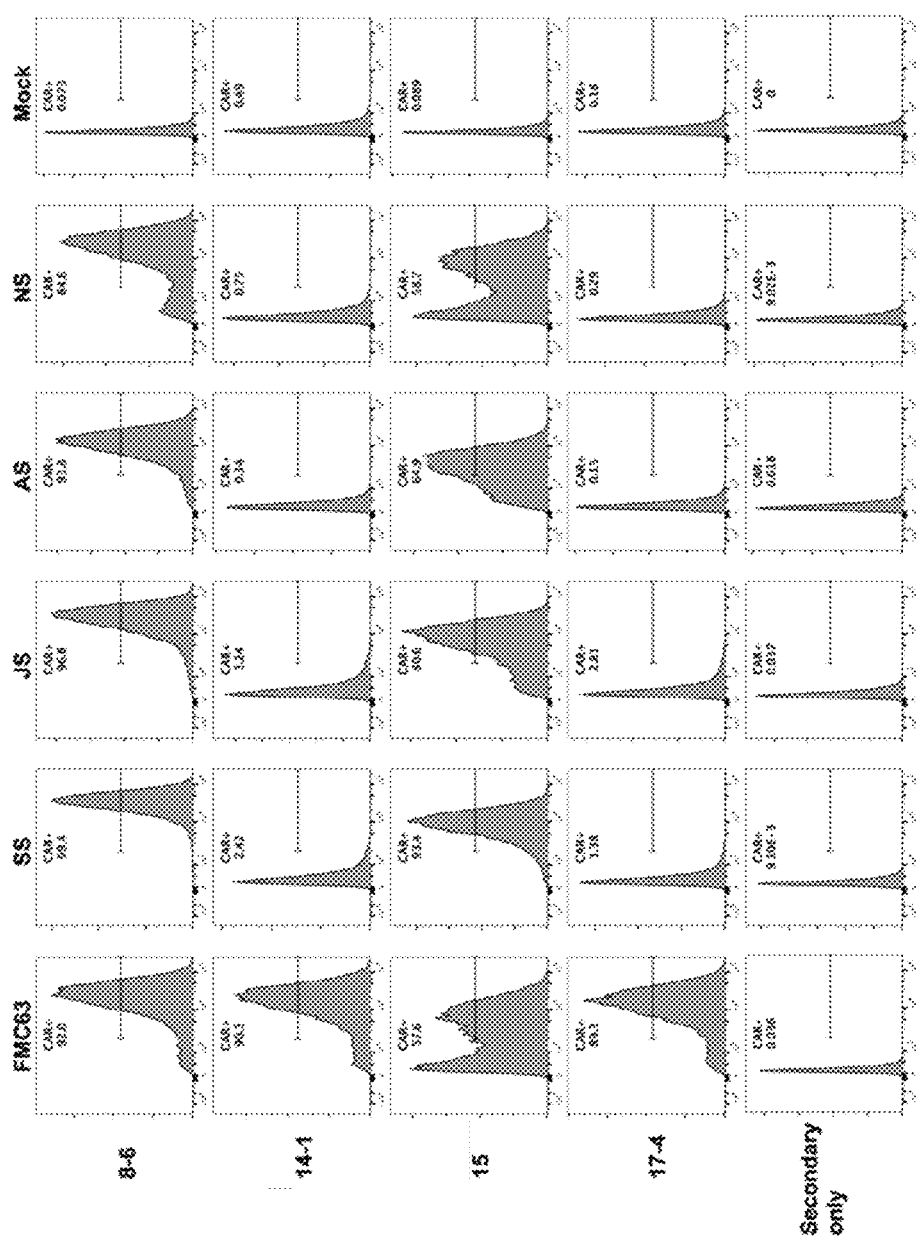
FIG. 22 shows flow cytometry plots used to determine binding of clones 14-1, 15, and 17-4 to FMC63 and humanized variants thereof (SS, JS, AS, NS).

In some embodiments, the antigen binding molecule or antibody that specifically binds to the anti-CD19 scFv FMC63 (SEQ ID NO: 1), molecules comprising this sequence and cells presenting this sequence, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 20, 21 and 22. In a particular embodiment, the VL CDRs are those presented in FIG. 12.

In some embodiments, the antigen binding molecule or antibody that specifically binds to the anti-CD19 scFv FMC63 (SEQ ID NO: 1), molecules comprising this sequence and cells presenting this sequence, comprises a light chain variable region sequence comprising an amino acid sequence of FIG. 12 (SEQ ID NO: 36).

In some embodiments, the antigen binding molecule or antibody that specifically binds to the anti-CD19 scFv FMC63 (SEQ ID NO: 1), molecules comprising this sequence and cells presenting this sequence, comprises the VL framework regions (FRs) described herein. In specific embodiments, the antibody or antigen binding molecule comprises the VL FRs as set forth in, or derivable from, the sequences presented in FIG. 12 (e.g., one, two, three, or four of the FRs in one sequence of FIG. 12).

In some embodiments, the antigen binding molecule or antibody that specifically binds to the anti-CD19 scFv FMC63 (SEQ ID NO: 1), molecules comprising this sequence and cells presenting this sequence, comprises a light chain sequence disclosed herein (e.g., SEQ ID NO: 37 in FIG. 12). In some embodiments, the antibody or antigen binding molecule comprises a light chain variable region comprising the amino acid sequence of SEQ ID NO: 36.

In various embodiments, the light chain variable region is 80%, 85%, 90%, 91%, 92%, 93%, 94%, 95%, 96%, 97%, 98% or 99% identical to the light chain variable region sequence of SEQ ID NO: 36.

In some embodiments, the antibody or antigen binding molecule that specifically binds to the anti-CD19 scFv FMC63 (SEQ ID NO: 1), molecules comprising this sequence and cells presenting this sequence, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region comprising the amino acid sequence of SEQ ID NO: 23; (b) a VH CDR2 region comprising the amino acid sequence of SEQ ID NO: 24; (c) a VH CDR3 region comprising the amino acid sequence of SEQ ID NO: 25; (d) a VL CDR1 region comprising the amino acid sequence of SEQ ID NO: 29; (e) a VL CDR2 region comprising the amino acid sequence of SEQ ID NO: 30; and (f) a VL CDR3 region comprising the amino acid sequence of SEQ ID NO: 31.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 11, 12, respectively, and in FIGS. 19, 20 and 21.

In some embodiments, the antibody or antigen binding molecule that specifically binds to the anti-CD19 scFv FMC63 (SEQ ID NO: 1), molecules comprising this sequence and cells presenting this sequence, comprises a heavy chain variable region sequence disclosed herein (e.g., in FIG. 11) and a light chain variable region sequence disclosed herein (e.g., in FIG. 12).

In some embodiments, the antibody or antigen binding molecule comprises: (a) a heavy chain variable region comprising the amino acid sequence of SEQ ID NO: 33; and (b) a light chain variable region comprising the amino acid sequence of SEQ ID NO: 36. Nucleotide sequences encoding the heavy chain variable region and the light chain variable region are provided in FIGS. 11 and 12, respectively.

In some embodiments, the antibody or antigen binding molecule that specifically binds to the anti-CD19 scFv FMC63 (SEQ ID NO: 1), molecules comprising this sequence and cells presenting this sequence, comprises a heavy chain sequence disclosed herein (e.g., in FIG. 11) and a light chain sequence disclosed herein (e.g., in FIG. 12).

In some embodiments, the antibody or antigen binding molecule comprises: (a) a heavy chain comprising the amino acid sequence of SEQ ID NO: 34; and (b) a light chain comprising the amino acid sequence of SEQ ID NO: 37.

In some embodiments, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 34; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 37.

II.E. Clone 15 (15-7)

In some embodiments, an antigen binding molecule or antibody that specifically binds to the anti-CD19 scFv FMC63 (SEQ ID NO: 1), molecules comprising this sequence and cells presenting such molecules, comprises a VH CDR1 comprising, consisting of, or consisting essentially of the amino acid sequence GFSFTSNY (SEQ ID NO: 41).

In some embodiments, an antigen binding molecule or antibody that specifically binds to the anti-CD19 scFv FMC63 (SEQ ID NO: 1), molecules comprising this sequence and cells presenting such molecules, comprises a VH CDR2 comprising, consisting of, or consisting essentially of the amino acid sequence FLGSSG (SEQ ID NO: 42).

In some embodiments, an antigen binding molecule or antibody that specifically binds to the anti-CD19 scFv FMC63 (SEQ ID NO: 1), molecules comprising this sequence and cells presenting such molecules, comprises a VH CDR3 comprising, consisting of, or consisting essentially of the amino acid sequence DYVNGYDYFNL (SEQ ID NO: 43).

In some embodiments, an antigen binding molecule or antibody that specifically binds to the anti-CD19 scFv FMC63 (SEQ ID NO: 1), molecules comprising this sequence and cells presenting such molecules, comprises a heavy chain VH comprising: (a) a VH CDR1 comprising, consisting of, or consisting essentially of the amino acid sequence GFSFTSNY (SEQ ID NO: 41); and/or (b) a VH CDR2 comprising, consisting of, or consisting essentially of the amino acid sequence FLGSSG (SEQ ID NO: 42); and/or (c) a VH CDR3 comprising, consisting of, or consisting essentially of the amino acid sequence DYVNGYDYFNL (SEQ ID NO: 43).

In some embodiments, the antigen binding molecule or antibody that specifically binds to the anti-CD19 scFv FMC63 (SEQ ID NO: 1), molecules comprising this sequence and cells presenting this sequence, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 19, 20 and 21. In a particular embodiment, the VH CDRs are those presented in FIG. 13.

In some embodiments, the antigen binding molecule or antibody that specifically binds to the anti-CD19 scFv FMC63 (SEQ ID NO: 1), molecules comprising this sequence and cells presenting this sequence, comprises a heavy chain variable region sequence comprising an amino acid sequence of FIG. 13 (SEQ ID NO: 39).

In some embodiments, the antigen binding molecule or antibody that specifically binds to the anti-CD19 scFv FMC63 (SEQ ID NO: 1), molecules comprising this sequence and cells presenting this sequence, comprises the VH framework regions (FRs) described herein. In specific embodiments, the antibody or antigen binding molecule comprises the VH FRs as set forth in, or derivable from, the sequences presented in FIG. 13 (e.g., one, two, three, or four of the FRs in one sequence of FIG. 13).

In some embodiments, the antigen binding molecule or antibody that specifically binds to the anti-CD19 scFv FMC63 (SEQ ID NO: 1), molecules comprising this sequence and cells presenting this sequence, comprises a heavy chain sequence disclosed herein (e.g., SEQ ID NO: 40 in FIG. 13). In some embodiments, the antibody or antigen binding molecule comprises a heavy chain variable region comprising the amino acid sequence of SEQ ID NO: 39.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:39.

In some embodiments, an antigen binding molecule or antibody that specifically binds to the anti-CD19 scFv FMC63 (SEQ ID NO: 1), molecules comprising this sequence and cells presenting such molecules, comprises a VL CDR1 comprising, consisting of, or consisting essentially of the amino acid sequence QSSQSVYNKNLA (SEQ ID NO: 47).

In some embodiments, an antigen binding molecule or antibody that specifically binds to the anti-CD19 scFv FMC63 (SEQ ID NO: 1), molecules comprising this sequence and cells presenting such molecules, comprises a VL CDR2 comprising, consisting of, or consisting essentially of the amino acid sequence STSTLDS (SEQ ID NO: 48).

In some embodiments, an antigen binding molecule or antibody that specifically binds to the anti-CD19 scFv FMC63 (SEQ ID NO: 1), molecules comprising this sequence and cells presenting such molecules, comprises a VL CDR3 comprising, consisting of, or consisting essentially of the amino acid sequence LGSYDCSSADCNA (SEQ ID NO: 49).

In some embodiments, an antigen binding molecule or antibody that specifically binds to the anti-CD19 scFv FMC63 (SEQ ID NO: 1), molecules comprising this sequence and cells presenting such molecules, comprises a light chain VL comprising: (a) a VL CDR1 comprising, consisting of, or consisting essentially of the amino acid sequence QSSQSVYNKNLA (SEQ ID NO: 47); and/or (b) a VL CDR2 comprising, consisting of, or consisting essentially of the amino acid sequence STSTLDS (SEQ ID NO: 48); and/or (c) a VL CDR3 comprising, consisting of, or consisting essentially of the amino acid sequence LGSYDCSSADCNA (SEQ ID NO: 49).

In some embodiments, the antigen binding molecule or antibody that specifically binds to the anti-CD19 scFv FMC63 (SEQ ID NO: 1), molecules comprising this sequence and cells presenting this sequence, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 19, 20 and 21. In a particular embodiment, the VL CDRs are those presented in FIG. 14.

In some embodiments, the antigen binding molecule or antibody that specifically binds to the anti-CD19 scFv FMC63 (SEQ ID NO: 1), molecules comprising this sequence and cells presenting this sequence, comprises a light chain variable region sequence comprising an amino acid sequence of FIG. 14 (SEQ ID NO: 45).

In some embodiments, the antigen binding molecule or antibody that specifically binds to the anti-CD19 scFv FMC63 (SEQ ID NO: 1), molecules comprising this sequence and cells presenting this sequence, comprises the VL framework regions (FRs) described herein. In specific embodiments, the antibody or antigen binding molecule comprises the VL FRs as set forth in, or derivable from, the sequences presented in FIG. 14 (e.g., one, two, three, or four of the FRs in one sequence of FIG. 14).

In some embodiments, the antigen binding molecule or antibody that specifically binds to the anti-CD19 scFv FMC63 (SEQ ID NO: 1), molecules comprising this sequence and cells presenting this sequence, comprises a light chain sequence disclosed herein (e.g., SEQ ID NO: 46 in FIG. 14). In some embodiments, the antibody or antigen binding molecule comprises a light chain variable region comprising the amino acid sequence of SEQ ID NO: 45.

In various embodiments, the light chain variable region is 80%, 85%, 90%, 91%, 92%, 93%, 94%, 95%, 96%, 97%, 98% or 99% identical to the light chain variable region sequence of SEQ ID NO: 45.

In some embodiments, the antibody or antigen binding molecule that specifically binds to the anti-CD19 scFv FMC63 (SEQ ID NO: 1), molecules comprising this sequence and cells presenting this sequence, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region comprising the amino acid sequence of SEQ ID NO: 41; (b) a VH CDR2 region comprising the amino acid sequence of SEQ ID NO: 42; (c) a VH CDR3 region comprising the amino acid sequence of SEQ ID NO: 43; (d) a VL CDR1 region comprising the amino acid sequence of SEQ ID NO: 47; (e) a VL CDR2 region comprising the amino acid sequence of SEQ ID NO: 48; and (f) a VL CDR3 region comprising the amino acid sequence of SEQ ID NO: 49.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 13, 14, respectively, and in FIGS. 19, 20 and 21.

In some embodiments, the antibody or antigen binding molecule that specifically binds to the anti-CD19 scFv FMC63 (SEQ ID NO: 1), molecules comprising this sequence and cells presenting this sequence, comprises a heavy chain variable region sequence disclosed herein (e.g., in FIG. 13) and a light chain variable region sequence disclosed herein (e.g., in FIG. 14).

In some embodiments, the antibody or antigen binding molecule comprises: (a) a heavy chain variable region comprising the amino acid sequence of SEQ ID NO: 39; and (b) a light chain variable region comprising the amino acid sequence of SEQ ID NO: 45. Nucleotide sequences encoding the heavy chain variable region and the light chain variable region are provided in FIGS. 13 and 14, respectively.

In some embodiments, the antibody or antigen binding molecule that specifically binds to the anti-CD19 scFv FMC63 (SEQ ID NO: 1), molecules comprising this sequence and cells presenting this sequence, comprises a heavy chain sequence disclosed herein (e.g., in FIG. 13) and a light chain sequence disclosed herein (e.g., in FIG. 14).

In some embodiments, the antibody or antigen binding molecule comprises: (a) a heavy chain comprising the amino acid sequence of SEQ ID NO: 40; and (b) a light chain comprising the amino acid sequence of SEQ ID NO: 46.

In some embodiments, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 40; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 46.

II.F. Clone 17

In some embodiments, an antigen binding molecule or antibody that specifically binds to the anti-CD19 scFv FMC63 (SEQ ID NO: 1), molecules comprising this sequence and cells presenting such molecules, comprises a VH CDR1 comprising, consisting of, or consisting essentially of the amino acid sequence GFSFSDSW (SEQ ID NO: 53).

In some embodiments, an antigen binding molecule or antibody that specifically binds to the anti-CD19 scFv FMC63 (SEQ ID NO: 1), molecules comprising this sequence and cells presenting such molecules, comprises a VH CDR2 comprising, consisting of, or consisting essentially of the amino acid sequence YTGDG (SEQ ID NO: 54).

In some embodiments, an antigen binding molecule or antibody that specifically binds to the anti-CD19 scFv FMC63 (SEQ ID NO: 1), molecules comprising this sequence and cells presenting such molecules, comprises a VH CDR3 comprising, consisting of, or consisting essentially of the amino acid sequence GAQFYL (SEQ ID NO: 55).

In some embodiments, an antigen binding molecule or antibody that specifically binds to the anti-CD19 scFv FMC63 (SEQ ID NO: 1), molecules comprising this sequence and cells presenting such molecules, comprises a heavy chain VH comprising: (a) a VH CDR1 comprising, consisting of, or consisting essentially of the amino acid sequence GFSFTSNY (SEQ ID NO: 53); and/or (b) a VH CDR2 comprising, consisting of, or consisting essentially of the amino acid sequence FLGSSG (SEQ ID NO: 54); and/or (c) a VH CDR3 comprising, consisting of, or consisting essentially of the amino acid sequence DYVNGYDYFNL (SEQ ID NO: 55).

In some embodiments, the antigen binding molecule or antibody that specifically binds to the anti-CD19 scFv FMC63 (SEQ ID NO: 1), molecules comprising this sequence and cells presenting this sequence, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 19, 20 and 21. In a particular embodiment, the VH CDRs are those presented in FIG. 15.

In some embodiments, the antigen binding molecule or antibody that specifically binds to the anti-CD19 scFv FMC63 (SEQ ID NO: 1), molecules comprising this sequence and cells presenting this sequence, comprises a heavy chain variable region sequence comprising an amino acid sequence of FIG. 15 (SEQ ID NO: 51).

In some embodiments, the antigen binding molecule or antibody that specifically binds to the anti-CD19 scFv FMC63 (SEQ ID NO: 1), molecules comprising this sequence and cells presenting this sequence, comprises the VH framework regions (FRs) described herein. In specific embodiments, the antibody or antigen binding molecule comprises the VH FRs as set forth in, or derivable from, the sequences presented in FIG. 15 (e.g., one, two, three, or four of the FRs in one sequence of FIG. 15).

In some embodiments, the antigen binding molecule or antibody that specifically binds to the anti-CD19 scFv FMC63 (SEQ ID NO: 1), molecules comprising this sequence and cells presenting this sequence, comprises a heavy chain sequence disclosed herein (e.g., SEQ ID NO: 52 in FIG. 15). In some embodiments, the antibody or antigen binding molecule comprises a heavy chain variable region comprising the amino acid sequence of SEQ ID NO: 51.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:51.

In some embodiments, an antigen binding molecule or antibody that specifically binds to the anti-CD19 scFv FMC63 (SEQ ID NO: 1), molecules comprising this sequence and cells presenting such molecules, comprises a VL CDR1 comprising, consisting of, or consisting essentially of the amino acid sequence QSSQSVYANTYLS (SEQ ID NO: 59).

In some embodiments, an antigen binding molecule or antibody that specifically binds to the anti-CD19 scFv FMC63 (SEQ ID NO: 1), molecules comprising this sequence and cells presenting such molecules, comprises a VL CDR2 comprising, consisting of, or consisting essentially of the amino acid sequence SASSLAS (SEQ ID NO: 60).

In some embodiments, an antigen binding molecule or antibody that specifically binds to the anti-CD19 scFv FMC63 (SEQ ID NO: 1), molecules comprising this sequence and cells presenting such molecules, comprises a VL CDR3 comprising, consisting of, or consisting essentially of the amino acid sequence LGRYSCGLADCAA (SEQ ID NO: 61).

In some embodiments, an antigen binding molecule or antibody that specifically binds to the anti-CD19 scFv FMC63 (SEQ ID NO: 1), molecules comprising this sequence and cells presenting such molecules, comprises a light chain VL comprising: (a) a VL CDR1 comprising, consisting of, or consisting essentially of the amino acid sequence QSSQSVYANTYLS (SEQ ID NO: 59); and/or (b) a VL CDR2 comprising, consisting of, or consisting essentially of the amino acid sequence SASSLAS (SEQ ID NO: 60); and/or (c) a VL CDR3 comprising, consisting of, or consisting essentially of the amino acid sequence LGRYSCGLADCAA (SEQ ID NO: 61).

In some embodiments, the antigen binding molecule or antibody that specifically binds to the anti-CD19 scFv FMC63 (SEQ ID NO: 1), molecules comprising this sequence and cells presenting this sequence, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 20, 21 and 22. In a particular embodiment, the VL CDRs are those presented in FIG. 21.

In some embodiments, the antigen binding molecule or antibody that specifically binds to the anti-CD19 scFv FMC63 (SEQ ID NO: 1), molecules comprising this sequence and cells presenting this sequence, comprises a light chain variable region sequence comprising an amino acid sequence of FIG. 16 (SEQ ID NO: 57).

In some embodiments, the antigen binding molecule or antibody that specifically binds to the anti-CD19 scFv FMC63 (SEQ ID NO: 1), molecules comprising this sequence and cells presenting this sequence, comprises the VL framework regions (FRs) described herein. In specific embodiments, the antibody or antigen binding molecule comprises the VL FRs as set forth in, or derivable from, the sequences presented in FIG. 16 (e.g., one, two, three, or four of the FRs in one sequence of FIG. 16).

In some embodiments, the antigen binding molecule or antibody that specifically binds to the anti-CD19 scFv FMC63 (SEQ ID NO: 1), molecules comprising this sequence and cells presenting this sequence, comprises a light chain sequence disclosed herein (e.g., SEQ ID NO: 58 in FIG. 16). In some embodiments, the antibody or antigen binding molecule comprises a light chain variable region comprising the amino acid sequence of SEQ ID NO: 57.

In various embodiments, the light chain variable region is 80%, 85%, 90%, 91%, 92%, 93%, 94%, 95%, 96%, 97%, 98% or 99% identical to the light chain variable region sequence of SEQ ID NO:57.

In some embodiments, the antibody or antigen binding molecule that specifically binds to the anti-CD19 scFv FMC63 (SEQ ID NO: 1), molecules comprising this sequence and cells presenting this sequence, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region comprising the amino acid sequence of SEQ ID NO: 53; (b) a VH CDR2 region comprising the amino acid sequence of SEQ ID NO: 54; (c) a VH CDR3 region comprising the amino acid sequence of SEQ ID NO: 55; (d) a VL CDR1 region comprising the amino acid sequence of SEQ ID NO: 59; (e) a VL CDR2 region comprising the amino acid sequence of SEQ ID NO: 60; and (f) a VL CDR3 region comprising the amino acid sequence of SEQ ID NO: 61.

In some embodiments, the antibody or antigen binding molecule that specifically binds to the anti-CD19 scFv FMC63 (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 15, 16, respectively, and in FIGS. 19, 20 and 21.

In some embodiments, the antibody or antigen binding molecule that specifically binds to the anti-CD19 scFv FMC63 (SEQ ID NO: 1), molecules comprising this sequence and cells presenting this sequence, comprises a heavy chain variable region sequence disclosed herein (e.g., in FIG. 15) and a light chain variable region sequence disclosed herein (e.g., in FIG. 16).

In some embodiments, the antibody or antigen binding molecule comprises: (a) a heavy chain variable region comprising the amino acid sequence of SEQ ID NO: 45; and (b) a light chain variable region comprising the amino acid sequence of SEQ ID NO: 57. Nucleotide sequences encoding the heavy chain variable region and the light chain variable region are provided in FIGS. 15 and 16, respectively.

In some embodiments, the antibody or antigen binding molecule that specifically binds to the anti-CD19 scFv FMC63 (SEQ ID NO: 1), molecules comprising this sequence and cells presenting this sequence, comprises a heavy chain sequence disclosed herein (e.g., in FIG. 15) and a light chain sequence disclosed herein (e.g., in FIG. 16).

In some embodiments, the antibody or antigen binding molecule comprises: (a) a heavy chain comprising the amino acid sequence of SEQ ID NO: 52; and (b) a light chain comprising the amino acid sequence of SEQ ID NO: 58.

In some embodiments, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 52; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 58.

III. Polynucleotides Encoding Antibodies and Other Antigen Binding Molecules The present invention is also directed to polynucleotides encoding antibodies and other antigen binding molecules that specifically bind to the anti-CD19 scFv FMC63 (SEQ ID NO: 1), molecules comprising this sequence and cells presenting this sequence.

In some embodiments, a polynucleotide of the present invention encodes an antigen binding molecule, wherein the antigen binding molecule comprises a heavy chain variable region amino acid sequence that is at least about 75%, at least about 85%, at least about 85%, at least about 90%, at least about 95%, at least about 96%, at least about 97%, at least about 98%, at least about 99%, or 100% identical to a heavy chain variable region amino acid sequence selected from the group consisting of SEQ ID NOs: 3, 15, 21, 33, 39 and 51.

In some embodiments, a polynucleotide of the present invention encodes antigen binding molecule, wherein the antigen binding molecule comprises a light chain variable amino acid sequence that is at least about 75%, at least about 85%, at least about 85%, at least about 90%, at least about 95%, at least about 96%, at least about 97%, at least about 98%, at least about 99%, or 100% identical to a light chain variable region amino acid sequence selected from the group consisting of SEQ ID NOs: 8, 18, 27, 36, 45 and 57.

In certain embodiments, the polynucleotide comprises a heavy chain coding sequence selected from the group consisting of SEQ ID NO: 2, SEQ ID NO: 14, SEQ ID NO: 20, SEQ ID NO: 32, SEQ ID NO: 38 and SEQ ID NO: 50. In another embodiment, the polynucleotide comprises a light chain coding sequence selected from the group consisting of SEQ ID NO: 8, SEQ ID NO: 17, SEQ ID NO: 26, SEQ ID NO: 35, SEQ ID NO: 44 and SEQ ID NO: 56.

As will be appreciated by those of skill in the art, variations of the disclosed polynucleotide sequences are possible due to the degeneracy of the genetic code. Such variants of the disclose polynucleotide sequences thus form an aspect of the instant disclosure.

IV. Vectors, Cells, and Pharmaceutical Compositions

In certain aspects, provided herein are vectors comprising a polynucleotide disclosed herein. In some embodiments, the present invention is directed to a vector or a set of vectors comprising a polynucleotide(s) encoding an amino acid sequence of an antibody or antigen binding molecule that specifically binds to the anti-CD19 scFv FMC63 (SEQ ID NO: 1), molecules comprising this sequence and cells presenting this sequence, as described herein.

Any vector known in the art can be suitable for expressing the antibodies and other antigen binding molecules of the present invention. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are cells comprising a polynucleotide or a vector of the present invention. In some embodiments, the present invention is directed to cells, in vitro cells, comprising a polynucleotide encoding an antigen binding molecule, as described herein. In some embodiments, the present invention is directed to cells, e.g., in vitro cells, comprising a polynucleotide encoding an antibody or an antigen binding molecule thereof that specifically binds to the anti-CD19 scFv FMC63 (SEQ ID NO: 1), molecules comprising this sequence and cells presenting this sequence, as disclosed herein.

Any cell can be used as a host cell for the polynucleotides and vectors encoding all or a fragment of the antibodies and other antigen binding molecules of the present invention. In some embodiments, a host cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, a host cell is a human cell. In some embodiments, a host cell is a CHO cell and in other embodiments a host cell is a sP2/0 or other murine cell. A host cell of the present invention can be obtained through any source known in the art.

Other aspects of the present invention are directed to compositions comprising a polynucleotide described herein, a vector described herein, an antibody and/or an antigen binding molecule described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In some embodiments, the composition comprises a polynucleotide encoding an antibody or antigen binding molecule that specifically binds to that specifically binds to the anti-CD19 scFv FMC63 (SEQ ID NO: 1), molecules comprising this sequence and cells presenting this sequence. In another embodiment, the composition comprises an antigen binding molecule encoded by a polynucleotide of the present invention, wherein the antigen binding molecule specifically binds to the anti-CD19 scFv FMC63 (SEQ ID NO: 1), molecules comprising this sequence and cells presenting this sequence, as disclosed herein. In another embodiment, the composition comprises an in vitro cell comprising a polynucleotide encoding an antibody or an antigen binding molecule thereof encoded by a polynucleotide of the present invention.

In some embodiments, the composition comprises one antibody or antigen binding molecule that specifically binds to the anti-CD19 scFv FMC63 (SEQ ID NO: 1), molecules comprising this sequence and cells presenting this sequence, as disclosed herein. In some embodiments, the composition comprises more than one antibody or antigen binding molecule that specifically binds to the anti-CD19 scFv FMC63 (SEQ ID NO: 1), molecules comprising this sequence and cells presenting this sequence, as disclosed herein, wherein the antibodies or antigen binding molecules bind more than one epitope. In some embodiments, the antibodies or antigen binding molecules will not compete with one another for binding to that epitope. In some embodiments, two or more of the antibodies or antigen binding molecules provided herein are combined together in a pharmaceutical composition. Preferably such a composition will be suitable for administration to a subject, including a human.

V. Exemplary Methods

The following section describes various exemplary methods of using the disclosed antigen binding molecules herein. Any antigen binding molecule disclosed herein can be employed in the disclosed methods.

In various embodiments of the disclosed methods, the antigen binding molecule is selected from the group consisting of an antibody, an scFv, a Fab, a Fab', a Fv, a F(ab')$_2$, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody an IgG2 antibody having at least one mutation in the hinge region, an IgG3 antibody, an IgG1 antibody having at least one mutation in the hinge region, an IgG4 antibody, an IgG4 antibody having at least one mutation in the hinge region, an antibody comprising at least one non-naturally occurring amino acid, and any combination thereof.

In some of the disclosed methods T cells can be employed. Such T cells can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

In various embodiments of the disclosed methods, an antigen binding molecule specifically binds to the anti-CD19 scFv FMC63 (SEQ ID NO: 1), molecules comprising this sequence and cells presenting this sequence, as disclosed herein. In further embodiments of the disclosed methods, the antigen binding molecule comprises one or more of (a) a light chain CDR1, (b) a light chain CDR2, (c) a light chain CDR3, (d) a heavy chain CDR1, (e) a heavy chain CDR2, and (f) a heavy chain CDR3. In additional embodiments of the disclosed methods, an antigen binding molecule comprises a heavy chain CDR3 comprising one of SEQ ID NOs: 7, 25, 43, 55, or a light chain CDR3 comprising one of SEQ ID NOs: 13, 31, 49, 61, or both the heavy and light chain CDR3s. In other embodiments of the disclosed methods, the antigen binding molecule comprises a heavy chain CDR1 comprising an amino acid sequence comprising one of SEQ ID NOs: 5, 23, 41 and 53, or a heavy chain CDR2 comprising the amino acid sequence of one of SEQ ID NOs: 6, 24, 42 and 54, or a light chain CDR1 comprising the amino acid sequence of one of SEQ ID NOs: 11, 29, 47 and 59 or a light chain CDR2 comprising the amino acid sequence of one of SEQ ID NOs: 12, 30, 48 and 60. Referring to the Figures, in various embodiments of the disclosed methods, the antigen binding molecule comprises a heavy chain CDR1, a heavy chain CDR2, a heavy chain CDR3, a light chain CDR1, a light chain CDR2, and a light chain CDR3, each CDR comprising an amino acid sequence shown in FIGS. 5-21.

In various embodiments of the disclosed methods, an antigen binding molecule comprises a heavy chain (HC), and the HC comprises a heavy chain variable region (VH) sequence comprising one of SEQ ID NOs: 3, 15, 21, 33, 39 and 51. Referring to the figures, in various embodiments of the disclosed methods the heavy chain comprises a heavy chain CDR1, a heavy chain CDR2, and a heavy chain CDR3, each CDR comprising an amino acid sequence shown in FIGS. 5-21. Moreover, in embodiments of the disclosed methods, an antigen binding molecule can be employed which comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule of claim disclosed herein (e.g., an antigen binding molecules comprising a variable region (VH) sequence comprising one of SEQ ID NOs: 3, 15, 21, 33, 39 and 51).

In various embodiments of the disclosed methods, an antigen binding molecule comprises a light chain (LC), and the LC can comprise a heavy chain variable region (VL) sequence comprising one of SEQ ID NOs: 9, 18, 27, 36, 44 and 57. Referring to the figures, in various embodiments of the disclosed methods the light chain comprises a light chain CDR1, a light chain CDR2, and a light chain CDR3, each CDR comprising an amino acid sequence shown in FIGS. 5-21. Moreover, in embodiments of the disclosed methods, an antigen binding molecule can be employed which comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VL of an antigen binding molecule of claim disclosed herein (e.g., an antigen binding molecules comprising a variable region (VL) sequence comprising SEQ ID NO: 9, 18, 27, 36, 44 and 57).

In view of the above description of antigen binding molecules that can be employed in the disclosed methods, representative methods will now be discussed in more detail.

Va. Method of Administering a Dose of a Medicament to a Subject

In one aspect, a method of administering a dose of a medicament to a subject, the dose comprising a preselected number of cells presenting a therapeutic molecule comprising the anti-CD19 scFv FMC63 (SEQ ID NO: 1), is provided.

In specific embodiments, the dose comprises $0.5 \times 10^6$ cells per kilogram of the subject, $1.0 \times 10^6$ cells per kilogram of the subject, $2.0 \times 10^6$ cells per kilogram of the subject, $3.0 \times 10^6$ cells per kilogram of the subject, $4.0 \times 10^6$ cells per kilogram of the subject, or $5.0 \times 10^6$ cells per kilogram of the subject, although the method can be employed using any dose. $1.0 \times 10^6$ cells per kilogram of the subject is a preferred dose.

Consistent with the definition provided herein, in various embodiments, a subject is a human or non-human subject. When the subject is a human, the subject can be, e.g., any human who is being treated for an abnormal physiological condition, such as cancer or has been formally diagnosed with a disorder, those without formally recognized disorders, those receiving medical attention, those at risk of developing the disorders, those being studied for the presence or absence of a disorder, etc.

Initially, a sample of known volume comprising a population comprising a known number of cells, which cells are known or suspected to be presenting a molecule comprising SEQ ID NO: 1, is provided. In the disclosed method, the number of cells can be determined using any known method. In preferred embodiments the cells are counted using an automated apparatus, such as a cell sorter (e.g., a FACS), however traditional non-automated cell counting methods can also be employed.

The cells of the method can comprise any type of cell, with immune cells (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of cell can be employed in the method, and the cell can be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, etc. Gradient purification, cell culture selection and/or cell sorting can also be employed in obtaining T cells.

The therapeutic molecule expressed by the cell can comprise any molecule known or suspected to provide a therapeutic benefit to a subject to which is it administered. Thus, a therapeutic molecule can be a peptide or polypeptide of any structure or design. Preferably the SEQ ID NO: 1 component is expressed or disposed, at least in part, extracellularly, i.e., to a degree that it can be recognized by an extracellular interaction partner such as the antigen binding molecules of the instant disclosure.

In specific embodiments, the therapeutic molecule is a CAR. When the therapeutic molecule is a CAR it can comprise a molecule, or fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14) NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof.

Continuing, an aliquot of the sample comprising a population of cells presenting a molecule comprising the anti-CD19 scFv FMC63 sequence (SEQ ID NO: 1) is provided. The aliquot can be obtained using any convenient means, such as by a cell sorter, by a simply pipetting of material out of the sample, etc.

Additionally, an antigen binding molecule that specifically binds the anti-CD19 scFv FMC63 (SEQ ID NO: 1) further comprising a detectable label is provided. The antigen binding molecule is preferably an antigen binding molecule disclosed herein, e.g., in the figures, sequence listing or the instant disclosure. Any detectable label can be employed in the method, as described herein, and suitable labels can be selected using a desired set of criteria. Examples of types of detectable labels include fluorescent labels (e.g., an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry). Suitable optical dyes, including fluoro-phores, are described in Johnson, Molecular Probes Handbook: A Guide to Fluorescent Probes and Labeling Techniques, 11$^{th}$ Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I), photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc. Strategies for the labeling of proteins are known in the art and can be employed in the disclosed method.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds SEQ ID NO: 1 (or fragment thereof) can be employed. Multiple examples of suitable antigen binding molecules are provided herein, e.g., those having one or more of the CDRs shown in FIGS. 5-21.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Continuing, the aliquot of the sample is contacted with the antigen binding molecule under conditions that permit the formation of a binding complex comprising a cell present in the sample and the antigen binding molecule. Thus, the result of this step of the method is the formation of a binding complex in which the antigen binding molecule, with which a detectable label is associated, is bound to the cell expressing the therapeutic molecule, which comprises the anti-CD19 scFv FMC63 sequence (SEQ ID NO: 1). Thus, the binding complex itself is detectable. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

The fraction of cells present in a binding complex in the aliquot is then determined. This calculation can be performed by comparing the number of cells bearing the detectable label to those that do not, and can be represented as percentage. The number of cells in binding complexes can be determined. The specific method employed to determine the number of cells present in a binding complex will be dependent on the nature of the label selected. For example, FACS can be employed when a fluorescent label is selected; when an isotope label is selected mass spectrometry, NMR or other technique can be employed; magnetic-based cell sorting can be employed when a magnetic label is chosen; microscopy can also be employed. The number of cells in the sample is known ab initio and thus the fraction of cells present in a binding complex can be easily determined.

Continuing, the concentration of cells in the initial sample expressing a molecule comprising the anti-CD19 scFv FMC63 (SEQ ID NO: 1) is determined; the determination is based on the fraction of cells determined to be present in the binding complex, and thus expressing the therapeutic protein bearing a detectable label.

The fraction of cells presenting the therapeutic protein is known, and the volume of the aliquot is known; thus a simple comparison of the number of cells in the sample from which the aliquot was taken that are expressing the therapeutic molecule to the volume of the larger sample provides the fraction of the cells in the sample bearing the therapeutic molecule on a therapeutic molecule/volume basis (i.e., the concentration of cells bearing the therapeutic molecule in the larger sample).

The volume of the sample that comprises the selected number of cells is then determined, by extrapolation based on the concentration of cells bearing therapeutic molecule present in the sample.

Finally, the volume of sample comprising the desired number of cells is administered to the subject. The administration can comprise an aspect of a therapeutic regimen based on the therapeutic molecule present in the sample and expressed by the cells in the sample.

Although the administration can be performed one time or more than one time, an advantage of the method is that by administering a dose comprising the preselected number of cells, which number of cells will be determined based on a known or expected efficacy, unnecessary administration of cells presenting the therapeutic molecule is avoided; i.e., the subject receives the correct number of cells to provide a desired therapeutic benefit and is not overdosed with cells.

Vb. Method of Determining a Number of Cells Presenting a Molecule of Interest

There are situations in which it may be desirable to determine the number of cells present in a sample. For example, it may be desirable to determine the number of immune cells present a sample obtained from a subject. Or it may be desirable to determine the number of cells transfected and expressing a construct, which can be used as a measure of the level of efficiency of the transfection. The disclosed method can be employed in these and other applications in which it is desirable to determine the number of cells present in a sample.

Thus, a method of determining a number of cells presenting a molecule in a sample wherein the molecule comprising the anti-CD19 scFv FMC63 (SEQ ID NO: 1) is provided.

In one embodiment, a sample comprising cells known or suspected to be expressing a molecule comprising the amino acid sequence of the anti-CD19 scFv FMC63 (SEQ ID NO: 1) is provided.

The cell can be of any type, and can be human or non-human (e.g., mouse, rate, rabbit, hamster, etc). In one preferred embodiment, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method, and the cell can be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc.

In specific embodiments, the molecule comprising the anti-CD19 scFv FMC63 (SEQ ID NO: 1) is a CAR. When the molecule is a CAR it can comprise a molecule, or fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CD1-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof.

The sample is then contacted with an antigen binding molecule that specifically binds SEQ ID NO: 1 and comprises a detectable label, under conditions that permit the formation of a binding complex comprising a cell present in the sample and the antigen binding molecule. The antigen binding molecule is preferably an antigen binding molecule (or fragment thereof) disclosed herein, e.g., in the figures, sequence listing or the instant section of the disclosure. Any antigen binding molecule that specifically binds SEQ ID NO: 1 can be employed in the disclosed method. Multiple examples of suitable antigen binding molecules are provided herein, e.g., those having one or more of the CDRs shown in FIG. 5-21.

Any detectable label can be employed in the method, as described herein, and suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science). Suitable optical dyes, including fluoro-phores, are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I $^{125}$I, $^{131}$I), photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc. Strategies for the labeling of proteins are well known in the art and can be employed in the disclosed method. See, e.g., Obermaier et al., (2015) *Methods Mol Biol* 1295:153-65; Strack (2016) *Nature Methods* 13:33; *Site-Specific Protein Labeling: Methods and Protocols*, (Gautier and Hinner, eds.) 2015, Springer.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds the anti-CD19 scFv FMC63 sequence (SEQ ID NO: 1) (or fragment thereof) can be employed, such as those disclosed herein, e.g., those having one or more of the CDRs shown in FIGS. 5-21.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

Continuing, the number of cells present in a binding complex in the sample is determined. The specific method employed to determine the number of cells present in a binding complex will be dependent on the nature of the label selected. For example, FACS can be employed when a fluorescent label is selected; when an isotope label is selected mass spectrometry, NMR or other technique can be employed; magnetic-based cell sorting can be employed when a magnetic label is chosen; microscopy can also be employed. The output of these detection methods can be in the form of a number of cells or the output can be of a form that allows the calculation of the number of cells based on the output.

Vc. Method of Isolating a Molecule

It is of tremendous value to have the ability to separate different populations of molecules, and particularly biologically-relevant molecules, from one another. Using the antigen binding molecules provided herein, such separation can be achieved and employed in a range of biotechnological, biopharmaceutical and therapeutic applications. Thus, in one aspect of the instant disclosure, a method of isolating a molecule comprising the anti-CD19 scFv FMC63 (SEQ ID NO: 1) is provided.

In some embodiments, the method comprises providing a sample known or suspected to comprise a molecule comprising the anti-CD19 scFv FMC63 (SEQ ID NO: 1).

In specific embodiments, the molecule comprising the anti-CD19 scFv FMC63 (SEQ ID NO: 1) is a CAR. When the molecule is a CAR it can comprise a molecule, or fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof.

An antigen binding molecule that specifically binds the anti-CD19 scFv FMC63 sequence (SEQ ID NO: 1) and optionally comprises a detectable label is provided. When it is decided to employ a detectable label, any detectable label can be employed in the method, as described herein, and suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I $^{125}$I, $^{131}$I), Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus*, or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc can also be employed. Strategies for the labeling of proteins are well known in the art and can be employed in the disclosed method. See, e.g., Obermaier et al., (2015) *Methods Mol Biol* 1295:153-65; Strack (2016) *Nature Methods* 13:33; *Site-Specific Protein Labeling: Methods and Protocols*, (Gautier and Hinner, eds.) 2015, Springer.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds anti-CD19 scFv FMC63 sequence (SEQ ID NO: 1) (or fragment thereof) can be employed, such as those disclosed herein, e.g., those having one or more of the CDRs shown in FIGS. 5-21.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

At this stage, no binding complexes may have formed, or a plurality of binding complexes comprising one or more antigen binding molecules bound to a molecule comprising SEQ ID NO: 1 (or one or more molecules comprising SEQ ID NO: 1 bound to an antigen binding molecule) may have formed. Unbound molecules comprising SEQ ID NO: 1 and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. If a binding complex is disposed on a bead, the bead itself may be situated in a column or other structure and the same approach can be used.

The solution used to induce the formation of binding complexes can be used, for example, as a wash solution to remove unbound components. Any suitable buffer or solution that does not disrupt formed binding complexes can also be used. Typically, buffers having high salt concentrations, non-physiological pH, containing chaotropes or denaturants, are preferably avoided when performing this step of the method.

A formed binding complex is then separated into (a) a molecule comprising SEQ ID NO: 1, and (b) an antigen binding molecule. The separation can be achieved using standard methodologies known to those of skill in the art. For example, a solution of suitable pH and composition can be washed over the complexes. A solution that is commonly employed for this purpose is 0.1 M glycine HCl, pH 2.5-3.0, and this solution can be employed to achieve the separation. Other solutions that can be employed include 100 mM citric acid, pH 3.0, 50-100 mM triethylamine or triethanolamine, pH 11.5; 150 mM ammonium hydroxide, pH 10.5; 0.1 M glycine.NaOH, pH 10.0; 5 M lithium chloride, 3.5 M magnesium or potassium chloride, 3.0 M potassium chloride, 2.5 M sodium or potassium iodide, 0.2-3.0 M sodium thiocyanate, 0.1 M Tris-acetate with 2.0 M NaCl, pH 7.7; 2-6 M guanidine HCl, 2-8 M urea, 1.0 M ammonium thiocyanate, 1% sodium deoxycholate 1% SDS; and 10% dioxane 50% ethylene glycol, pH 8-11.5.

Following the separation, if the molecule comprising SEQ ID NO: 1 is of primary interest it can be collected; alternatively, if the antigen binding molecule is of primary interest it can be collected.

Vd. Method of Determining the Presence or Absence of a Molecule

As disclosed herein, it may sometimes be desirable to isolate a molecule comprising the anti-CD19 scFv FMC63 sequence (SEQ ID NO: 1), as provided herein. In other cases, simply knowing whether a molecule comprising SEQ ID NO: 1 provided herein is present or absent from a sample is enough information. For example, it may be beneficial to know that such a molecule is being expressed, regardless of the level of expression. In other cases, it may be desirable to know if a purification process or step designed to remove such a molecule has been effectively performed. Thus, the qualitative determination of the presence or absence of a molecule comprising the anti-CD19 scFv FMC63 sequence (SEQ ID NO: 1) of the instant disclosure can be useful in multiple applications. In view thereof, a method of determining the presence or absence of a molecule comprising SEQ ID NO: 1 in a sample is provided.

In some embodiments, the method comprises providing a sample known or suspected to comprise a molecule comprising SEQ ID NO: 1.

In some embodiments, the molecule comprising SEQ ID NO: 1 is a CAR. When the molecule is a CAR it can comprise a molecule, or fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof.

An antigen binding molecule comprising a detectable label that specifically binds the anti-CD19 scFv FMC63 (SEQ ID NO: 1) is provided. Suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science). Suitable optical dyes, including fluoro-phores, are described in Johnson, *Molecular Probes Handbook: A Guide to Fluorescent Probes and Labeling Techniques,* 11$^{th}$ *Edition*, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I $^{125}$I, $^{131}$I), photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNA-BEADS), etc. Strategies for the labeling of proteins are well known in the art and can be employed in the disclosed method. See, e.g., Obermaier et al., (2015) *Methods Mol Biol* 1295:153-65; Strack (2016) *Nature* Methods 13:33; *Site-Specific Protein Labeling: Methods and Protocols*, (Gautier and Hinner, eds.) 2015, Springer.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds the anti-CD19 scFv FMC63 sequence (SEQ ID NO: 1 or fragment thereof) can be employed, such as those disclosed herein, e.g., those having one or more of the CDRs shown in FIGS. 5-21.

Continuing, the sample is contacted with the antigen binding molecule under conditions that permit the formation of a binding complex comprising a molecule comprising SEQ ID NO: 1 (which can be presented on a cell) present in the sample and the antigen binding molecule. The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

At this stage, no binding complexes may have formed, or a plurality of binding complexes comprising one or more antigen binding molecules bound to a molecule comprising the anti-CD19 scFv FMC63 sequence (SEQ ID NO: 1) (or one or more molecules comprising SEQ ID NO: 1 bound to an antigen binding molecule) may have formed. Unbound molecules comprising SEQ ID NO: 1 and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. If a binding complex is disposed on a bead, the bead itself may be situated in a column or other structure and the same approach can be used.

The solution used to induce the formation of binding complexes can be used, for example, as a wash solution to remove unbound components. Any suitable buffer or solution that does not disrupt formed binding complexes can also be used. Typically, buffers having high salt concentrations, non-physiological pH, containing chaotropes or denaturants, should be avoided when performing this step of the method.

Lastly, the presence or absence of a binding complex—which will comprise a molecule comprising SEQ ID NO: 1 and an antigen binding molecule—is detected. The specific method employed to detect the presence or absence of a binding complex will be dependent on the nature of the label selected. For example, flow cytometry or FACS can be employed when a fluorescent label is selected; when an isotope label is selected mass spectrometry, NMR or other technique can be employed; magnetic-based cell sorting can be employed when a magnetic label is chosen; microscopy can also be employed. The end result of the method is a qualitative assessment of the presence or absence of the antigen binding molecule comprising the detectable label, and thus, the presence or absence of its binding partner, the molecule comprising SEQ ID NO: 1.

As is the case with all of the disclosed methods, the molecule comprising the anti-CD19 scFv FMC63 sequence (SEQ ID NO: 1) can be disposed in any environment. In preferred embodiments, the molecule comprising SEQ ID NO: 1 is expressed on the surface of a cell. In this embodiment, the cell can be of any type, and can be human or non-human (e.g., mouse, rate, rabbit, hamster, etc). In one preferred embodiment, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method, and the cell can be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell.

In an additional embodiment, the cell can be disposed in, or isolated from, any environment capable of maintaining the cell in a viable form, such as blood, tissue or any other sample obtained from a subject, cell culture media, tissue grown ex vivo, a suitable buffer, etc.

Ve. Method of Increasing the Concentration of a Molecule

Very often a molecule of interest is present in a sample in lower-than-desired levels. For example, when a cell is transfected with a foreign gene expression levels of the protein(s) encoded by the foreign gene are sometimes low. The same can be true for molecules secreted from a cell; such molecules are often present in low quantities (but can still be detected using the methods provided herein, if the molecule comprises the anti-CD19 scFv FMC63 sequence (SEQ ID NO: 1). One solution to the problem of low expression levels is to increase the concentration of the molecule of interest, which can be free in solution, or expressed on the surface of a cell. The concentration of intracellularly-expressed molecules of interest can also be enhanced, however the cells must first be lysed to release the molecule. To address this problem, a method of increasing the concentration of cells presenting a molecule comprising the anti-CD19 scFv FMC63 sequence (SEQ ID NO: 1) is provided.

In some embodiments, the method comprises providing a sample comprising cells known or suspected to present a molecule comprising the anti-CD19 scFv FMC63 sequence (SEQ ID NO: 1).

In specific embodiments, the molecule comprising the sequence SEQ ID NO: 1 is a CAR. When the molecule is a CAR it can comprise a molecule, or fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof.

An antigen binding molecule that specifically binds SEQ ID NO: 1, and optionally comprises a detectable label, is provided. When it is decided to employ a detectable label, any detectable label can be employed in the method, as described herein, and suitable labels can be selected using a desired set of criteria. Examples of types of detectable labels include fluorescent labels (e.g., fluorescein, rhodamine, tetramethylrhodamine, eosin, erythrosin, coumarin, methylcoumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science). Suitable optical dyes, including fluoro-phores, are described in Johnson, *Molecular Probes Handbook: A Guide to Fluorescent Probes and Labeling Techniques*, 11$^{th}$ *Edition*, Life Technologies, (2010), hereby expressly incorporated by reference, radiolabels (e.g., isotope markers such as $^{3}H$, $^{11}C$, $^{14}C$, $^{15}N$, $^{18}F$, $^{35}S$, $^{64}CU$, $^{90}Y$, $^{99}Tc$, $^{111}In$, $^{124}I$ $^{125}I$, $^{131}I$), photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus*, or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNA-BEADS), etc. Strategies for the labeling of proteins are well known in the art and can be employed in the disclosed method. See, e.g., Obermaier et al., (2015) *Methods Mol*

Biol 1295:153-65; Strack (2016) *Nature Methods* 13:33; *Site-Specific Protein Labeling: Methods and Protocols*, (Gautier and Hinner, eds.) 2015, Springer.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds the anti-CD19 scFv FMC63 sequence (SEQ ID NO: 1) (or fragment thereof) can be employed, such as those disclosed herein, e.g., those having one or more of the CDRs shown in FIGS. 5-21.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

A cell presenting a molecule comprising SEQ ID NO: 1 can be of any type, and can be human or non-human (e.g., mouse, rate, rabbit, hamster, etc). In a preferred embodiment, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method, and the cell can be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc.

The sample comprising cells is contacted with the antigen binding molecule, under conditions that permit the formation of a binding complex comprising a molecule comprising anti-CD19 scFv FMC63 sequence (SEQ ID NO: 1) and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

At this stage, no binding complexes may have formed, or a plurality of binding complexes comprising one or more antigen binding molecules bound to a molecule comprising the anti-CD19 scFv FMC63 sequence (SEQ ID NO: 1) (or one or more molecules comprising SEQ ID NO: 1 bound to an antigen binding molecule) may have formed. Unbound molecules comprising SEQ ID NO: 1 and/or unbound antigen binding molecules may also be present in the local environment of any formed binding complexes.

Any molecules or cells not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. If a binding complex is disposed on a bead, the bead itself may be situated in a column or other structure and the same approach can be used.

The solution used to induce the formation of binding complexes can be used, for example, as a wash solution to remove unbound components. Any suitable buffer or solution that does not disrupt formed binding complexes can also be used. Typically, buffers having high salt concentrations, non-physiological pH, containing chaotropes or denaturants, should be avoided when performing this step of the method.

At this stage of the method, a population of cells presenting a molecule comprising the SEQ ID NO: 1 will be present. If a detectable label was employed, the concentration of the cells can be easily determined, consistent with the nature of the label. Cells not expressing the molecule comprising SEQ ID NO: 1 will be absent, and thus the population (or concentration) of cells presenting a molecule comprising SEQ ID NO: 1 will be increased compared to the levels prior to performing the method.

If the concentration of the molecule comprising the anti-CD19 scFv FMC63 sequence (SEQ ID NO: 1) is not at a desired level, the above steps can be repeated a desired number of times. In the context of this step of the method, a desired number of times can also be zero, if the desired concentration of cells is already present.

Vf. Method of Depleting a Population of Immune Cells

When a subject has an immune cell-mediated condition, it can be of significant importance that the condition be controlled in a timely fashion so as to prevent harm to the subject. For example, when a subject has an autoimmune reaction it may be desirable to suppress an immune cell-mediated response by depleting a population of immune cells, in an effort to prevent harm. In another example, a subject receiving immunotherapy may react too strongly to the therapy and be at risk of harm; depleting the population of immune cells administered to the subject may be an effective approach to mitigating the subject's reaction to the immunotherapy. In view of the need for a method of controlling a subject's immune cell-mediated response, a method of depleting a population of immune cells presenting a molecule comprising the anti-CD19 scFv FMC63 sequence (SEQ ID NO: 1) is provided. An antigen binding molecule that specifically recognizes SEQ ID NO: 1, e.g., those having one or more of the CDRs shown in FIG. 6, can be employed in the method.

In some embodiments, the method comprises providing a population of immune cells to be depleted, wherein the cells are known or suspected to be expressing a molecule comprising the anti-CD19 scFv FMC63 sequence (SEQ ID NO: 1).

In specific embodiments, the molecule comprising SEQ ID NO: 1 is a CAR. When the molecule is a CAR it can comprise a molecule, or fragment thereof, selected from the group consisting of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CDl-la/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, and combinations thereof.

An immune cell expressing a molecule comprising the anti-CD19 scFv FMC63 (SEQ ID NO: 1) sequence can be of any type, and can be human or non-human (e.g., mouse, rate, rabbit, hamster, etc). An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method, and the cell can be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc. As the disclosed method can be employed in therapeutic settings, in preferred embodiments the population of immune cells are disposed in a subject, and more preferably a human subject.

Continuing, the immune cells are contacted with an antigen binding molecule that specifically binds to (a) the molecule comprising SEQ ID NO: 1, and (b) an activating molecule expressed on the surface of the immune cell not expressing the molecule comprising SEQ ID NO: 1, under conditions that permit the formation of a ternary binding complex comprising the molecule comprising SEQ ID NO: 1, the activating molecule and the antigen binding molecule. The antigen binding molecule can be disposed on any surface, or no surface at all. For example, the antigen binding molecule (which can also comprise the population of immune cells to be depleted and/or can be present in a buffer) and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

The immune cells are contacted with the antigen binding molecule, under conditions that permit the formation of a ternary binding complex comprising a molecule comprising the anti-CD19 scFv FMC63 (SEQ ID NO: 1) sequence, the antigen binding molecule and an activating molecule expressed on the surface of an immune cell not expressing the molecule comprising SEQ ID NO: 1. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

In preferred embodiments, the contacting is performed by administering the antigen binding molecule directly to a subject. In this embodiment, the subject will already have a population of cells to be depleted, wherein the cells express a molecule comprising the anti-CD19 scFv FMC63 (SEQ ID NO: 1) sequence. Thus, these cells, as well as cells presenting an activating molecule, will be present in the subject prior to the administration of the antigen binding molecule to the subject. The human blood, lymph and tissue environment will permit the formation of ternary binding complexes. The binding of the antigen binding molecule with the molecule comprising the anti-CD19 scFv FMC63 (SEQ ID NO: 1) sequence serves to "tag" those cells presenting the molecule comprising SEQ ID NO: 1 (i.e., the cells to be depleted). This binding event may or may not lead to depletion on its own. When the antigen binding molecule binds the activating molecule to form the ternary binding complex, however, this binding event brings both cells (i.e., the cell expressing the molecule comprising SEQ ID NO: 1, and the cell expressing the activating molecule) together into proximity. The physiological result of the binding event is the killing of the cell expressing the molecule comprising SEQ ID NO: 1. Thus, with multiple binding events occurring throughout the subject the population of immune cells bearing the molecule comprising SEQ ID NO: 1 are depleted and the risk of harm to the subject decreases.

Sequences and SEQ ID NOs

The instant disclosure comprises a number of nucleic acid and polypeptide sequences. For convenience, the table below correlates each sequence with its appropriate description and SEQ ID NO.

| SEQ ID NO | Description | Sequence |
|---|---|---|
| 1 | Anti-CD19 scFv FMC63 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS |
| 2 | Clone 7 VH | ATGGAGACTGGGCTGCGCTGGCTTCTCCTGGTCGCTGTGCTCAAAGGTGTCCAGTGTCAGGAGCAGCTGGAGGAGTCCGGGGGAGACCTGGTCAAGCCTGGAGGAACCCTGACAGTCACCTGCAAAGCCTCTGGATTCTCCTTCAGTAACAATGGAATTTGCTGGGTCCGCCAGGCTCCAGGGAAGGGGCTGGAGTGGATCGGATGTCTTTATGTTGGTAGTAGTGATACCACTTACTACGCGAGCTGGGCGAAAGGCCGATTCACCATCTCCAAAAGCTCGTCGACCACGGTGACTCTACAAATGACCAGTCTGACAGTCGCGGACACGGCCACCTATTTCTGTACGATAAATCTCGGCTTGTGGGGCCCCGGCACCCTGGTCACCGTCTCCTCA |
| 3 | Clone 7 VH | METGLRWLLLVAVLKGVQCQEQLEESGGDLVKPGGTLTVTCKAS<u>GFSFSNN</u>GICWVRQAPGKGLEWIGCL<u>YVGSSDT</u>TYYASWAKGRFTISKSSSTTVTLQMTSLTVADTATYFCTI<u>NLGL</u>WGPGTLVTVSS |
| 4 | Clone 7 HC | METGLRWLLLVAVLKGVQCQEQLEESGGDLVKPGGTLTVTCKAS<u>GFSFSNN</u>GICWVRQAPGKGLEWIGCL<u>YVGSSDT</u>TYYASWAKGRFTISKSSSTTVTLQMTSLTVADTATYFCTI<u>NLGL</u>WGPGTLVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPTCPPPELLGGPSVFIFPPKPKDTLMISRTPEVTCVVVDVSQDDPEVQFTWYINNEQVRTARPPLREQQFNSTIRVVSTLPIAHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYSKLSVPTSEWQRGDVFTCSVMHEALHNHYTQKSISRSPGK |
| 5 | Clone 7 VH CDR1 | GFSFSNN |
| 6 | Clone 7 VH CDR2 | YVGSSD |
| 7 | Clone 7 VH CDR3 | NLGL |
| 8 | Clone 7 VL | ATGGACACGAGGGCCCCCACTCAGCTGCTGGGGCTCCTGCTGCTCTGGCTCCCAGGTGCCACATTTGCCATCGTGGTGACCCAGACTCCATCTTCCAAGTCTGTCCCTGTGGGAGGCACAGTCACCATCAATTGCCAGGCCAGTGAGAGTGTTTATAATAGCGACTGGTTAGCCTGGTATCAGCAGAAACCAGGGCAGCCTCCCAAGCAACTGATCTATGCTGCATCCACTCTGGCATCTGGGGTCCCATCGCGCTTCAAAGGCAGTGGATCTGGGACACAGTTCACTCTCACCATCAGCGATGTGGTGTGTGACGATGCTGCCACTTATTATTGTGCAGGATATAAAAGTAGTAGTACTGATGGGATTGCTTTCGGCGGAGGGACCGAGGTGGTGGTCAAA |
| 9 | Clone 7 VL | MDTRAPTQLLGLLLLWLPGATFAIVVTQTPSSKSVPVGGTVTINC<u>QASESVYNSDWLA</u>WYQQKPGQPPKQLIY<u>AASTLA</u>SGVPSRFKGSGSGTQFTLTISDVVCDDAATYYC<u>AGYKSSSTDGIA</u>FGGGTEVVVK |
| 10 | Clone 7 LC | MDTRAPTQLLGLLLLWLPGATFAIVVTQTPSSKSVPVGGTVTINC<u>QASESVYNSDWLA</u>WYQQKPGQPPKQLIY<u>AASTLA</u>SGVPSRFKGSGSGTQFTLTISDVVCDDAATYYC<u>AGYKSSSTDGIA</u>FGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC |
| 11 | Clone 7 VL CDR1 | QASESVYNSDWLA |
| 12 | Clone 7 VL CDR2 | AASTLAS |
| 13 | Clone 7 VL CDR3 | AGYKSSSTDGIA |
| 14 | Clone 13 VH | ATGGAGACTGGGCTGCGCTGGCTTCTCCTGGTCGCTGTGCTCAAAGGTGTCCAGTGTCAGGAGCAGCTGGAGGAGTCCGGGGGAGACCTGGTCAAGCCTGGAGGAACCCTGAC |

| SEQ ID NO | Description | Sequence |
|---|---|---|
| | | AGTCACCTGCAAAGCCTCTGGATTCTCCTTCAGTAACA<br>ATGGAATTTGCTGGGTCCGCCAGGCTCCAGGGAAGGGG<br>CTGGAGTGGATCGGATGTCTTTATGTTGGTAGTAGTGA<br>TACCACTTACTACGCGAGCTGGGCGAAAGGCCGATTCA<br>CCATCTCCAAAAGCTCGTCGACCACGGTGACTCTACAA<br>ATGACCAGTCTGACAGTCGCGGACACGGCCACCTATTT<br>CTGTACGATAAATCTCGGCTTGTGGGCCCCGGCACCC<br>TGGTCACCGTCTCCTCA |
| 15 | Clone 13 VH | METGLRWLLLVAVLKGVQCQEQLEESGGDLVKPGGTLT<br>VTCKAS<u>GFSFSNN</u>GICWVRQAPGKGLEWIGCL<u>YVGSSDT</u><br><u>TYYAS</u>WAKGRFTISKSSSTTVTLQMTSLTVADTATYFCTI<br><u>NLGL</u>WGPGTLVTVSS |
| 16 | Clone 13 HC | METGLRWLLLVAVLKGVQCQEQLEESGGDLVKPGGTLT<br>VTCKAS<u>GFSFSNN</u>GICWVRQAPGKGLEWIGCL<u>YVGSSDT</u><br><u>TYYAS</u>WAKGRFTISKSSSTTVTLQMTSLTVADTATYFCTI<br><u>NLGL</u>WGPGTLVTVSSGQPKAPSVFPLAPCCGDTPSSTVTL<br>GCLVKGYLPEPVTVTWNSGTLTNGVRTFPSVRQSSGLYSL<br>SSVVSVTSSSQPVTCNVAHPATNTKVDKTVAPSTCSKPTC<br>PPPELLGGPSVFIFPPKPKDTLMISRTPEVTCVVVDVSQDD<br>PEVQFTWYINNEQVRTARPPLREQQFNSTIRVVSTLPIAHQ<br>DWLRGKEFKCKVHNKALPAPIEKTISKARGQPLEPKVYT<br>MGPPREELSSRSVSLTCMINGFYPSDISVEWEKNGKAEDN<br>YKTTPAVLDSDGSYFLYSKLSVPTSEWQRGDVFTCSVMH<br>EALHNHYTQKSISRSPGK |
| 5 | Clone 13 VH CDR1 | GFSFSNN |
| 6 | Clone 13 VH CDR2 | YVGSSD |
| 7 | Clone 13 VH CDR3 | NLGL |
| 17 | Clone 13 VL | ATGGACACGAGGGCCCCCACTCAGCTGCTGGGGCTCCT<br>GCTGCTCTGGCTCCCAGGTGCCACACTTGCCATCGTGGT<br>GACCCAGACTCCATCTTCCAAGTCTGTCCCTGTGGGAG<br>GCACAGTCACCATCAATTGCCAGGCCAGTGAGAGTGTT<br>TATAATAGCGACTGGTTAGCCTGGTATCAGCAGAAACC<br>AGGGCAGCCTCCCAAGCAACTGATCTATGCTGCATCCA<br>CTCTGGCATCTGGGGTCCCATCGCGCTTCAAAGGCAGT<br>GGATCTGGGACACAGTTCACTCTCACCATCAGCGATGT<br>GGTGTGTGACGATGCTGCCACTTATTATTGTGCAGGAT<br>ATAAAAGTAGTAGTACTGATGGGATTGCTTTCGGCGGA<br>GGGACCGAGGTGGTGGTCAAA |
| 18 | Clone 13 VL | MDTRAPTQLLGLLLLWLPGATLAIVVTQTPSSKSVPVGGT<br>VTINC<u>QASESVYNSDWLA</u>WYQQKPGQPPKQLIY<u>AASTLA</u><br><u>S</u>GVPSRFKGSGSGTQFTLTISDVVCDDAATYYC<u>AGYKSSS</u><br><u>TDGIA</u>FGGGTEVVVK |
| 19 | Clone 13 LC | MDTRAPTQLLGLLLLWLPGATLAIVVTQTPSSKSVPVGGT<br>VTINC<u>QASESVYNSDWLA</u>WYQQKPGQPPKQLIY<u>AASTLA</u><br><u>S</u>GVPSRFKGSGSGTQFTLTISDVVCDDAATYYC<u>AGYKSSS</u><br><u>TDGIA</u>FGGGTEVVVKGDPVAPTVLIFPPAADQVATGTVTI<br>VCVANKYFPDVTVTWEVDGTTQTTGIENSKTPQNSADCT<br>YNLSSTLTLTSTQYNSHKEYTCKVTQGTTSVVQSFNRGDC |
| 11 | Clone 13 VL CDR1 | QASESVYNSDWLA |
| 12 | Clone 13 VL CDR2 | AASTLAS |
| 13 | Clone 13 VL CDR3 | AGYKSSTDGIA |
| 20 | Clone 14-1 VH | ATGGAGACTGGGCTGCGCTGGCTTCTCCTGGTCGCTGT<br>GCTCAAAGGTGTCCAGTGTCAGGAGCAGCTGGAGGAGT<br>CCGGGGGAGGCCTGGTCAAGCCTGGGGCATCCCTGACA<br>CTCACCTGCAAAGCCTCTGGATTCGACTTCAGTATCAA<br>CTACTACATGTGCTGGGTCCGCCAGGCTCCAGGGAAGG<br>GGTTGGAGTGGATCGCATGCATTTATACTGGTGATGAT<br>GACACTTTCTACGCGAGCTGGGCGAAAGGCCGGTTCAC<br>CATCTCCAAAACCTCGTCGACCACGGTGACTCTACAAC<br>TGAACAGTCTGACAGCCGCGGACACGGCCACCTATTTC<br>TGTGTGAGAGGTCTATATAGTGGTAGTATTAATAACCT<br>GTGGGGCCCAGGCACCCTGGTCACCGTCTCCTCA |

| SEQ ID NO | Description | Sequence |
|---|---|---|
| 21 | Clone 14-1VH | METGLRWLLLVAVLKGVQCQEQLEESGGGLVKPGASLTL TCKAS<u>GFDFSINY</u>YMCWVRQAPGKGLEWIACI<u>YTGDDD</u>T FYASWAKGRFTISKTSSTTVTLQLNSLTAADTATYFCVR<u>G LYSGSINNL</u>WGPGTLVTVSS |
| 22 | Clone 14-1HC | METGLRWLLLVAVLKGVQCQEQLEESGGGLVKPGASLTL TCKAS<u>GFDFSINY</u>YMCWVRQAPGKGLEWIACI<u>YTGDDD</u>T FYASWAKGRFTISKTSSTTVTLQLNSLTAADTATYFCVR<u>G LYSGSINNL</u>WGPGTLVTVSSGQPKAPSVFPLAPCCGDTPSS TVTLGCLVKGYLPEPVTVTWNSGTLTNGVRTFPSVRQSSG LYSLSSVVSVTSSSQPVTCNVAHPATNTKVDKTVAPSTCS KPTCPPPELLGGPSVFIFPPKPKDTLMISRTPEVTCVVVDVS QDDPEVQFTWYINNEQVRTARPPLREQQFNSTIRVVSTLPI AHQDWLRGKEFKCKVHNKALPAPIEKTISKARGQPLEPK VYTMGPPREELSSRSVSLTCMINGFYPSDISVEWEKNGKA EDNYKTTPAVLDSDGSYFLYSKLSVPTSEWQRGDVFTCS VMHEALHNHYTQKSISRSPGK |
| 23 | Clone 14-1VH CDR1 | GFDFSINY |
| 24 | Clone 14-1VH CDR2 | YTGDD |
| 25 | Clone 14-1VH CDR3 | GLYSGSINNL |
| 26 | Clone 14-1VL | ATGGACACGAGGGCCCCCACTCAGCTGCTGGGGCTCCT GCTGCTCTGGCTCCCAGATGCCAGATGTGCGCTTGTGA TGACCCAGACTCCATCCCTGTGTCTGCAGCTGTGGGA GGCACAGTCACCATCAGTTGCCAGGCCAGTCAGAGTGT TTATAACAACGACTACTTATCCTGGTATCAGCAGAAAC CAGGGCAGCCTCCCAAACTCCTGATCTATTATGCATCC ACTCTGGCATCTGGGGTCTCATCGCGGTTCAAAGGCAG TGGATCTGGGACACAGTTCACTCTCACCATCAGCGACG TGCAGTGTGACGATGCTGCCGCTTACTATTGTCAGGC GTTAAAGGTTATAGTAATGATAATAATGGTTTCGGCGG AGGGACCGAGGTGGTGGTCAAA |
| 27 | Clone 14-1VL | MDTRAPTQLLGLLLLWLPDARCALVMTQTPSPVSAAVGG TVTISC<u>QASQSVYNNDYLS</u>WYQQKPGQPPKLLIY<u>YASTLA S</u>GVSSRFKGSGSGTQFTLTISDVQCDDAAAYYC<u>AGVKGY SNDNNG</u>FGGGTEVVVK |
| 28 | Clone 14-1LC | MDTRAPTQLLGLLLLWLPDARCALVMTQTPSPVSAAVGG TVTISC<u>QASQSVYNNDYLS</u>WYQQKPGQPPKLLIY<u>YASTLA S</u>GVSSRFKGSGSGTQFTLTISDVQCDDAAAYYC<u>AGVKGY SNDNNG</u>FGGGTEVVVKGDPVAPTVLIFPPAADQVATGTV TIVCVANKYFPDVTVTWEVDGTTQTTGIENSKTPQNSADC TYNLSSTLTLTSTQYNSHKEYTCKVTQGTTSVVQSFNRGD C |
| 29 | Clone 14-1 VL CDR1 | QASQSVYNNDYLS |
| 30 | Clone 14-1 VL CDR2 | YASTLAS |
| 31 | Clone 14-1 VL CDR3 | AGVKGYSNDNNG |
| 32 | Clone 14-7 VH | ATGGAGACTGGGCTGCGCTGGCTTCTCCTGGTCGCTGT GCTCAAAGGTGTCCAATGTCAGTCGCTGGAGGAGTCCG GGGGAGGCCTGGTCAAGCCTGGGGCATCCCTGACACTC ACCTGCAAAGCCTCTGGATTCGACTTCAGTATCAACTA CTACATGTGCTGGGTCCGCCAGGCTCCAGGGAAGGGGT TGGAGTGGATCGCATGCATTTATACTGGTGATGATGAC ACTTTCTACGCGAGCTGGGCGAAAGGCCGGTTCACCAT CTCCAAAACCTCGTCGACCACGGTGACTCTACAACTGA ACAGTCTGACAGCCGCGGACACGGCCACCTATTTCTGT GTGAGAGGTCTATATAGTGGTAGTATTAATAACCTGTG GGGCCCAGGCACCCTGGTCACCGTCTCCTCA |
| 33 | Clone 14-7 VH | METGLRWLLLVAVLKGVQCQSLEESGGGLVKPGASLTLT CKAS<u>GFDFSINY</u>YMCWVRQAPGKGLEWIACI<u>YTGDDD</u>TF |

| SEQ ID NO | Description | Sequence |
|---|---|---|
| | | YASWAKGRFTISKTSSTTVTLQLNSLTAADTATYFCVRGL YSGSINNLWGPGTLVTVSS |
| 34 | Clone 14-7 HC | METGLRWLLLVAVLKGVQCQSLEESGGGLVKPGASLTLT CKASGFDFSINYYMCWVRQAPGKGLEWIACIYTGDDDTF YASWAKGRFTISKTSSTTVTLQLNSLTAADTATYFCVRGL YSGSINNLWGPGTLVTVSSGQPKAPSVFPLAPCCGDTPSST VTLGCLVKGYLPEPVTVTWNSGTLTNGVRTFPSVRQSSGL YSLSSVVSVTSSSQPVTCNVAHPATNTKVDKTVAPSTCSK PTCPPPELLGGPSVFIFPPKPKDTLMISRTPEVTCVVVDVSQ DDPEVQFTWYINNEQVRTARPPLREQQFNSTIRVVSTLPIA HQDWLRGKEFKCKVHNKALPAPIEKTISKARGQPLEPKV YTMGPPREELSSRSVSLTCMINGFYPSDISVEWEKNGKAE DNYKTTPAVLDSDGSYFLYSKLSVPTSEWQRGDVFTCSV MHEALHNHYTQKSISRSPGK |
| 23 | Clone 14-7 VH CDR1 | GFDFSINY |
| 24 | Clone 14-7 VH CDR2 | YTGDD |
| 25 | Clone 14-7 VH CDR3 | GLYSGSINNL |
| 35 | Clone 14-7 VL | ATGGACACGAGGGCCCCCACTCAGCTGCTGGGGCTCCT GCTGCTCTGGCTCCCAGATGCCAGATGTGCGCTTGTGA TGACCCAGACTCCATCCCTGTGTCTGCAGCTGTGGGA GGCACAGTCACCATCAGTTGCCAGGCCAGTCAGAGTGT TTATAACAACGACTACTTATCCTGGTATCAGCAGAAAC CAGGGCAGCCTCCCAAACTCCTGATCTATTATGCATCC ACTCTGGCATCTGGGGTCTCATCGCGGTTCAAAGGCAG TGGATCTGGGACACAGTTCACTCTCACCATCAGCGACG TGCAGTGTGACGATGCTGCCGCTTACTATTGTGCAGGC GTTAAAGGTTATAGTAATGATAATAATGGTTTCGGCGG AGGGACCGAGGTGGTGGTCAAA |
| 36 | Clone 14-7 VL | MDTRAPTQLLGLLLLWLPDARCALVMTQTPSPVSAAVGG TVTISCQASQSVYNNDYLSWYQQKPGQPPKLLIYYASTLA SGVSSRFKGSGSGTQFTLTISDVQCDDAAAYYCAGVKGY SNDNNGFGGGTEVVVK |
| 37 | Clone 14-7 LC | MDTRAPTQLLGLLLLWLPDARCALVMTQTPSPVSAAVGG TVTISCQASQSVYNNDYLSWYQQKPGQPPKLLIYYASTLA SGVSSRFKGSGSGTQFTLTISDVQCDDAAAYYCAGVKGY SNDNNGFGGGTEVVVKGDPVAPTVLIFPPAADQVATGTV TIVCVANKYFPDVTVTWEVDGTTQTTGIENSKTPQNSADC TYNLSSTLTLTSTQYNSHKEYTCKVTQGTTSVVQSFNRGD C |
| 29 | Clone 14-7 VL CDR1 | QASQSVYNNDYLS |
| 30 | Clone 14-7 VL CDR2 | YASTLAS |
| 31 | Clone 14-7 VL CDR3 | AGVKGYSNDNNG |
| 38 | Clone 15 VH | ATGGAGACTGGGCTGCGCTGGCTTCTCCTGGTCGCTGT GCTCAAAGGGGTCCAGTGTCAGTCGTTGGAGGAGTCCG GGGGAGACCTGGTCAAGCCTGGGGCATCCCTGACACTC ACCTGCACAGCCTCTGGATTCTCCTTCACGAGCAACTA CTACATGTGCTGGGTCCGCCAGGCTCCAGGGAAGGGGC TGGAGTGGGTCGCGTGCATTTTTCTTGGTAGTAGTGGTA ACACTGTCTACGCGAACTGGGCGAAAGGCCGATTCACC ATCTCCAAAACCTCGTCGACCACGGTGACTCTGCAAAT GACCAGTCTGACAGTCGCGGACACGGCCACCTATTTCT GTGCGAGAGACTATGTTAATGGTTATGACTACTTTAAC TTGTGGGGCCCAGGCACCTTGGTCACCGTCTCCTCA |
| 39 | Clone 15 VH | METGLRWLLLVAVLKGVQCQSLEESGGDLVKPGASLTLT CTASGFSFTSNYYMCWVRQAPGKGLEWVACIFLGSSGNT VYANWAKGRFTISKTSSTTVTLQMTSLTVADTATYFCAR DYVNGYDYFNLWGPGTLVTVSS |

| SEQ ID NO | Description | Sequence |
|---|---|---|
| 40 | Clone 15 HC | METGLRWLLLVAVLKGVQCQSLEESGGDLVKPGASLTLT<br>CTAS<u>GFSFTSNY</u>YMCWVRQAPGKGLEWVACI<u>FLGSSGNT</u><br>VYANWAKGRFTISKTSSTTVTLQMTSLTVADTATYFCAR<br><u>DYVNGYDYFNL</u>WGPGTLVTVSSGQPKAPSVFPLAPCCGD<br>TPSSTVTLGCLVKGYLPEPVTVTWNSGTLTNGVRTFPSVR<br>QSSGLYSLSSVVSVTSSSQPVTCNVAHPATNTKVDKTVAP<br>STCSKPTCPPPELLGGPSVFIFPPKPKDTLMISRTPEVTCVV<br>VDVSQDDPEVQFTWYINNEQVRTARPPLREQQFNSTIRVV<br>STLPIAHQDWLRGKEFKCKVHNKALPAPIEKTISKARGQP<br>LEPKVYTMGPPREELSSRSVSLTCMINGFYPSDISVEWEKN<br>GKAEDNYKTTPAVLDSDGSYFLYSKLSVPTSEWQRGDVF<br>TCSVMHEALHNHYTQKSISRSPGK |
| 41 | Clone 15 VH CDR1 | GFSFTSNY |
| 42 | Clone 15 VH CDR2 | FLGSSG |
| 43 | Clone 15 VH CDR3 | DYVNGYDYFNL |
| 44 | Clone 15 VL | ATGGACACGAGGGCCCCCACTCAGCTGCTGGGGCTCCT<br>GCTGCTCTGGCTCCCAGGTGCCACATTTGCCCAAGTGT<br>GACCCAGACTGCCATCCCCGTGTCTGCGGCTGTTGGAG<br>GCACAGTCACCATCAATTGCCAGTCCAGTCAGAGTGTT<br>TATAATAAGAACTTAGCCTGGTATCAGCAGAAACCAGG<br>GCAGCCTCCCAAAGGCCTGATCTATTCTACATCGACTCT<br>AGATTCTGGGGTCCCATCGCGGTTCAGCGGCAGTGGAT<br>CTGGGACACAGTTCACTCTCACCATCAGCGACGTGCAG<br>TGTGACGATGCTGCCACTTACTACTGTCTAGGCAGTTAT<br>GATTGTAGTAGTGCTGATTGTAATGCTTTCGGCGGAGG<br>GACCGAGGTGGTGGTCAAA |
| 45 | Clone 15 VL | MDTRAPTQLLGLLLLWLPGATFAQVLTQTASPVSAAVGG<br>TVTINC<u>QSSQSVYNKNLA</u>WYQQKPGQPPKGLIY<u>STSTLDS</u><br>GVPSRFSGSGSGTQFTLTISDVQCDDAATYYC<u>LGSYDCSS</u><br><u>ADCNA</u>FGGGTEVVVK |
| 46 | Clone 15 LC | MDTRAPTQLLGLLLLWLPGATFAQVLTQTASPVSAAVGG<br>TVTINC<u>QSSQSVYNKNLA</u>WYQQKPGQPPKGLIY<u>STSTLDS</u><br>GVPSRFSGSGSGTQFTLTISDVQCDDAATYYC<u>LGSYDCSS</u><br><u>ADCNA</u>FGGGTEVVVKGDPVAPTVLIFPPAADQVATGTVTI<br>VCVANKYFPDVTVTWEVDGTTQTTGIENSKTPQNSADCT<br>YNLSSTLTLTSTQYNSHKEYTCKVTQGTTSVVQSFNRGDC |
| 47 | Clone 15 VL CDR1 | QSSQSVYNKNLA |
| 48 | Clone 15 VL CDR2 | STSTLDS |
| 49 | Clone 15 VL CDR3 | LGSYDCSSADCNA |
| 50 | Clone 17 VH | ATGGAGACTGGGCTGCGCTGGCTTCTCCTGGTCGCTGT<br>GCTCAAAGGTGTCCAATGTCAGTCGCTGGAGGAGTCCG<br>GGGGAGGCCTGGTCAAGCCTGGGGCATCCCTGACACTC<br>ACCTGCACAGCCTCTGGATTCTCCTTCAGTGACAGTTGG<br>TACTTGTGTTGGGTCCGCCAGGCTCCAGGGAAGGGGCT<br>GGAGTGGATCGCATGCATTTATACTGGTGATGGTGACA<br>CTTATTACGCGACCTGGGCGAAAGGCCGATTCACCATC<br>TCCAAGACCTCGTCGACCACAGTGACTCTACAAATGAC<br>CAGTCTGACAGCCGCGGACACGGCCACCTATTTCTGTG<br>CGAGGGGTGCCCAATTTTACTTGTGGGGCCAAGGCACC<br>CTGGTCACCGTCTCCTCA |
| 51 | Clone 17 VH | METGLRWLLLVAVLKGVQCQSLEESGGGLVKPGASLTLT<br>CTAS<u>GFSFSDSW</u>YLCWVRQAPGKGLEWIACI<u>YTGDGDTY</u><br>YATWAKGRFTISKTSSTTVTLQMTSLTAADTATYFCAR<u>G</u><br><u>AQFYL</u>WGQGTLVTVSS |
| 52 | Clone 17 HC | METGLRWLLLVAVLKGVQCQSLEESGGGLVKPGASLTLT<br>CTAS<u>GFSFSDSW</u>YLCWVRQAPGKGLEWIACI<u>YTGDGDTY</u><br>YATWAKGRFTISKTSSTTVTLQMTSLTAADTATYFCAR<u>G</u><br><u>AQFYL</u>WGQGTLVTVSSGQPKAPSVFPLAPCCGDTPSSTVT<br>LGCLVKGYLPEPVTVTWNSGTLTNGVRTFPSVRQSSGLYS<br>LSSVVSVTSSSQPVTCNVAHPATNTKVDKTVAPSTCSKPT<br>CPPPELLGGPSVFIFPPKPKDTLMISRTPEVTCVVVDVSQD<br>DPEVQFTWYINNEQVRTARPPLREQQFNSTIRVVSTLPIAH |

-continued

| SEQ ID NO | Description | Sequence |
|---|---|---|
| | | QDWLRGKEFKCKVHNKALPAPIEKTISKARGQPLEPKVYT MGPPREELSSRSVSLTCMINGFYPSDISVEWEKNGKAEDN YKTTPAVLDSDGSYFLYSKLSVPTSEWQRGDVFTCSVMH EALHNHYTQKSISRSPGK |
| 53 | Clone 17 VH CDR1 | GFSFSDSW |
| 54 | Clone 17 VH CDR2 | YTGDG |
| 55 | Clone 17 VH CDR3 | GAQFYL |
| 56 | Clone 17 VL | ATGGACACGAGGGCCCCCACTCAGCTGCTGGGGCTCCT GCTGCTCTGGCTCCCAGGTGCCACATTTGCCCAGGTGCT GACCCAGACTCCATCCTCCGTGTCTGCAGCTGTGGGAG GCACAGTCACCATCAATTGCCAGTCCAGTCAGAGTGTT TATGCCAACACCTACTTATCCTGGTATCAGCAGAAACC AGGGCAGCCTCCCAAGCAACTGATCTATTCTGCATCCA GTCTGGCATCTGGGGTCCCACCGCGGTTCAAAGGCAGT GGATCTGGGACACAGTTCGCTCTCACCATCAGCGACGT GCAGTGTGACGATGCTGCCACTTACTACTGTCTAGGCA GATATAGTTGTGGTCTTGCTGATTGTGCTGCTTTCGGCG GAGGGACCGAGGTGGTGGTCAAA |
| 57 | Clone 17 VL | MDTRAPTQLLGLLLLWLPGATFAQVLTQTPSSVSAAVGG TVTINCQSSQSVYANTYLSWYQQKPGQPPKQLIYSASSLA SGVPPRFKGSGSGTQFALTISDVQCDDAATYYCLGRYSCG LADCAAFGGGTEVVVK |
| 58 | Clone 17 LC | MDTRAPTQLLGLLLLWLPGATFAQVLTQTPSSVSAAVGG TVTINCQSSQSVYANTYLSWYQQKPGQPPKQLIYSASSLA SGVPPRFKGSGSGTQFALTISDVQCDDAATYYCLGRYSCG LADCAAFGGGTEVVVKGDPVAPTVLIFPPAADQVATGTV TIVCVANKYFPDVTVTWEVDGTTQTTGIENSKTPQNSADC TYNLSSTLTLTSTQYNSHKEYTCKVTQGTTSVVQSFNRGD C |
| 59 | Clone 17 VL CDR1 | QSSQSVYANTYLS |
| 60 | Clone 17 VL CDR2 | SASSLAS |
| 61 | Clone 17 VL CDR3 | LGRYSCGLADCAA |
| 11 | 7 VL CDR1 Kabat | QASESVYNSDWLA |
| 12 | 7 VL CDR2 Kabat | AASTLAS |
| 13 | 7 VL CDR3 Kabat | AGYKSSSTDGIA |
| 11 | 13 VL CDR1 Kabat | QASESVYNSDWLA |
| 12 | 13 VL CDR2 Kabat | AASTLAS |
| 13 | 13 VL CDR3 Kabat | AGYKSSSTDGIA |
| 29 | 14-1 VL CDR1 Kabat | QASQSVYNNDYLS |
| 30 | 14-1 VL CDR2 Kabat | YASTLAS |
| 31 | 14-1 VL CDR3 Kabat | AGVKGYSNDNNG |
| 29 | 14-7 VL CDR1 Kabat | QASQSVYNNDYLS |
| 30 | 14-7 VL CDR2 Kabat | YASTLAS |
| 31 | 14-7 VL CDR3 Kabat | AGVKGYSNDNNG |
| 47 | 15 VL CDR1 Kabat | QSSQSVYNKNLA |
| 48 | 15 VL CDR2 Kabat | STSTLDS |

| SEQ ID NO | Description | Sequence |
|---|---|---|
| 49 | 15 VL CDR3 Kabat | LGSYDCSSADCNA |
| 59 | 17 VL CDR1 Kabat | QSSQSVYANTYLS |
| 60 | 17 VL CDR2 Kabat | SASSLAS |
| 61 | 17 VL CDR3 Kabat | LGRYSCGLADCAA |
| 62 | 7 VH CDR1 Kabat | NNGIC |
| 63 | 7 VH CDR2 Kabat | CLYVGSSDTTYYASWAK |
| 7 | 7 VH CDR3 Kabat | NLGL |
| 62 | 13VH CDR1 Kabat | NNGIC |
| 63 | 13 VH CDR2 Kabat | CLYVGSSDTTYYASWAK |
| 7 | 13 VH CDR3 Kabat | NLGL |
| 64 | 14-1 VH CDR1 Kabat | INYYMC |
| 65 | 14-1 VH CDR2 Kabat | CIYTGDDDTFYASWAK |
| 25 | 14-1 VH CDR3 Kabat | GLYSGSINNL |
| 64 | 14-7 VH CDR1 Kabat | INYYMC |
| 65 | 14-7 VH CDR2 Kabat | CIYTGDDDTFYASWAK |
| 25 | 14-7 VH CDR3 Kabat | GLYSGSINNL |
| 66 | 15 VH CDR1 Kabat | SNYYMC |
| 67 | 15 VH CDR2 Kabat | CIFLGSSGNTVYANWAK |
| 43 | 15 VH CDR3 Kabat | DYVNGYDYFNL |
| 68 | 17 VH CDR1 Kabat | DSWYLC |
| 69 | 17 VH CDR2 Kabat | CIYTGDGDTYYATWAK |
| 55 | 17 VH CDR3 Kabat | GAQFYL |
| 11 | 7 VL CDR1 Chothia | QASESVYNSDWLA |
| 12 | 7 VL CDR2 Chothia | AASTLAS |
| 13 | 7 VL CDR3 Chothia | AGYKSSSTDGIA |
| 11 | 13 VL CDR1 Chothia | QASESVYNSDWLA |
| 12 | 13 VL CDR2 Chothia | AASTLAS |
| 13 | 13 VL CDR3 Chothia | AGYKSSSTDGIA |
| 29 | 14-1 VL CDR1 Chothia | QASQSVYNNDYLS |
| 30 | 14-1 VL CDR2 Chothia | YASTLAS |
| 31 | 14-1 VL CDR3 Chothia | AGVKGYSNDNNG |

-continued

| SEQ ID NO | Description | Sequence |
|---|---|---|
| 29 | 14-7 VL CDR1 Chothia | QASQSVYNNDYLS |
| 30 | 14-7 VL CDR2 Chothia | YASTLAS |
| 31 | 14-7 VL CDR3 Chothia | AGVKGYSNDNNG |
| 47 | 15 VL CDR1 Chothia | QSSQSVYNKNLA |
| 48 | 15 VL CDR2 Chothia | STSTLDS |
| 49 | 15 VL CDR3 Chothia | LGSYDCSSADCNA |
| 59 | 17 VL CDR1 Chothia | QSSQSVYANTYLS |
| 60 | 17 VL CDR2 Chothia | SASSLAS |
| 61 | 17 VL CDR3 Chothia | LGRYSCGLADCAA |
| 5 | 7 VH CDR1 Chothia | GFSFSNN |
| 6 | 7 VH CDR2 Chothia | YVGSSD |
| 7 | 7 VH CDR3 Chothia | NLGL |
| 5 | 13 VH CDR1 Chothia | GFSFSNN |
| 6 | 13 VH CDR2 Chothia | YVGSSD |
| 7 | 13 VH CDR3 Chothia | NLGL |
| 23 | 14-1 VH CDR1 Chothia | GFDFSINY |
| 24 | 14-1 VH CDR2 Chothia | YTGDD |
| 25 | 14-1 VH CDR3 Chothia | GLYSGSINNL |
| 23 | 14-7 VH CDR1 Chothia | GFDFSINY |
| 24 | 14-7 VH CDR2 Chothia | YTGDD |
| 25 | 14-7 VH CDR3 Chothia | GLYSGSINNL |
| 41 | 15 VH CDR1 Chothia | GFSFTSNY |
| 42 | 15 VH CDR2 Chothia | FLGSSG |
| 43 | 15 VH CDR3 Chothia | DYVNGYDYFNL |
| 53 | 17 VH CDR1 Chothia | GFSFSDSW |

-continued

| SEQ ID NO | Description | Sequence |
|---|---|---|
| 54 | 17 VH CDR2 Chothia | YTGDG |
| 55 | 17 VH CDR3 Chothia | GAQFYL |
| 11 | 7 VL CDR1 IMGT | QASESVYNSDWLA |
| 12 | 7 VL CDR2 IMGT | AASTLAS |
| 13 | 7 VL CDR3 IMGT | AGYKSSSTDGIA |
| 11 | 13 VL CDR1 IMGT | QASESVYNSDWLA |
| 12 | 13 VL CDR2 IMGT | AASTLAS |
| 13 | 13 VL CDR3 IMGT | AGYKSSSTDGIA |
| 29 | 14-1 VL CDR1 IMGT | QASQSVYNNDYLS |
| 30 | 14-1 VL CDR2 IMGT | YASTLAS |
| 31 | 14-1 VL CDR3 IMGT | AGVKGYSNDNNG |
| 29 | 14-7 VL CDR1 IMGT | QASQSVYNNDYLS |
| 30 | 14-7 VL CDR2 IMGT | YASTLAS |
| 31 | 14-7 VL CDR3 IMGT | AGVKGYSNDNNG |
| 47 | 15 VL CDR1 IMGT | QSSQSVYNKNLA |
| 48 | 15 VL CDR2 IMGT | STSTLDS |
| 49 | 15 VL CDR3 IMGT | LGSYDCSSADCNA |
| 59 | 17 VL CDR1 IMGT | QSSQSVYANTYLS |
| 60 | 17 VL CDR2 IMGT | SASSLAS |
| 61 | 17 VL CDR3 IMGT | LGRYSCGLADCAA |
| 70 | 7 VH CDR 1 IMGT | GFSFSNNGIC |
| 63 | 7 VH CDR 2 IMGT | CLYVGSSDTTYYASWAK |
| 7 | 7 VH CDR 3 IMGT | NLGL |
| 70 | 13 VH CDR 1 IMGT | GFSFSNNGIC |
| 63 | 13 VH CDR 2 IMGT | CLYVGSSDTTYYASWAK |
| 7 | 13 VH CDR 3 IMGT | NLGL |
| 71 | 14-1 VH CDR 1 IMGT | GFDFSINYYMC |
| 65 | 14-1 VH CDR 2 IMGT | CIYTGDDDTFYASWAK |
| 25 | 14-1 VH CDR 3 IMGT | GLYSGSINNL |
| 71 | 14-7 VH CDR 1 IMGT | GFDFSINYYMC |

-continued

| SEQ ID NO | Description | Sequence |
|---|---|---|
| 65 | 14-7 VH CDR 2 IMGT | CIYTGDDDTFYASWAK |
| 25 | 14-7 VH CDR 3 IMGT | GLYSGSINNL |
| 72 | 15 VH CDR 1 IMGT | GFSFTSNYYMC |
| 67 | 15 VH CDR 2 IMGT | CIFLGSSGNTVYANWAK |
| 43 | 15 VH CDR 3 IMGT | DYVNGYDYFNL |
| 73 | 17 VH CDR 1 IMGT | GFSFSDSWYLC |
| 69 | 17 VH CDR 2 IMGT | CIYTGDGDTYYATWAK |
| 55 | 17 VH CDR 3 IMGT | GAQFYL |
| 74 | HUMANIZED FMC63 VL CDR1 | RASQDISKYLN |
| 75 | HUMANIZED FMC63 VL CDR2 | HTSRLHS |
| 76 | HUMANIZED FMC63 VL CDR3 | QQGNTLPYT |
| 77 | HUMANIZED FMC63 VH CDR1 Clothia | GVSLPDY |
| 78 | HUMANIZED FMC63 VH CDR2 Clothia | WGSET |
| 79 | HUMANIZED FMC63 VH CDR3 | HYYYGGSYAMDY |
| 80 | HUMANIZED FMC63 VH CDR1 Kabat | DYGVS |
| 81 | HUMANIZED FMC63 VH CDR2 Kabat/IMGT | VIWGSETTYYNSALKS |
| 82 | HUMANIZED FMC63 VH CDR1 IMGT | GVSLPDYGVS |

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The foregoing written specification is considered to be sufficient to enable one skilled in the art to practice the invention. The foregoing description and Examples that follow detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

The present invention is further illustrated by the following examples, which should not be construed as further limiting. The contents of all references cited throughout this application are expressly incorporated herein by reference.

Example 1

Generation and Screening of Antigen Binding Molecules

Monoclonal antibodies were generated through immunization of rabbits using the anti-CD19 scFv FMC63 (SEQ ID NO: 1), conjugated to Fc as immunogen. Titer was determined via screening polyclonal sera by using Fc as a screen. A secondary screen was performed using CAR T cells assayed via flow cytometry. Once titer was achieved, the immunized rabbits were sacrificed and monoclonals were derived using standard hybridoma generation and subcloning techniques. The final screening of the hybridoma subclones was accomplished via additional rounds of flow cytometry and immunohistochemistry (IHC) of proliferating CAR T cells or fixed cell pellets derived from CAR T cells, respectively. The sequences of the final two subclones selected were determined by standard Sanger sequencing of the hybridomas subclones.

Figure 1B:
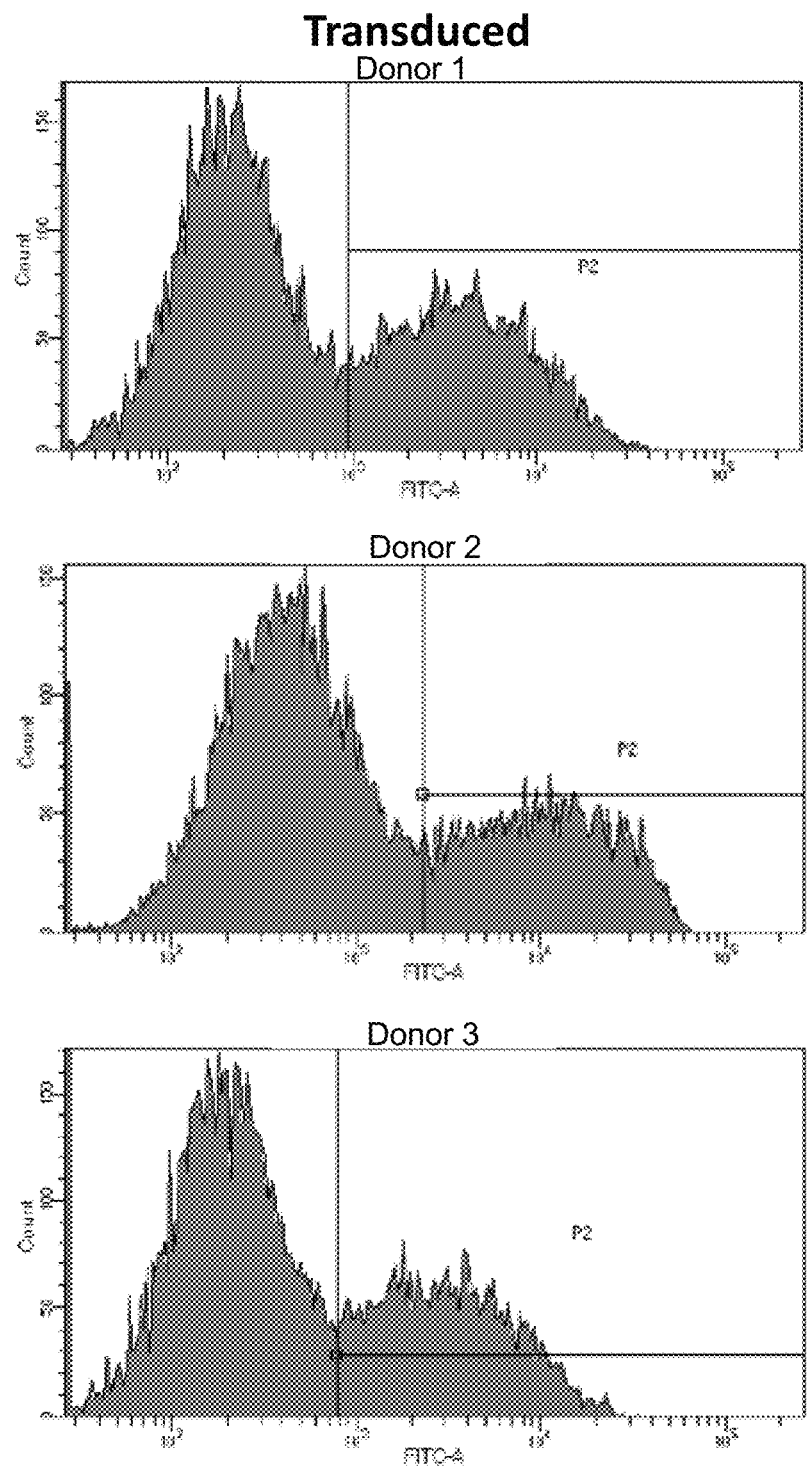
Figure 2:
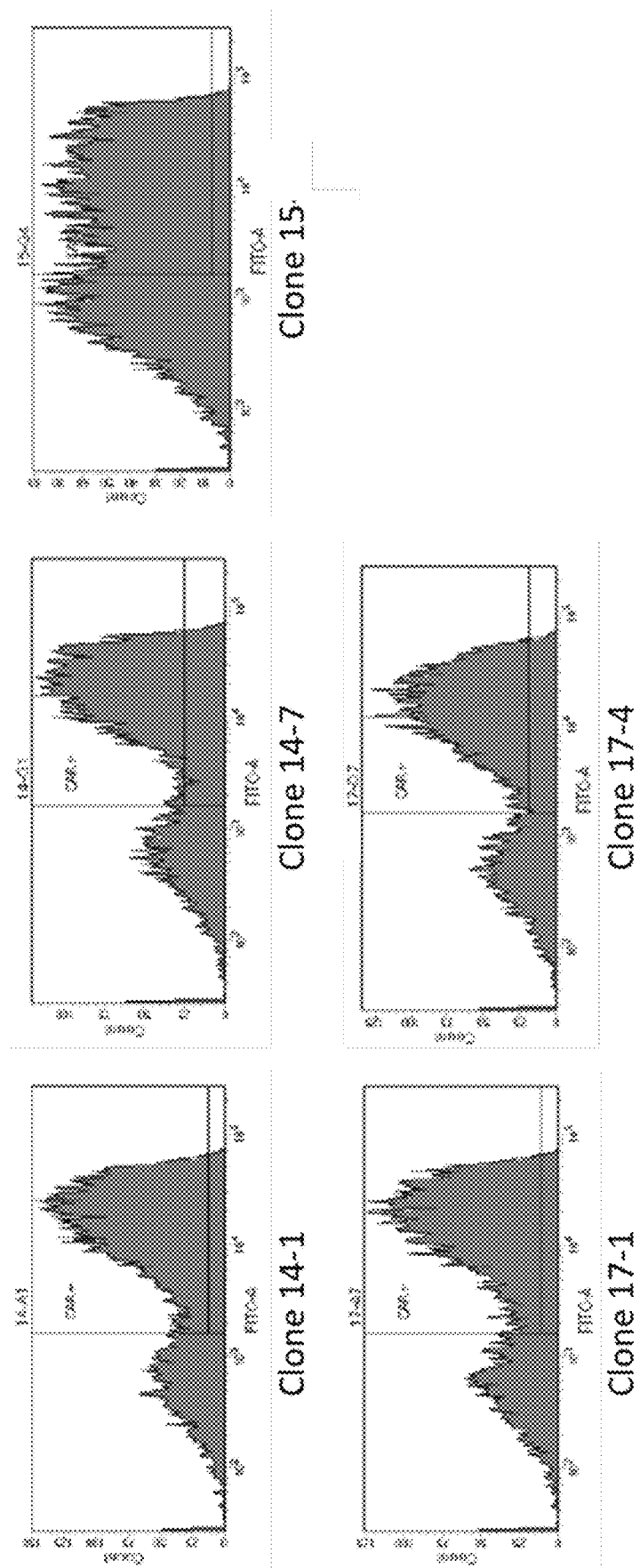
FIG. 2 is a series of plots showing the results of flow cytometry experiments performed using cells transduced with a construct encoding a CAR comprising the anti-CD19 scFv FMC63 and then contacted with anti-scFv antibodies corresponding to five different clones (Clone 14-1, Clone 14-7, Clone 15, Clone 17-1 and Clone 17-4); the plots demonstrate specific binding of the antibodies to the expressed CAR.
Figure 17A:
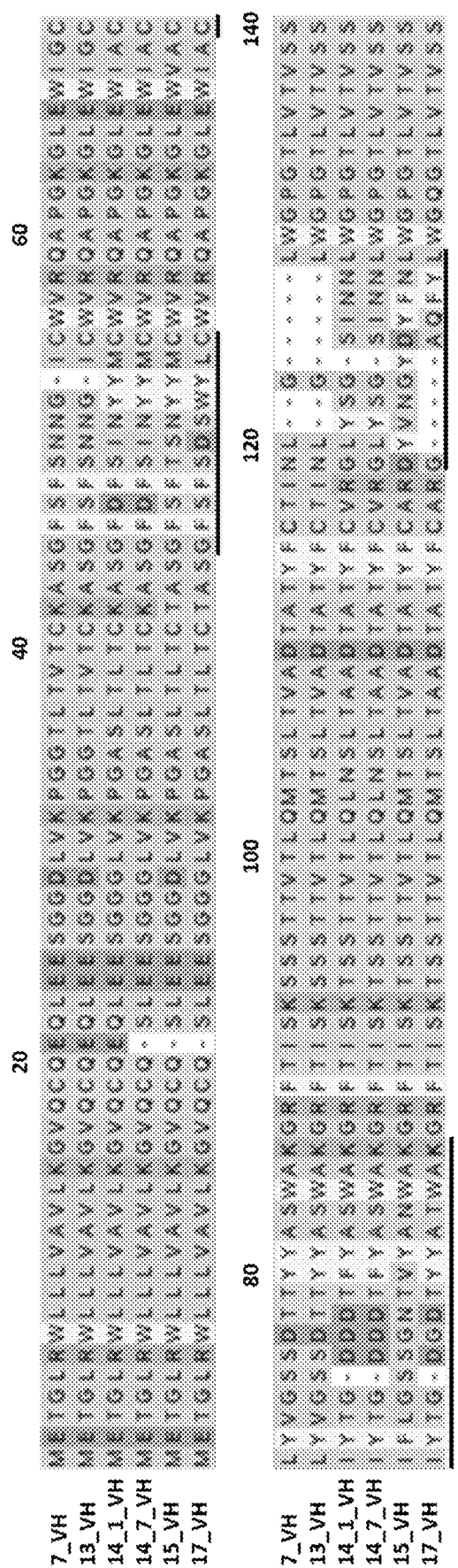
FIGS. 17A and 17B are an alignment showing the variable heavy chain sequences of the six distinct antibodies identified (FIG. 17A), and a clading diagram (FIG. 17B) showing the relationship of the sequences to one another.
Figure 17B:
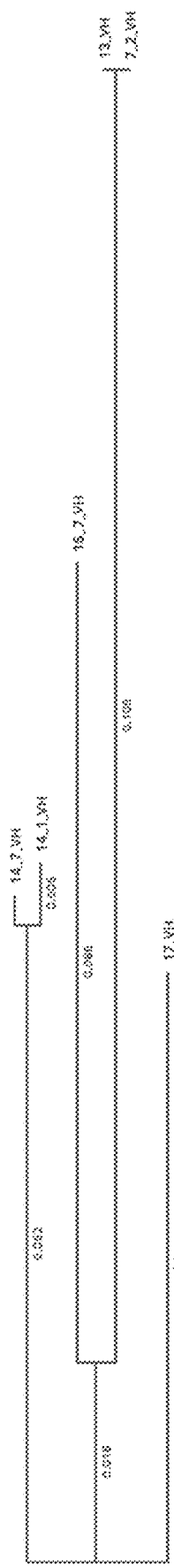
Figure 18A:
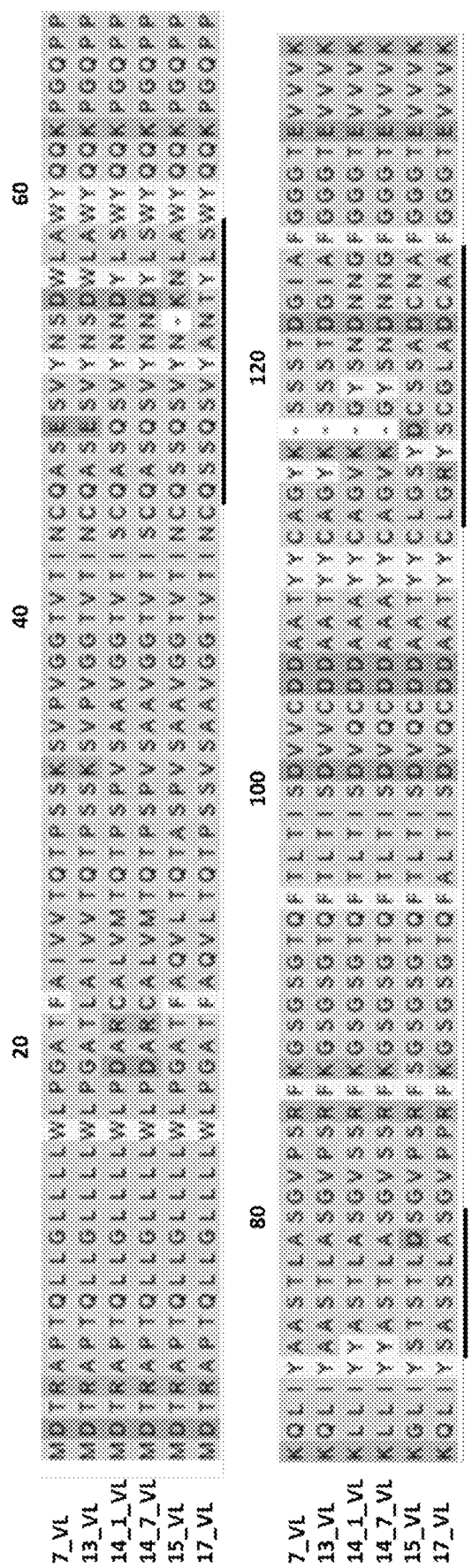
FIGS. 18A and 18B are an alignment showing the variable light chain sequences of the six distinct antibodies identified (FIG. 18A), and a clading diagram (FIG. 18B) showing the relationship of the sequences to one another.
Figure 18B:
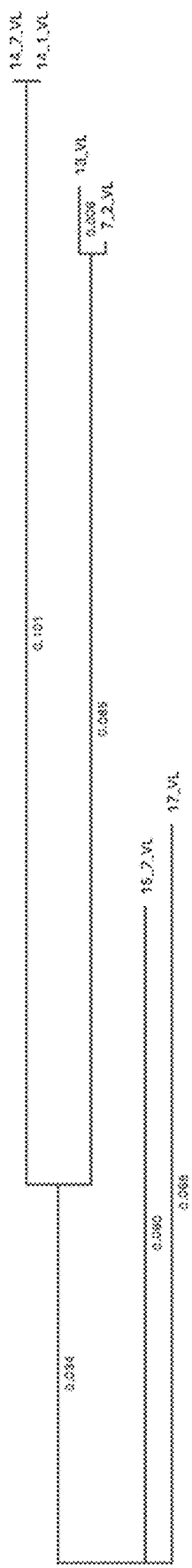

PBMCs were isolated from healthy donor leukopaks (Hemacare™) using Ficoll-Paque density centrifugation per manufacturer's instructions. PBMCs were stimulated using OKT3 (50 ng/ml, Miltenyi Biotec™) in R10 media+IL-2 (300 IU/ml, Proleukin®, Prometheus® Therapeutics and Diagnostics). Two days after stimulation, CAR T cells presenting the anti-CD19 scFv FMC63 (SEQ ID NO: 1) were generated through viral transduction of these activated primary human T cells. Transduction was performed using either a retro- (pMSVG vector) or lentivirus (pGAR vector) depending upon the origin of the CARs used in the screening. Confirmation of CAR construct expression and viral transduction efficiency was determined using Protein L conjugated to phycoerythrin (PE) or fluorescein isothiocyanate (FITC). Results are shown in FIGS. 1A-1B and 2.

Example 2

Immunohistochemistry (IHC) Studies

Several antibodies disclosed herein, (Clones 7 and 13) were assessed with respect to their ability to function as reagents in immunohistochemistry (IHC) studies. To create the fixed cell pellets for IHC staining, ~2e6 CART cells presenting the anti-CD19 scFv FMC63 (SEQ ID NO: 1) were centrifuged and washed with PBS. The cells were resuspended in PBS containing 0.45% paraformaldehyde (PFA) and incubated on a shaking platform for 2 hours at room temperature. After the incubation, the cells were washed once more with PBS and resuspended in PBS with 5% BSA. The results of the IHC experiments are shown in FIGS. 3 and 4A (FIG. 4B shows controls), and demonstrate that at least clones 7 and 13 can be useful in these types of experiments.

Example 3

Use of an Anti-FMC63 Antibody for Purifying Macromolecules and Cells

The antigen binding molecules disclosed herein are anti-idiotypic antigen binding molecules, and recognize an epitope on the anti-CD19 scFv FMC63. An antigen binding molecule (e.g., an antibody) disclosed herein can thus be used to purify a molecule, such as the anti-CD19 scFv FMC63, macromolecule, polymer, cell, material, etc., displaying an epitope that is recognized by the antigen binding molecules disclosed herein.

In some embodiments, an antigen binding molecule disclosed herein (e.g., Clones 7, 13, 14-1, 14-7, 15 and/or 17 and fragments thereof) can be attached to beads, attached to or associated with a resin, which can be disposed in a column or other structure. A sample comprising a molecule comprising all or a fragment of anti-CD19 scFv FMC63 can then be contacted with the beads, resin, etc to which the antigen binding molecule was attached or with which an antigen binding molecule was associated. This allows the formation of an association or binding complex comprising the antigen binding molecule and the molecule comprising all or a fragment of the anti-CD19 scFv FMC63. The beads or resin can then be washed with a suitable solution, such as a buffer solution (e.g., PBS, HEPES, MOPS, Tris, Tricine, etc) having a pH selected to maintain the stability of the molecule comprising all or a fragment of the anti-CD19 scFv FMC63. The washing can remove unwanted and unbound components of the sample. Following the washing step, the molecule comprising all or a fragment of the anti-CD19 scFv FMC63 can then be eluted from the antigen binding molecules using an elution buffer and conditions selected to disrupt any association or binding complexes formed. Examples of suitable elution buffers include 0.1M glycine, pH 2.5-3.0, and 0.1M citric acid, pH 3.0, 50-100 mM triethylamine or triethanolamine, pH 11.5, 3.5-4.0M magnesium chloride, pH 7.0 in 10 mM Tris, 2-6M guanidine, and 2-8M urea. During the elution step, eluted molecules, cells and moieties of interest comprising all or a fragment of the anti-CD19 scFv FMC63 is collected, and purity can be subsequently checked by running a sample on an SDS polyacrylamide gel.

In another embodiment, an antigen binding molecule can be disposed in solution with any molecular entity displaying the epitope, and purified from a mixed population of molecules, cells, etc. and eluted from the beads, resin, or free antibody by washing with 300-500 mM sodium chloride or lowering the pH and neutralizing with 1 M Tris, for proteins, or phosphate buffer. Subsequently, dialysis can be used to return materials to desired buffer conditions.

In some embodiments, cells displaying a molecule comprising all or a fragment of the anti-CD19 scFv FMC63 can be incubated with magnetic beads (e.g., DYNABEADS) with which an antigen binding molecule disclosed herein has been associated. Preferably the incubation is performed under conditions that both allow for the formation of binding complexes/associations, such as under physiological conditions, in the presence of a media selected for this purpose (e.g., RPMI-1640).

Cells bound by the beads (which will be presenting molecules comprising the anti-CD19 scFv FMC63) are then separated from cells not displaying a molecule comprising the anti-CD19 scFv FMC63 or fragment thereof. In some embodiments, the beads can be washed with media, such as RPMI-1640 supplemented with 10% FBS, in the presence of a magnet.

Selected cells, i.e., those presenting molecules that comprise the anti-CD19 scFv FMC63 can then be separated from the beads: First, selected cells are grown out in media. After growing out cells for 48 hours, the magnetic beads can be separated from cells in solution and discarded, leaving a pure population of cells expressing desired molecule.

In an alternative embodiment, the beads are not magnetic, and in this embodiment the above steps can also be followed and adapted to maintain cell integrity, but also to allow separation of bead-bound cells from non-bead bound cells.

In another alternative embodiment, an antigen binding molecule disclosed herein (e.g., Clones 7, 13, 14-1, 14-7, 15 and/or 17 and fragments thereof) can be His-tagged (i.e., labeled with a short polyhistidine sequence), thereby facilitating the separation of cells using a resin comprising a transition metal ion such as $Ni^{2+}$, $Co^{2+}$, $Cu^{2+}$ or $Zn^{2+}$, which are immobilized on the resin. The antigen binding molecules can then be incubated with cells known or suspected to be expressing SEQ ID NO: 1 under conditions suitable for the formation of complexes comprising the cells and the antigen binding molecules. Following the incubation, the cells are contacted with the resin, which can be disposed in a solid structure such as a welled plate, column or other structure. The antigen binding molecule-cell complexes can then be separated from one another by washing with imidazole, which will be of a higher concentration than any imidazole included in any solutions used in the formation of the binding complexes. Eluted cells can then be spun down, washed in RPMI or other suitable media, and then resuspended in media.

Example 4

Activating CAR-Positive T Cells Using an Anti-FMC63 Antigen Binding Molecule

Also provided is a method of activating CAR-positive T cells presenting a molecule comprising a specific idiotope recognized by a specific antigen binding molecule (e.g., an antigen binding molecule that recognizes the anti-CD19 scFv FMC63 (SEQ ID NO: 1), such as those disclosed herein: Clone 7, 13, 14-1, 14-7, 15 and/or 17, and fragments thereof). This method may be adapted for any antibody recognizing a protein of interest on a T-cell containing an activation domain, such as a chimeric antigen receptor (CAR) comprising SEQ ID NO: 1. Activation can be achieved using plate-bound, bead-bound, polymer-bound, or other form of the antibody that specifically recognizes an extracellular component of the CAR or similar molecule.

In some embodiments, the method can be performed as follows: first, a 12-well tissue culture treated plate is coated with 1 mL of a 1.5 µg/mL solution of an anti-CD19 scFv FMC63 antigen binding molecule disclosed herein, which has been diluted in HBSS or other phosphate buffer, and placed in an incubator at 37 C for 2 hours. Next, the plate is washed three times with HBSS or other phosphate buffer having a suitable pH, ionic strength, etc. Continuing, CAR-positive T-cells in OpTmizer media (with supplements) or RPMI-1640 media with 10% FBS are added to the tissue culture treated plate. The cells are then grown at 37 C with 5% $CO_2$.

After 2 days, the cells are examined to determine any increase in the percent CAR-positive cells. This determination can be made by identifying any increase in the expression of any cell-surface and/or internal markers, including, but not limited to 4-1BB, CD69, CD25, PD-1, and Ki-67.

Example 5

Generation of Humanized Sequences from Rabbit Antibodies

The Molecular Operating Environment (MOE) software developed by Chemical Computing Group (CCG) can be used to generate alignments between the rabbit antibody Clones 7, 13, 14-1, 14-7, 15 and 17 and pairs of variable light and heavy chains, VL and VH, respectively from two databases:

(1) The Abysis human database: a database of about 2000 known human VL/VH sequence pairs from IMGT-LigM DB; and
(2) A human germline database: a database of germline sequences.

Humanized models show the best sequence alignments (highest identity to both the VL and VH domains) with fewest gaps. The top 100 antibody pairs from each human database can be exported and clustered using kClust (Hauser, Mayer, & Soding, (2013) *BMC Bioinformatics*, 248). Tables for VL and VH sequences for each of the antibodies, can be constructed, with sequences from each of the two databases clustered at 90% and 95%.

Example 6

Flow Cytometry of Humanized FMC63 CAR

Humanized FMC63 CAR constructs were identified comprising conserved CDR loops (e.g., comprising amino acid sequences defined in Table C and D) and bind to CD19. Jurkat cells expressing FMC63 and humanized FMC63 CAR constructs were generated by transduction with lentivirus carrying the respective constructs. Monoclonal antibodies 14-1, 15, and 17-4 were incubated with CAR-expressing Jurkat cells and detected with a FITC-conjugated goat anti-rabbit F(ab')2 antibody (Thermo). An antibody reactive against all of these CAR constructs was used as a control to verify expression (FIG. 22, top row). Clone 15 binds to the common amino acids in the CDR loops of FMC63 and all the humanized constructs, but shows no reactivity against mock-transduced Jurkat cells. (FIG. 22). Secondary antibody only and mock-transduced controls show no background staining.

TABLE C

CDRs for the light chain variable (VL) region of the humanized FMC63 anti-CD19

| Sequence (Convention) | CDR1 | SEQ ID NO | CDR2 | SEQ ID NO | CDR3 | SEQ ID NO |
|---|---|---|---|---|---|---|
| VL (Chothia) | RASQDISKYLN | 74 | HTSRLHS | 75 | QQGNTLPYT | 76 |
| VL (Kabat) | RASQDISKYLN | 74 | HTSRLHS | 75 | QQGNTLPYT | 76 |
| VL (IMGT) | RASQDISKYLN | 74 | HTSRLHS | 75 | QQGNTLPYT | 76 |

TABLE D

CDRs for the heavy chain variable (VH) region of the humanized FMC63 anti-CD19

| Sequence (Convention) | CDR1 | SEQ ID NO | CDR2 | SEQ ID NO | CDR3 | SEQ ID NO |
|---|---|---|---|---|---|---|
| VH (Chothia) | GVSLPDY | 77 | WGSET | 78 | HYYYGGSYAMDY | 79 |
| VH (Kabat) | DYGVS | 80 | VIWGSETTYNSALKS | | HYYYGGSYAMDY | 79 |
| VH (IMGT) | GVSLPDYGVS | 82 | VIWGSETTYNSALKS | 81 | HYYYGGSYAMDY | 79 |

What is claimed is:

1. An isolated antigen binding molecule that specifically binds a molecule comprising SEQ ID NO: 1, wherein the antigen binding molecule comprises a heavy chain (HC) comprising
   (a) a VH CDR1 region comprising the amino acid sequence of SEQ ID NO: 23;
   (b) a VH CDR2 region comprising the amino acid sequence of SEQ ID NO: 24;
   (c) a VH CDR3 region comprising the amino acid sequence of SEQ ID NO: 25; and a light chain (LC) comprising
   (a) a VL CDR1 region comprising the amino acid sequence of SEQ ID NO: 29;
   (b) a VL CDR2 region comprising the amino acid sequence of SEQ ID NO: 30; and
   (c) a VL CDR3 region comprising the amino acid sequence of SEQ ID NO: 31.

2. The antigen binding molecule of claim 1, wherein the antigen binding molecule is selected from the group consisting of an antibody, an scFv, a Fab, a Fab', a Fv, a F(ab')$_2$, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody an IgG2 antibody having at least one mutation in the hinge region, an IgG3 antibody, an IgG3 antibody having at least one mutation in the hinge region, an IgG4 antibody, an IgG4 antibody having at least one mutation in the hinge region, an antibody comprising at least one non-naturally occurring amino acid, and any combination thereof.

3. The antigen binding molecule of claim 2, wherein the HC comprises a heavy chain variable region (VH) sequence selected from the group consisting of SEQ ID NOs: 21 and 33.

4. An antigen binding molecule, which comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule of claim 3, wherein the antigen binding molecule comprises a heavy chain (HC) comprising
   (a) a VH CDR1 region comprising the amino acid sequence of SEQ ID NO: 23;
   (b) a VH CDR2 region comprising the amino acid sequence of SEQ ID NO: 24;
   (c) a VH CDR3 region comprising the amino acid sequence of SEQ ID NO: 25; and a light chain (LC) comprising
   (a) a VL CDR1 region comprising the amino acid sequence of SEQ ID NO: 29;
   (b) a VL CDR2 region comprising the amino acid sequence of SEQ ID NO: 30; and
   (c) a VL CDR3 region comprising the amino acid sequence of SEQ ID NO: 31.

5. The antigen binding molecule of claim 2, wherein the LC comprises a light chain variable region (VL) sequence selected from the group consisting of SEQ ID NOs: 27 and 36.

6. An antigen binding molecule, which comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VL of an antigen binding molecule of claim 5, wherein the antigen binding molecule comprises a heavy chain (HC) comprising
   (a) a VH CDR1 region comprising the amino acid sequence of SEQ ID NO: 23;
   (b) a VH CDR2 region comprising the amino acid sequence of SEQ ID NO: 24;
   (c) a VH CDR3 region comprising the amino acid sequence of SEQ ID NO: 25; and a light chain (LC) comprising
   (a) a VL CDR1 region comprising the amino acid sequence of SEQ ID NO: 29;
   (b) a VL CDR2 region comprising the amino acid sequence of SEQ ID NO: 30; and
   (c) a VL CDR3 region comprising the amino acid sequence of SEQ ID NO: 31.

7. The antigen binding molecule of claim 2, wherein the antigen binding molecule comprises:
   (a) a VH comprising the amino acid sequence of SEQ ID NO: 21; and
   (b) a VL comprising the amino acid sequence of SEQ ID NO: 27.

8. A composition comprising the antigen binding molecule of claim 1.

9. The antigen binding molecule of claim 4, wherein the VH amino acid sequence is at least about 90% identical to a VH of an antigen binding molecule of claim 3.

10. The antigen binding molecule of claim 9, wherein the VH amino acid sequence is at least about 95% identical to a VH of an antigen binding molecule of claim 3.

11. The antigen binding molecule of claim 6, wherein the VL amino acid sequence is at least about 90% identical to a VL of an antigen binding molecule of claim 5.

12. The antigen binding molecule of claim 11, wherein the VL amino acid sequence is at least about 95% identical to a VL of an antigen binding molecule of claim 5.

* * * * *